(12) United States Patent
Messinger et al.

(10) Patent No.: US 8,080,540 B2
(45) Date of Patent: Dec. 20, 2011

(54) THERAPEUTICALLY ACTIVE TRIAZOLES AND THEIR USE

(75) Inventors: Josef Messinger, Sehnde (DE); Uwe Schoen, Burgdorf (DE); Heinrich-Hubert Thole, Hannover (DE); Bettina Husen, Hannover (DE); Pasi Koskimies, Turku (FI); Lila Kallio nee Pirkkala, Kaarina (FI)

(73) Assignee: Abbott Products GmbH, Hannover (DE)

( * ) Notice: Subject to any disclaimer, the term of this patent is extended or adjusted under 35 U.S.C. 154(b) by 977 days.

(21) Appl. No.: 11/856,768

(22) Filed: Sep. 18, 2007

(65) Prior Publication Data

US 2008/0146531 A1    Jun. 19, 2008

Related U.S. Application Data

(60) Provisional application No. 60/845,496, filed on Sep. 19, 2006, provisional application No. 60/957,848, filed on Aug. 24, 2007.

(51) Int. Cl.
  *A61K 31/58*    (2006.01)
  *C07J 43/00*    (2006.01)

(52) U.S. Cl. ........ 514/176; 514/825; 514/826; 514/863; 514/866; 514/903; 540/108

(58) Field of Classification Search ............ 540/108; 514/176
See application file for complete search history.

(56) References Cited

U.S. PATENT DOCUMENTS

| | | | |
|---|---|---|---|
| 3,347,878 | A | 10/1967 | Boswell |
| 3,413,321 | A | 11/1968 | Boswell, Jr. |
| 5,993,856 | A | 11/1999 | Ragavan et al. |
| 6,416,778 | B1 | 7/2002 | Ragavan et al. |
| 6,541,463 | B1 | 4/2003 | Labrie et al. |
| 6,652,874 | B2 | 11/2003 | Ragavan et al. |
| 6,903,102 | B2 | 6/2005 | Guzi et al. |
| 2003/0170292 | A1 | 9/2003 | Yong et al. |
| 2006/0009434 | A1 | 1/2006 | Hillisch et al. |
| 2006/0052461 | A1 | 3/2006 | Hillisch et al. |
| 2006/0271710 | A1 | 11/2006 | Chang et al. |

FOREIGN PATENT DOCUMENTS

| | | |
|---|---|---|
| EP | 0 367 576 A2 | 5/1990 |
| EP | 0 977 555 | 7/1998 |
| EP | 0902022 | 6/2006 |
| WO | WO 99/46279 | 9/1999 |
| WO | WO 00/07996 A2 | 2/2000 |
| WO | WO 01/42181 A1 | 6/2001 |
| WO | WO 02/26706 A2 | 4/2002 |
| WO | WO 03/017973 A1 | 3/2003 |
| WO | WO 03/022835 A1 | 3/2003 |
| WO | WO 03/033487 A1 | 4/2003 |
| WO | WO 03/101972 A1 | 12/2003 |
| WO | WO 2004/046111 A1 | 6/2004 |
| WO | WO 2004/060488 A1 | 7/2004 |
| WO | WO 2004/080271 A2 | 9/2004 |
| WO | WO 2004/085345 A2 | 10/2004 |
| WO | WO 2004/085457 A2 | 10/2004 |
| WO | WO 2004/110459 A1 | 12/2004 |
| WO | WO 2005/032527 A2 | 4/2005 |
| WO | WO 2005/047303 A2 | 5/2005 |
| WO | WO 2005/084295 A2 | 9/2005 |
| WO | WO 2006/003012 A1 | 1/2006 |
| WO | WO 2006/003013 A2 | 1/2006 |
| WO | WO 2006/027347 A1 | 3/2006 |
| WO | WO 2006/032885 A2 | 3/2006 |
| WO | WO 2006/063585 A1 | 6/2006 |
| WO | WO2006/063615 | 6/2006 |
| WO | WO 2006/125800 A1 | 11/2006 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*
Deluca et al., "Inhibitory effects of fluorine-substituted estrogens on the activity of 17beta-hydroxysteroid dehydrogenases." Molecular and Cellular Endocrinology, vol. 248, pp. 218-224, 2006.*
"Lessons learned from marketed and investigational pro-drugs", J.Med.Chem., 47, 2393-2404, 2004, Ettmayer et al.
Andersen, S.; (1995) "Molecular genetics of androgenic 17β-Hydroxysteroid Dehydrogenases"; J. Steroid Biochem. Molec. Biol., 55(5-6):533-534.
Andersen, J et al.; (2005) "Efficient One-Pot Synthesis of 1-Aryl 1,2,3-Triazoles from Aryl Halides and Terminal Alkynes in the Presence of Sodium Azide" Synlett, 2005, 19:2941.
Burow, Me et al.; "Phytochemical glyceollins, isolated from soy, mediate antihormonal effects through estrogen receptor alpha and beta"; *J. Clin. Endocrinol. Metab.* 86 (2001) (4), pp. 1750-1758.

(Continued)

*Primary Examiner* — Barbara P Badio
(74) *Attorney, Agent, or Firm* — Crowell & Moring LLP

(57) ABSTRACT

Estratrien-triazoles corresponding to formula (I) (shown below) which are useful in therapy, especially for the treatment and/or prevention or inhibition of a steroid hormone dependent disorder, preferably a steroid hormone dependent disease or disorder requiring the inhibition of a 17β-hydroxysteroid dehydrogenase (17β-HSD) such as 17β-HSD type 1, type 2 or type 3 enzyme.

22 Claims, No Drawings

OTHER PUBLICATIONS

Dong, Y et al. (1998) "17β-hydroxysteroid dehydrogenases in human bone cells"; J. Bone Min. Res., 13:1539-1546.

Einspanier, A. et al.; "Induction of endometriosis in the marmoset monkey (*Callithrix jacchus*)"; Mol Hum Reprod. May 2006;12(5):291-9. Epub Apr. 11, 2006.

Geissler WM et al. (1994) "Male pseudohermaphroditism caused by mutations of testicular 17beta-hydroxysteroid dehydrogenase 3."; Nat Genet., 7:34-9.

Gruemmer, R. et al.; "Peritoneal endometriosis: validation of an in vivo model"; *Hum. Reprod.* 16 (2001) (8), pp. 1736-1743.

Husen, B. et al.; (2006) "Evaluation of inhibitors for 17β-hydroxysteroid dehydrogenase type 1 in vivo in immunodeficient mice inoculated with MCF-7 cells stably expressing the recombinant human enzyme"; Mol Cell Endocrinol. Mar. 27, 2006;248(1-2):109-13. Epub Jan. 10, 2006.

Koffmann B et al. (1991) "Evidence for involvement of tyrosine in estradiol binding by rat uterus estrogen receptor." J. Steroid. Biochem. Mol. Biol. 38(2):135-139.

Labaree et al. (2003] "Synthesis and Evaluation of B-, C- and D-ring substituted estradiol carboxylic acid esters as locally active estrogens" J. Med. Chem. 46:1886-1904.

Labrie F et al. (1997) "The key role of 17 beta-hydroxysteroid dehydrogenases in sex steroid biology." Steroids, 62:148-58.

Labrie et al. (2000) "Role of 17 beta-hydroxysteroid dehydrogenases in sex steroid formation in peripheral intracrine tissues" Trends Endocrinol Metab., 11:421-7.

Lawrence et al (2005) "Novel and potent 17beta-hydroxysteroid dehydrogenase type 1 inhibitors." J Med Chem. 48(8):2759-62.

Liu et al (1992) "Synthesis of high affinity fluorine-substituted ligands for the androgen receptor. Potential agents for imaging prostatic cancer by positron emission tomography." J Med Chem. 35(11):2113-29.

Medicinal Chemistry: Principles and Practice, 1994, ISBN 0-85186-494-5, Ed.: F. D. King, p. 215.

Oefelein, MG & Cornum, R (2000) "Failure to achieve castrate levels of testosterone during luteinizing hormone releasing hormone agonist therapy: the case for monitoring serum testosterone and a treatment decision algorithm." J Urol.; 164(Iss. 3, Pt. 1):726-9.

Pelletier & Poirier (1996) "Synthesis and evaluation of estradiol derivatives with 16α-(bromoalkylamide), 16α-(bromoalkyl) or 16α-(bromoalkynyl) side chain as inhibitors of 17β-hydroxysteroid dehydrogenase type 1 without estrogenic activity" Bioorg Med Chem, 4(10):1617-1628.

Poirier et al. (1991) "Synthesis of 17β-estradiol derivatives with N-Butyl, N-methyl alkylamide side chain at position 15." Tetrahedron, 47(37):7751-7766.

Poirier et al. (1996) "D-Ring alkylamine derivatives of estradiol: effect on ER-binding affinity and antiestrogenic activity" Bioorg Med Chem Lett 6(21):2537-2542.

Poirier et al. (1998) "A 6β-(Thiaheptanamide) Derivative of Estradiol as inhibitor of 17β-Hydroxysteroid Dehydrogenase Type 1", J. Steroid Biochem. Molec. Biol., 64:83-90.

Poirier, D.; (2003) "Inhibitors of 17 beta-hydroxysteroid dehydrogenases" Curr Med Chem. 10:453-77.

Rostovtsev, VV. et al.; "A Stepwise Huisgen Cycloaddition Process: Copper(I)-Catalyzed Regioselective Ligation of Azides and Terminal Alkynes" Angew. Chem., 2002, 41(14), 2596-2599.

Sam et al. (1998) "C16 and C17 Derivatives of Estradiol as Inhibitors of 17β-Hydroxysteroid Dehydrogenase Type 1: Chemical Synthesis and Structure-Activity Relationships", Drug Design and Discovery, 15(3):157-180.

Stella, J; "Pro-drugs as therapeutics", Expert Opin. Ther. Patents, 14(3), 277-280, 2004.

Suginome et al. (1989), J. Org. Chem, 54(25) 5945.

Tamaya et al. (1985) "Comparison of cellular levels of steroid receptors in uterine leiomyoma and myometrium." Acta Obstet Gynecol Scand., 64:307-9.

Tremblay & Poirier (1998) "Overview of a Rational Approach to Design Type I 17β- Hydroxysteroid Dehydrogenase inhibitors Without Estrogenic Activity: Chemical Synthesis and Biological Evaluation", J. Steroid Biochem. Molec. Biol., 66:179-191.

Chetrite and Pasqualini (2001) "The selective estrogen enzyme modulator (SEEM) in breast cancer" Journal of Steroid Biochemistry & Molecular Biology 76: 95-104.

Smith et al. (2001) "Inhibitors of steroidogenesis as agents for the treatment of hormone-dependent cancers" Exp. Opin. Ther. Patents 11(5): 789-824.

Blomquist et al. (2002) "Androgenic and estrogenic 17beta-hydroxysteroid dehydrogenase/17-ketosteroid reductase in human ovarian eipthelial tumors: evidence for the type 1, 2, and 5 isoforms" Journal of Steroid Biochemistry & Molecular Biology, 153: 453-464.

Zeitoun and Bulun (1999) "Aromatase: a key molecule in the pathophysiology of endometriosis and a therapueutic target" Fertility and Sterility 72(6): 961-696.

Bulun et al. (2000) "Estrogen biosynthesis in endometriosis: molecular basis and clinical relevance" Journal of Molecular Endocrinology 25:35-42.

Kitawaki et al. (2000) "Progesterone Induction of 17b-Hydroxysteroid Dehydrogenase Type 2 during the Secretory Phase Occurs in the Endometrium of Estrogen-Dependent Benign Disease But Not in Normal Endometrium" J Clin Endocrinol Metab 85:3292-3296.

Janssen et al. (1999) "Estradiol Formation by Human Osteoblasts via Multiple Pathways: Relation With Osteoblast Function" Journal of Cellular Biochemistry 75:528-537.

Moghrabi and Anderson (1998) "17b-Hydroxysteroid Dehydrogenases: Physiological Roles in Health and Disease" TEM 9(7):265-270.

Blomquist et al. (1997) "Intracellular regulation of 17beta-hydroxysteroid dehydrogenase type 2 catalytic activity in A431 cells" Journal of Endocrinology 153:453-464.

Ngatcha et al. (2000) "Androsterone 3-Substituted Derivatives as Inhibitors of Type 3 17beta-Hydroxysteroid Dehydrogenase" Bioorganic & Medicinal Chemistry Letters 10:2533-2536.

Harle et al. (2005) "Predictive and potentially predictive factors in early arthritis: a multidisciplinary approach" Rheumatology 44:426-433.

Lukacik et al. (2006) "Structure and function of human 17beta-hydroxysteroid dehydrogenases" Molecular and Cellular Endocrinology 248: 61-71.

* cited by examiner

THERAPEUTICALLY ACTIVE TRIAZOLES AND THEIR USE

CROSS REFERENCE TO RELATED APPLICATION

This application claims priority from U.S. provisional patent application No. 60/845,496, filed Sep. 19, 2006 and U.S. provisional patent application No. 60/957,848, filed Aug. 24, 2007, the entire disclosures of which are incorporated herein by reference.

FIELD OF THE INVENTION

The present invention relates to novel estratrien-triazole derivatives which represent inhibitory compounds of the 17β-hydroxysteroid dehydrogenase enzymes, preferably of the 17β-hydroxysteroid dehydrogenase type 1 (17β-HSD1), type 2 (17β-HSD2) or type 3 (17β-HSD3) enzyme, as well as to salts of these compounds, to pharmaceutical preparations containing these compounds and to processes for the preparation of these compounds. Furthermore, the invention concerns the therapeutic use of said estratrien-triazole derivatives, particularly their use in the treatment or prevention of steroid hormone dependent diseases or disorders, such as steroid hormone dependent diseases or disorders requiring the inhibition of 17β-hydroxysteroid dehydrogenase enzymes, in particular 17β-HSD type I enzymes, and/or requiring the modulation of the endogenous 17β-estradiol and/or testosterone concentration.

BACKGROUND OF THE INVENTION

The publications and other materials used herein to illuminate the background of the invention, and in particular, cases to provide additional details respecting the practice, are expressly incorporated by reference.

Mammalian 17β-hydroxysteroid dehydrogenases (17β-HSDs) are NAD(H) or NADP(H) dependent enzymes which catalyze the final steps in male and female sex hormone biosynthesis. These enzymes convert inactive 17-keto-steroids into their active 17β-hydroxy-forms or catalyze the oxidation of the 17β-hydroxy-forms into the 17-keto-steroids. Because estrogens and androgens have the highest affinity for their receptors in the respective 17β-hydroxy form, 17β-HSD enzymes play an essential role in the tissue-selective regulation of the activity of sex steroid hormones.

At present, 10 human members of the 17β-HSD enzyme family have been described (types 1-5, 7, 8, 10, 11 and 12). The human 17β-HSD family members share less than 30% similarity in their primary structure. The 17β-HSDs are expressed in distinct, though in some cases, overlapping patterns. The different types of 17β-HSDs also differ in their substrate and cofactor specificities. In intact cells in culture, the 17β-HSDs catalyze the reaction in a unidirectional way: types 1, 3, 5 and 7 use NADP(H) as a cofactor and catalyze the reductive reaction (activation), while types 2, 4, 8 and 10 catalyze the oxidative reaction (inactivation) using NAD(H) as a cofactor [see e.g. Labrie et al. (2000) "Role of 17 beta-hydroxysteroid dehydrogenases in sex steroid formation in peripheral intracrine tissues" Trends Endocrinol Metab., 11:421-7].

Due to their essential role in the tissue-selective regulation of the activity of sex steroid hormones 17β-HSDs can be involved in the occurrence and development of estrogen-sensitive pathologies (f. ex. breast, ovarian, uterine and endometrium cancers etc.) and androgen-sensitive pathologies (f. ex. prostate cancer, benign prostatic hyperplasia, acne, hirsutism, etc). Furthermore, many types of 17β-HSD have been shown to be involved in the pathogenesis of particular human disorders. For example, 17β-HSD3 is known to be involved in the development of pseudohermaphroditism, the 17β-HSD8 plays a role in polycystic kidney disease and the 17β-HSD4 is related to the occurrence of bifunctional enzyme deficiency. Therefore treatment of sex steroid-sensitive diseases by administration of specific inhibitors of the 17β-HSDs enzymes have been suggested, optionally in combination with potent and specific antiestrogens and antiandrogens [Labrie F et al. (1997) "The key role of 17 beta-hydroxysteroid dehydrogenases in sex steroid biology." Steroids, 62:148-58].

Due to the fact that each type of 17β-HSD has a selective substrate affinity, directional (reductive or oxidative) activity in intact cells, and a particular tissue distribution, the selectivity of drug action could be achieved by targeting a particular 17β-HSD isozyme. By individual modulation of the particular 17β-HSDs, it is possible to influence or even control the local and paracrine concentration of estrogens and androgens in different target tissues.

The best characterized member of the 17β-HSD family is the type 1 17β-HSD [EC 1.1.1.62]. This enzyme could be crystallized in different states of functionality (e.g. with and without ligand and/or co-factor). The 17β-HSD1 catalyzes in vitro the reduction as well as the oxidation between estrone (E1) and estradiol (E2). However, under physiological in vivo conditions the enzyme only catalyzes the reductive reaction from the estrone (E1) to the estradiol (E2). The 17β-HSD1 was found to be expressed in a variety of hormone-dependent tissues, e.g. placenta, mammary gland tissue or uterus and endometrium tissue, respectively.

Estradiol itself is, especially in comparison to the significantly less active estrone, a very potent hormone, which regulates the expression of a variety of genes by binding to the nuclear estrogen receptor and plays an essential role in the proliferation and differentiation of the target cell. Physiological as well as pathological cell proliferations can be estradiol dependent. Especially many breast cancer cells are stimulated by a locally raised estradiol concentration. Furthermore, the occurrence or course of benign pathologies such as endometriosis, uterine leiomyomas (fibroids or myomas), adenomyosis, menorrhagia, metrorrhagia and dysmenorrhea is dependent from the existence of significantly high estradiol levels.

Endometriosis is a well-known gynaecological disorder that affects 10 to 15% of women in the reproductive age. It is a benign disease defined as the presence of viable endometrial gland and stroma cells outside the uterine cavity. It is most frequently found in the pelvic area. In women developing endometriosis, the endometrial cells entering the peritoneal cavity by retrograde menstruation (the most likely mechanism) have the capacity to adhere to and invade the peritoneal lining, and are then able to implant and grow. The implants respond to steroid hormones of the menstrual cycle in a similar way as the endometrium in the uterus. The infiltrating lesions and the blood from these lesions which are unable to leave the body cause inflammation of the surrounding tissue. The most common symptoms of endometriosis are primary or acquired dysmenorrhoea, dyspareunia and (chronic) pelvic pain, especially before and in the menstruation period. Further symptoms could include dysuria, various genitourinary symptoms secondary to urethral obstruction and/or bladder invasion, painful defecation, rectal pressure, defecation urgency and bowel obstruction, bleeding abnormalities, including menorrhagia or metrorrhagia, infertility, primary or secondary, recurrent spontaneous abortions. The occurrence of these symptoms is not related to the extent of the lesions. Some women with severe endometriosis are asymptomatic, while women with mild endometriosis may have severe pain. Up to now, no reliable non-invasive test is available to diagnose endometriosis. Laparoscopy has to be performed to diagnose the disease. Endometriosis is classified according to the 4 stages set up by the American Fertility Society (AFS). Stage I corresponds to minimal disease while stage 1V is severe, depending on the location and the extent of the endometriosis. Endometriosis is found in up to 50% of the women with infertility. However, currently no causal relation has been proven between mild endometriosis and infertility. Moderate to severe endometriosis can cause tubal damage and adhesions leading to infertility. The aims of treatment of endometriosis are pain relief, resolution of the endometriotic tissue and restoration of fertility (if desired). The two common treatments are surgery or anti-inflammatory and/or hormonal therapy or a combination thereof.

Uterine leiomyomas (fibroids or myomas), benign clonal tumours, arise from smooth muscle cells of the human uterus. They are clinically apparent in up to 25% of women and are the single, most common indication for hysterectomy. They cause significant morbidity, including prolonged and heavy menstrual bleeding, pelvic pressure and pain, urinary problems, and, in rare cases, reproductive dysfunction. The pathophysiology of myomas is not well understood. Myomas are found submucosally (beneath the endometrium), intramurally (within the myometrium) and subserosally (projecting out of the serosal compartment of the uterus), but mostly are mixed forms of these 3 different types. The presence of estrogen receptors in leiomyoma cells has been studied by Tamaya et al. (1985) "Comparison of cellular levels of steroid receptors in uterine leiomyoma and myometrium." Acta Obstet Gynecol Scand., 64:307-9. They have shown that the ratios of estrogen receptor compared to progesterone and androgen receptor levels were higher in leiomyomas than in the corresponding normal myometrium. Surgery has long been the main treatment for myomas. Furthermore, medical therapies that have been proposed to treat myomas include administration of a variety of steroids such as the androgenic steroids danazol or gestrinone, GnRH agonists and progestogens, whereby the administration is often associated a variety of serious side-effects.

Dysfunctional uterine bleeding disorders (dysfunctional or abnormal uterine bleeding, metrorrhagia and menorrhagia, hypermenorrhea) are forms of pathological bleeding that are not attributable to organic changes in the uterus (such as, e.g., endometrial carcinoma, myomas, polyps, etc.), systemic coagulation disorders, or a pathological pregnancy (e.g., ectopic pregnancy, impending abortion) [American College of Obstetricians and Gynecologists, 1982]. The average blood loss during normal menstruation is about 30 ml, whereby the period lasts for an average of 5 days. If the blood loss exceeds 80 ml, it is classified as pathological. Metrorrhagias are defined as bleeding that may or may not be accompanied by pain and that cannot be linked to menstruation or cycle. If it lasts over 7 days, the blood loss often exceeds 80 ml. Menorrhagia is menstruation that may or may not be accompanied by pain, normally every 27-28 days, which, when it lasts over 7 days, is associated in most cases with an increased blood loss of over 80 ml. Menorrhagia is a syndrome of unknown origin and one of the most common problems in gynecology. 60% of women refereed with menorrhagia have a hysterectomy within five years. Hypermenorrhea is defined as menstruation that may or may not be accompanied by pain, normally every 27-28 days for 4-5 days with an elevated blood loss of over 80 ml, sometimes even defined as associated with an increased blood loss of over 150 ml. Forms of dysfunctional uterine bleeding (mainly metrorrhagias and menorrhagias) are typical of adolescence and of the time of menopause, in which follicle-stimulating disorders, anovulation, and yellow-body and follicle persistence occur in clusters. The incidence of dysfunctional uterine bleeding is high and represents one of the most frequent reasons for gynecological consultation for women of reproductive age.

Everything that has been said above in relation to the treatment of uterine leiomyomas, endometriosis and dysfunctional uterine bleeding, equally applies to other benign gynaecological disorders, notably adenomyosis and dysmenorrhea. These benign gynaecological disorders are all estrogen sensitive and are treated in a comparable way as described herein before in relation to uterine leiomyomas, endometriosis and dysfunctional uterine bleeding. The available pharmaceutical treatments, however, suffer from the same major drawbacks, i.e. they have to be discontinued once the side-effects become more serious than the symptoms to be treated and symptoms reappear after discontinuation of the therapy.

Since the aforementioned malign and benign pathologies are all 17β-estradiol dependent, a reduction of the endogenous 17β-estradiol concentration in the respective tissue will result in an impaired or reduced proliferation of 17β-estradiol cells in said tissues. Therefore, it may be concluded that selective inhibitors of the 17β-HSD1 enzyme are well suited for their use to impair endogenous productions of estrogens, in particular of 17β-estradiol, in myomas, endometriotic, adenomyotic and endometrial tissue. The application of a compound acting as selective inhibitor on the 17β-HSD1 which preferentially catalyzes the reductive reaction will result in a lowered intracellular estradiol-concentration since the reductive conversion of the estrone into the active estradiol is reduced or suppressed. Therefore, reversible or even irreversible inhibitors of the 17β-HSD1 may play a significant role in the prophylaxis and/or treatment of steroid-hormone, in particular 17β-estradiol, dependent disorders or diseases. Furthermore, the reversible or even irreversible inhibitors of the 17β-HSD1 should have no or only pure antagonistic binding activities to the estradiol receptor, in particular to the estrogen receptor α subtype, since agonistic binding of the estrogen receptor would lead to activation and therefore—by regulation of a variety of genes—to the proliferation and differentiation of the target cell. In contrast, antagonists of the estrogen receptor, so called anti-estrogens, bind competitively to the specific receptor protein thus preventing access of endogenous estrogens to their specific binding site.

At present it is described in the literature that several malignant disease as breast cancer, prostate cancer, ovarian cancer, uterine cancer, endometrial cancer and endometrial hyperplasia may be treated by the administration of a selective 17β-HSD1 inhibitor. Furthermore, a selective 17β-HSD1 inhibitor may be useful for the prevention of the aforementioned hormone-dependent cancers, especially breast cancer (see e.g. WO 2004/080271 (and related 2006/0057628). Furthermore, international patent application WO 2003/017973 describes the use of a selective estrogen enzyme modulator (SEEM) in the manufacture of a drug delivery vehicle for intravaginal administration to treat or prevent a benign gynaecological disorder such as endometriosis in a mammalian female.

Several reversible or irreversible inhibitors of the 17β-HSD1 enzyme of steroidal and even non-steroidal origin are already known from the literature. The characteristics of these inhibitory molecules, which mainly have a substrate or cofactor-like core structure, have been reported in the literature [reviewed in: Poirier D. (2003) "Inhibitors of 17 beta-hydroxysteroid dehydrogenases" Curr Med. Chem. 10:453-77].

The following compounds or compound classes have already been described as 17β-HSD1 inhibitors: For example, Tremblay and Poirier describe an estradiol derivative, 16-[carbamoyl-(bromo-methyl)-alkyl]-estradiol, and tested the same in respect of its inhibition of the estradiol formation catalysed by the enzyme 17β-HSD1 [Tremblay & Poirier (1998) "Overview of a Rational Approach to Design Type I 17β-Hydroxysteroid Dehydrogenase Inhibitors Without Estrogenic Activity: Chemical Synthesis and Biological Evaluation", J. Steroid Biochem. Molec. Biol., 66:179-191]. Poirier and colleagues describe a 6β-thiaheptan-butyl-methyl-amide derivative of estradiol as a potent and selective inhibitor of the 17β-HSD1 enzyme [Poirier et al. (1998) "A 6β-(Thiaheptanamide) Derivative of Estradiol as inhibitor of 17β-Hydroxysteroid Dehydrogenase Type 1", J. Steroid Biochem. Molec. Biol., 64:83-90]. Furthermore, Poirier and colleagues describe new derivatives of 17β-estradiol with long N-butyl, N-methyl alkylamide side chains of three different lengths (n=8, 10 or 12) at position 15, which might be potential inhibitors of the 17β-HSD1 enzyme [Poirier et al. (1991) "Synthesis of 17β-estradiol derivatives with N-Butyl, N-methyl alkylamide side chain at position 15." Tetrahedron, 47(37):7751-7766]. Similar compounds were also disclosed within European patent application EP 0 367 576. However, the biological activity of these compounds was only tested with regard to estrogen receptor binding affinity, estrogenic and anti-estrogenic activity [Poirier et al. (1996) "D-Ring alkylamine derivatives of estradiol: effect on ER-binding affinity and antiestrogenic activity" Bioorg Med Chem Lett 6(21):2537-2542], but not with regard to their ability to inhibit the 17β-HSD1 enzyme. In addition, Pelletier and Poirier describe novel 17β-estradiol derivatives with different bromo-alkyl side chains, which might be potential inhibitors of the 17β-HSD1 enzyme [Pelletier & Poirier (1996) "Synthesis and evaluation of estradiol derivatives with 16α-(bromoalkylamide), 16α-(bromoalkyl) or 16α-(bromoalkynyl) side chain as inhibitors of 17β-hydroxysteroid dehydrogenase type 1 without estrogenic activity" Bioorg Med Chem, 4(10):1617-1628]. Sam and colleagues describe several estradiol derivatives with a halogenated alkyl side chain in 16α or 17α position of the steroidal D-ring which possess 17β-HSD1 inhibiting properties [Sam et al. (1998) "C16 and C17 Derivatives of Estradiol as Inhibitors of 17β-Hydroxysteroid Dehydrogenase Type 1: Chemical Synthesis and Structure-Activity Relationships", Drug Design and Discovery, 15:157-180]. Furthermore, the finding that some anti-estrogens, such as tamoxifen, possess weak 17β-HSD1 inhibiting properties suggested that it may be possible to develop a potent 17β-HSD1 inhibitor that is also anti-estrogenic [reviewed in: Poirier D. (2003)]. Several of the aforementioned already known compounds also display anti-estrogenic properties (e.g. the 6β-thiaheptan-butyl-methyl-amide derivative of estradiol described by Poirier and colleagues [Poirier et al. (1998)]). None of the aforementioned compounds has been clinically used so far.

Furthermore, the international patent application WO 2004/085457 (and related US2006/074060) discloses a variety of estron derivatives with different substituents in $C_2$, $C_3$, $C_6$, $C_{16}$ and/or $C_{17}$ position as potent 17β-HSD1 inhibitors. For some of the compounds it was shown that the substitution of steroid based 17β-HSD1 inhibitors at the $C_2$ position with small hydrophobic groups renders the compounds less estrogenic and are favourable for 17β-HSD1 over 17β-HSD2 discrimination [Lawrence et al (2005) "Novel and potent 17beta-hydroxysteroid dehydrogenase type 1 inhibitors." J Med Chem. 48(8):2759-62].

The international application WO 2005/047303 discloses new 3, 15 substituted 17β-estradiol derivatives with different kind of side chains at position 15, which are potent and selective 17β-HSD1 inhibitors.

Additional compounds representing potential 17β-HSD1 inhibitors were disclosed within international applications WO 2006/003012 (and related US 2006/052461) and WO 2006/003013 (and related) in the form of novel 2-substituted D-homo-estra-1,3,5(110)-trienes and novel 2-substituted estra-1,3,5(10)-trien-17-ones.

The synthesis of different B-, C- and D-ring substituted estradiol carboxylic esters was described by Labaree et al. (2003] "Synthesis and Evaluation of B-, C- and D-ring substituted estradiol carboxylic acid esters as locally active estrogens" J. Med. Chem. 46:1886-1904. However, these esters were only analysed with regard to their estrogenic potential. The related international patent application WO 2004/085345 (and related US 2003/0456374) discloses 15α substituted estradiol compounds bearing a —$(CH_2)_m$—CO—O—R side chain, wherein R is H, a $C_1$-$C_5$ alkyl group, optionally substituted with at least one halogen group, such as $CH_2CH_2F$, or other group (e.g. $CH_2CHF_2$, $CH_2CF_3$ or $CF_3$ group); and m is from 0-5. These 15α estradiol esters are described as locally active estrogens without significant systemic action.

Furthermore, international application WO2006/027347 (and related US 2004/0608501) discloses 15β-substituted estradiol derivatives having selective estrogen receptor activity towards the estrogen receptor α-subtype.

A further well characterized member of the 17β-HSD family is the 17β-HSD type 3 enzyme (17β-HSD3). The 17β-HSD3 has a distinct feature compared to other 17-HSDs: it is found to be expressed almost exclusively the testis, whereas the other isoenzymes are expressed more widely in several tissues. 17β-HSD3 has a crucial role in androgen biosynthesis. It converts 4-androstene-3,17-one (A) to testosterone (T). The biological significance of the 17β-HSD3 is of undeniable physiological importance. Mutations in the gene for 17β-HSD3 have found to lead to decreased T formation in the fetal testis and consequently to a human intersex disorder termed male pseudohermaphroditism [Geissler W M et al. (1994) "Male pseudohermaphroditism caused by mutations of testicular 17beta-hydroxysteroid dehydrogenase 3." Nat. Genet., 7:34-9].

With regard to the indication prostate cancer, the primary cancer cells mostly retain their responsiveness to androgens in their regulation of proliferation, differentiation, and programmed cell death for some period. At present, androgen deprivation is the only effective systemic hormonal therapy available for prostate cancer. The development of selective inhibitors against 17β-HSD3 is a new therapeutic approach for the treatment of androgen dependent disease [Labrie et al. (2000)]. Furthermore, Oefelein et al. reported that the depot GnRH analogue fails, in nearly 20% of cases, to achieve castrate levels of T in men [Oefelein M G & Cornum R (2000) "Failure to achieve castrate levels of testosterone during luteinizing hormone releasing hormone agonist therapy: the case for monitoring serum testosterone and a treatment decision algorithm." J Urol.; 164:726-9]. In order to improve the response rate to endocrine therapy for men with prostate cancer it may be important to selectively inhibit testicular 17β-HSD3 activity. Besides prostate cancer, many other androgen-sensitive diseases, i.e. diseases whose onset or progress is aided by androgenic activity, may be treated by selectively inhibiting 17β-HSD3 activity. These diseases include but are not limited to prostadynia, benign prostatic hyperplasia, prostatitis, acne, seborrhea, hirsutism, androgenic alopecia, precocious puberty, adrenal hyperplasia, and polycystic ovarian syndrome. Furthermore, considering the fact that 17β-HSD3 is found mainly in the testis, the development of potent inhibitors could be of interest for blocking spermatogenesis and as an anti-fertility agent for males.

Several reversible or irreversible inhibitors of the 17β-HSD3 enzymes of steroidal and even non-steroidal origin are already known from the literature. The characteristics of these inhibitory molecules have been reported in the literature [reviewed in: Poirier D. (2003)]. For example, U.S. Pat. No. 6,541,463 discloses androsterone derived inhibitors for 17β-HSD3. These derivatives have been synthesised by parallel solid- and liquid-phase chemistry and some of these compounds showed 2 to 18-fold higher inhibition activity than that of the natural substrate of the enzyme, A-dione, used itself as a inhibitor. Furthermore, the international patent application WO 01/42181 discloses benzyl-tetralins, the chemical structure of which is related to that of the phytoestrogen biochanin, as 17β-HSD3 inhibitors. Moreover, international patent applications, WO 99/46279 (and related U.S. Pat. No. 6,541,463), WO 2003/022835 (and related US 2006/069103), WO 2003/033487 (and related US 2003/0232837), WO 2004/046111 (and related U.S. Pat. No. 7,074, 795 and US 2006/0148816), WO 2004/060488 (and related U.S. Pat. No. 7,053,091 and US 2006/0142338), WO 2004/110459 (and related US 2005/0032778), WO 2005/032527 (and related US 2005/0038053) and WO 2005/084295 (and related US 2005/0192310) disclose compounds which have a 17β-HSD3 inhibitory activity, for the treatment of hormone sensitive diseases.

Microsomal 17β-hydroxysteroid dehydrogenase of human endometrium and placenta (designated 17β-HSD type 2 or 17β-HSD2) was cloned by expression cloning, and found to be equally active using androgens and estrogens as substrates for oxidation [Andersson S. (1995) "Molecular genetics of androgenic 17β-Hydroxysteroid Dehydrogenases." J. Steroid Biochem. Molec. Biol., 55:533-534]]. The recombinant 17β-HSD2 converts the highly active 17β-hydroxysteroids such as estradiol (E2), testosterone (T), and dehydrotestosterone (DHT) to their inactive keto forms. In addition, the 17β-HSD2 can, to a lesser extent, also convert 20β-hydroxyprogesterone (20βP) to progesterone (P). The broad tissue distribution together with the predominant oxidative activity of 17β-HSD2 suggest that the enzyme may play an essential role in the inactivation of highly active 17β-hydroxysteroids, resulting in diminished sex hormone action in target tissues. Dong and colleagues showed significant 17β-HSD2 activity in cultured human osteoblasts and osteoblast-like osteosarcoma cells MG63 and TE85, but not in SaOS-2 [Dong Y et al. (1998) "17β-hydroxysteroid dehydrogenases in human bone cells" J. Bone Min. Res., 13:1539-1546]. The potential for interconversion of E1 to E2, T to A, and DHT to A by bone cells could therefore represent important mechanism for the local regulation of intracellular ligand supply for the estrogen and androgen receptors in the osteoblasts and other steroid sensitive cells. This modulation of steroid levels may be employed for a wide variety of indications, including the following: for the prevention and treatment of osteoporosis, for the treatment of ovarian cancer, breast cancer or endometrial cancer, for the treatment of endometriosis, for the treatment of prostate cancer and/or for the treatment of androgen-dependent hair-loss.

Several reversible or irreversible inhibitors of the 17β-HSD2 enzymes of steroidal and even non-steroidal origin are already known from the literature. The characteristics of these inhibitory molecules have been reported in the literature [reviewed in: Poirier D. (2003)]. In addition, the international patent application WO 02/26706 (and related US 2003-0087952) discloses 17β-HSD2 inhibitors of non-steroidal origin.

Accordingly, there is still a need for the development of compounds which are suited for the treatment and/or prevention of the aforementioned steroid hormone dependent diseases or disorders by selectively inhibiting the 17β-HSD1, 17β-HSD3 and/or 17β-HSD2 enzyme, while desirably failing to substantially inhibit other members of the 17β-HSD protein family or other catalysts of sex steroid degradation or activation. In particular, it is an aim of the present invention to develop selective inhibitors of the 17β-HSD1 enzyme, whereby in addition the compounds have no or only pure antagonistic binding affinities to the estrogen receptor (both subtypes, α and β). Furthermore, an increased metabolic stability of the compounds would be desirable, in order to prevent conversion of the compounds to metabolites with less inhibitory potential on the 17β-HSD1 enzyme.

SUMMARY OF THE INVENTION

Therefore, one object of the present invention is to provide novel inhibitors of the 17β-HSD1 and/or 17β-HSD2 enzyme, which have valuable pharmacological properties and which are suited for the treatment of estrogen dependent diseases and disorders. It is a further object of the present invention to develop novel inhibitors of the 17β-HSD3 enzyme, which have valuable pharmacological properties and which are suited for the treatment of androgen dependent diseases and disorders.

It has now been found that the estratrien-triazole derivatives as described herein would be valuable in therapy, especially in the treatment or prevention of steroid hormone dependent diseases or disorders, such as steroid hormone dependent diseases or disorders requiring the inhibition of 17β-hydroxysteroid dehydrogenase (HSD) enzymes. In particular, compounds of formula I represent potent inhibitors of the 17β-HSD1, 17β-HSD3 and/or 17β-HSD2 enzyme and possess valuable pharmacological properties for the treatment and/or prophylaxis of malignant steroid dependent diseases or disorders such as breast cancer, ovarian cancer, uterine cancer, prostate cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhea, menorrhagia, metrorrhagia, urinary dysfunction, prostadynia, benign prostatic hyperplasia, prostatitis, acne, seborrhea, hirsutism, androgenic alopecia, precocious puberty, adrenal hyperplasia, polycystic ovarian syndrome and/or lower urinary tract syndrome. Further estrogen-dependent diseases which may be treated and/or prevented with an effective amount of a compound of the invention are osteoporosis, multiple sclerosis, rheumatoid arthritis, systemic lupus erythematosus, myastenia gravis, thyroiditis, vasculitis, ulcerative colitis, Crohn's disease, graft versus host and host versus graft disease (organ rejection following transplantation), type I and II diabetes, asthma, squamous cell carcinoma, colon cancer, cognitive dysfunctions, senile dementia, Alzheimer's disease, psoriasis, contact dermatitis, eczema, tissue wounds, skin wrinkles and/or cataracts. Furthermore, compounds of formula I may be useful for the prevention and treatment of osteoporosis, and for blocking spermatogenesis and as an anti-fertility agent for males.

Accordingly, the present invention relates to the use of a compound having the structural formula I

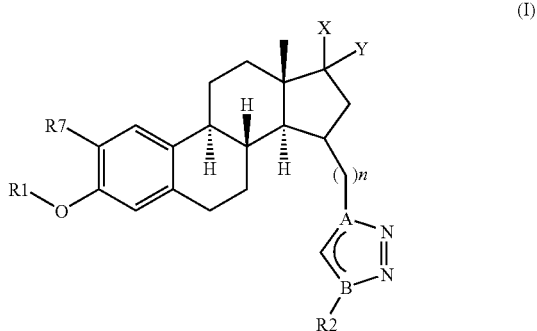

(I)

wherein

A represents N and B represents C, or A represents C and B represents N n represents 1, 2, 3, 4, 5 or 6

X, Y individually represent F, or X and Y together represent =O $R^1$ is selected from the group consisting of:
(a) —H,
(b) —($C_1$-$C_6$)alkyl, which is optionally substituted by halogen, carbonitril, —$OR^3$, —$SR^3$ or
—$COOR^3$; the number of said substituents being 1, 2 or 3 for halogen, and 1 or 2 for any combination of said halogen, carbonitril, —$OR^3$, —$SR^3$ or —$COOR^3$ moieties,
or which is optionally substituted by aryl, in which the aryl moiety is optionally substituted by 1 or 2 substituents independently selected from the group consisting of halogen, hydroxyl and —($C_1$-$C_6$)alkyl, and
(c) -phenyl, which is optionally substituted by halogen, carbonitril, —$OR^3$, —$SR^3$, —$COOR^3$, or —($C_1$-$C_6$)alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ or —($C_1$-$C_6$)alkyl moieties,
wherein each $R^3$ is independently selected from the group consisting of H, —($C_1$-$C_6$)alkyl, optionally substituted by 1, 2 or 3 halogens and/or optionally substituted by 1, 2 or 3 hydroxyl moieties; and aryl, optionally substituted by 1, 2 or 3 halogens, $R^2$ is selected from the group consisting of:
(a) —($C_1$-$C_8$)alkyl,
which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ or —$COR^4$ moieties;
(b) aryl or aryl-($C_1$-$C_8$)alkyl,
in which the aryl moiety is monocyclic or bicyclic;
and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$, or —$COR^4$ moieties;
and in which the alkyl moiety is optionally substituted by 1, 2 or 3 halogens;
(c) heteroaryl or heteroaryl-($C_1$-$C_8$)alkyl,
in which the heteroaryl moiety contains one, two or three heteroatoms independently selected from the group consisting of N, O or S, the number of N atoms being 0, 1, 2 or 3, and the number of O and S atoms each being 0, 1 or 2,
and which heteroaryl moiety is optionally substituted by halogen, carbonitril, nitro,
—$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ or —$COR^4$ moieties,
and in which the alkyl moiety is optionally substituted by 1, 2 or 3 halogens;
(d) ($C_3$-$C_8$)cycloalkyl or ($C_3$-$C_8$)cycloalkyl-($C_1$-$C_8$)alkyl,
in which the cycloalkyl moiety is optionally substituted by halogen, carbonitril, —$OR^4$,
—$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties,
(e) cycloheteroalkyl or cycloheteroalkyl-($C_1$-$C_8$)alkyl,
in which the cycloheteroalkyl moiety is optionally substituted by halogen, carbonitril,
—$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties; and
(f) —($C_1$-$C_8$)alkanoyl
wherein
each $R^4$ and $R^5$ is independently selected from the group consisting of H, —($C_1$-$C_6$)alkyl, optionally substituted by 1, 2 or 3 halogens and/or optionally substituted by 1, 2 or 3 hydroxyl moieties; and aryl and aryl-($C_1$-$C_6$)alkyl, optionally substituted in the aryl moiety by 1, 2 or 3 halogens, or
$R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and
$R^6$ represents —($C_1$-$C_6$)alkyl, which is optionally substituted by 1, 2 or 3 halogens and/or optionally substituted by 1, 2 or 3 hydroxyl moieties;
$R^7$ is selected from the group consisting of
(a) H,
(b) ($C_1$-$C_4$)alkyl,
(c) ($C_1$-$C_4$)alkoxy, and
(d) ($C_1$-$C_4$)alkoxy-($C_1$-$C_4$)alkyl moiety,
and/or all stereoisomers, and/or physiologically compatible salts, and/or metabolites, and/or solvates, and/or prodrugs thereof.

Physiologically compatible salts as well as all tautomers, stereoisomers, racemates, enantiomers of the compounds of the invention and mixtures thereof, unless the formula depicting the compound explicitly shows a particular stereochemistry, are also within the scope of the invention. Such isomers can be isolated by standard resolution techniques, including fractional crystallization and chiral column chromatography. Furthermore the compounds of the invention also include isotopically-labeled and radio-labeled compounds, as well as commonly used pro-drugs and active metabolites of these compounds In one embodiment, the present invention relates to a compound, wherein X and Y individually represent F and which therefore has the following formula

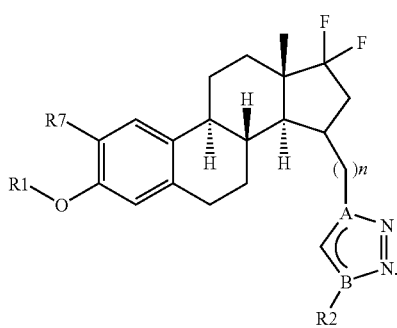

In an alternative embodiment, the present invention relates to a compound, wherein X and Y together represent =O and which therefore has the following formula

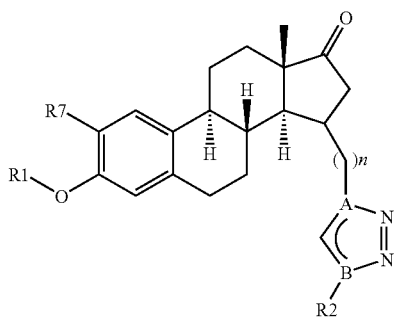

In one embodiment, the present invention relates to a compound of the general formula I, wherein A represents N and B represents C and which compound has the formula (Ix),

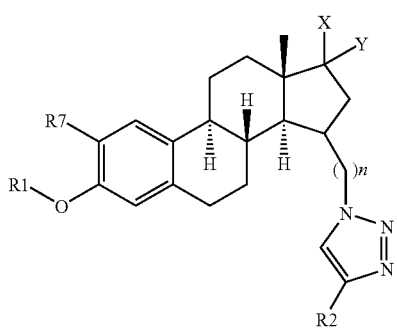
(Ix)

In one embodiment, the present invention relates to a compound of the general formula I, wherein A represents C and B represents N and which compound has the formula (Iy).

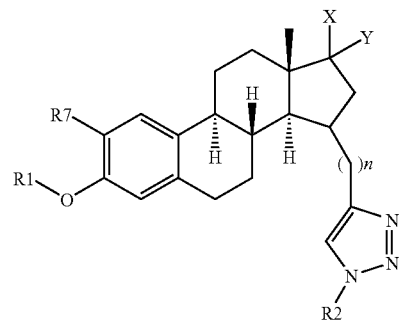
(Iy)

In one embodiment, the present invention relates to a compound of the general formula I, which is an optically pure 15β enantiomer having the formula (Ia)

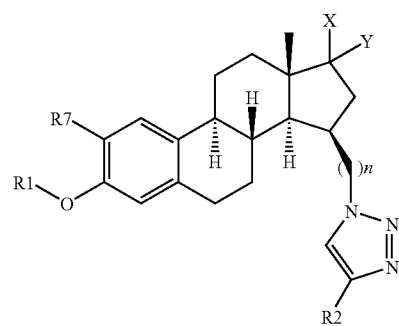
(Ia)

wherein R1, R2 and R7 are as defined herein, and/or physiologically compatible salts, and/or solvates, and/or prodrugs thereof. In a further embodiment, the present invention relates to the 15β enantiomer having formula (Ia), wherein n represents 2, 3, 4, 5 or 6.

In another embodiment, the present invention relates to a compound of the general formula I, which is an optically pure 15α enantiomer having the formula (Ib)

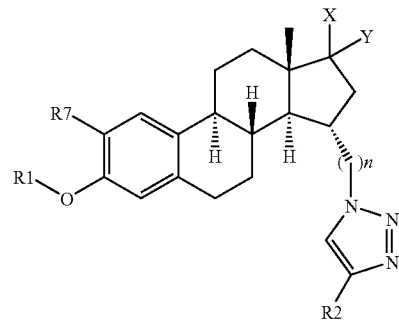
(Ib)

wherein R1, R2 and R7 are as defined herein, and/or physiologically compatible salts, and/or solvates, and/or prodrugs thereof. In a further embodiment, the present invention relates to the 15α enantiomer having formula (Ib), wherein n represents 3.

In another embodiment, the present invention relates to a compound of the general formula I, which is an optically pure 15β enantiomer having the formula (Ic)

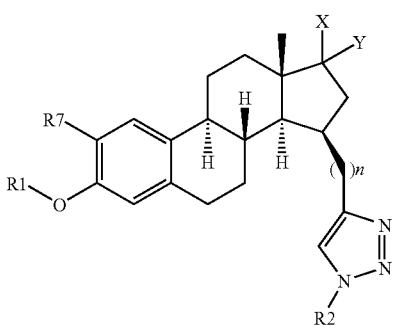

(Ic)

wherein R1, R2 and R7 are as defined herein, and/or physiologically compatible salts, and/or solvates, and/or prodrugs thereof. In a further embodiment, the present invention relates to the 15β enantiomer having formula (Ib), wherein n represents 3.

In another embodiment, the present invention relates to a compound of the general formula I, which is an optically pure 15α enantiomer having the formula (Id)

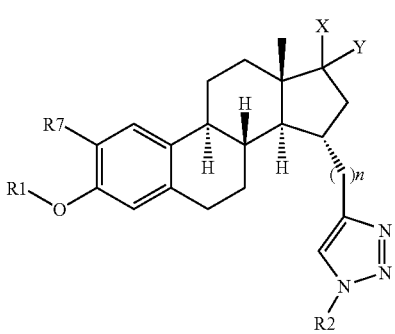

(Id)

wherein R1, R2 and R7 are as defined herein, and/or physiologically compatible salts, and/or solvates, and/or prodrugs thereof. In a further embodiment, the present invention relates to the 15α enantiomer having formula (Ib), wherein n represents 3 or 4.

In one embodiment, the invention relates to compounds of formula I which are selected from the group consisting of
3-Hydroxy-15β-[2-(4-phenethyl-[1,2,3]triazol-1-yl)-ethyl]-estra-1,3,5(10)-trien-17-one
3-Hydroxy-15β-{2-[4-(3-hydroxy-phenyl)-[1,2,3]triazol-1-yl]-ethyl}-estra-1,3,5(10)-trien-17-one
3-Hydroxy-15β-{2-[4-(2,4-difluoro-phenyl)-[1,2,3]triazol-1-yl]-ethyl}-estra-1,3,5(10)-trien-17-one
3-Hydroxy-15β-{2-[4-(3-methyl-butyl)-[1,2,3]triazol-1-yl]-ethyl}-estra-1,3,5(10)-trien-17-one
3-Hydroxy-15β-{2-[4-(3,5-difluoro-phenyl)-[1,2,3]triazol-1-yl]-ethyl}-estra-1,3,5(10)-trien-17-one
3-Hydroxy-15β-[2-(4-cyclohexylmethyl-[1,2,3]triazol-1-yl)-ethyl]-estra-1,3,5(10)-trien-17-one
3-Hydroxy-15β-{2-[4-(2-fluoro-phenyl)-[1,2,3]triazol-1-yl]-ethyl}-estra-1,3,5(10)-trien-17-one
3-Hydroxy-15β-[3-(4-phenethyl-[1,2,3]triazol-1-yl)-propyl]-estra-1,3,5(10)-trien-17-one
3-Hydroxy-15β-{2-[4-(3-trifluoromethyl-phenyl)-[1,2,3]triazol-1-yl]-ethyl}-estra-1,3,5(10)-trien-17-one
3-Hydroxy-15β-{2-[4-(4-trifluoromethyl-phenyl)-[1,2,3]triazol-1-yl]-ethyl}-estra-1,3,5(10)-trien-17-one
3-Hydroxy-15β-{2-[4-(4-methoxy-phenyl)-[1,2,3]triazol-1-yl]-ethyl}-estra-1,3,5(10)-trien-17-one
3-Hydroxy-15β-[2-(4-iso-butyl-[1,2,3]triazol-1-yl)-ethyl]-estra-1,3,5(10)-trien-17-one
3-Hydroxy-15β-{2-[4-(4-trifluoromethoxy-phenyl)-[1,2,3]triazol-1-yl]-ethyl}-estra-1,3,5(10)-trien-17-one
3-Hydroxy-15α-[3-(4-phenethyl-[1,2,3]triazol-1-yl)-propyl]-estra-1,3,5(10)-trien-17-one
3-Hydroxy-15β-{3-[4-(3-methyl-butyl)-[1,2,3]triazol-1-yl]-propyl}-estra-1,3,5(10)-trien-17-one
3-Hydroxy-15β-{3-[4-(3,5-difluoro-phenyl)-[1,2,3]triazol-1-yl]-propyl}-estra-1,3,5(10)-trien-17-one
3-Hydroxy-15β-{2-[4-(2-trifluoromethyl-phenyl)-[1,2,3]triazol-1-yl]-ethyl}-estra-1,3,5(10)-trien-17-one
3-Hydroxy-15α-{3-[4-(4-methoxy-phenyl)-[1,2,3]triazol-1-yl]-propyl}-estra-1,3,5(10)-trien-17-one
3-Hydroxy-15β-[3-(4-cyclohexylmethyl-[1,2,3]triazol-1-yl)-propyl]-estra-1,3,5(10)-trien-17-one
3-Hydroxy-15α-{3-[4-(3-hydroxy-phenyl)-[1,2,3]triazol-1-yl]-propyl}-estra-1,3,5(10)-trien-17-one
3-Hydroxy-15β-[3-(4-iso-butyl-[1,2,3]triazol-1-yl)-propyl]-estra-1,3,5(10)-trien-17-one
3-Hydroxy-15α-[3-(4-p-tolyl-[1,2,3]triazol-1-yl)-propyl]-estra-1,3,5(10)-trien-17-one
3-Hydroxy-15β-{3-[4-(2,4-difluoro-phenyl)-[1,2,3]triazol-1-yl]-propyl}-estra-1,3,5(10)-trien-17-one
3-Hydroxy-15α-{3-[4-(3-methyl-butyl)-[1,2,3]triazol-1-yl]-propyl}-estra-1,3,5(10)-trien-17-one
3-Hydroxy-15α-[3-(4-iso-butyl-[1,2,3]triazol-1-yl)-propyl]-estra-1,3,5(10)-trien-17-one
3-Hydroxy-15β-{3-[4-(4-trifluoromethoxy-phenyl)-[1,2,3]triazol-1-yl]-propyl}-estra-1,3,5(10)-trien-17-one
4-{1-[3-(3-Methoxy-15β-17-oxo-estra-1,3,5(10)-trien-15-yl)-propyl]-1H-[1,2,3]triazol-4-yl}-benzoic acid methyl ester
15β-{3-[1-(2,4-difluorophenyl)-1H-1,2,3-triazol-4-yl]propyl}-3-hydroxyestra-1(10), 2,4-trien-17-one
15β-[3-(1-butyl-1H-1,2,3-triazol-4-yl)propyl]-3-hydroxyestra-1(10), 2,4-trien-17-one
15β-{3-[1-(2,4-difluorophenyl)-1H-1,2,3-triazol-4-yl]propyl}-17,17-difluoroestra-1(10), 2,4-trien-3-ol
and/or physiologically compatible salts, and/or solvates, and/or prodrugs thereof.

According to another aspect, the invention relates to a process to prepare the compounds of the invention of formula I

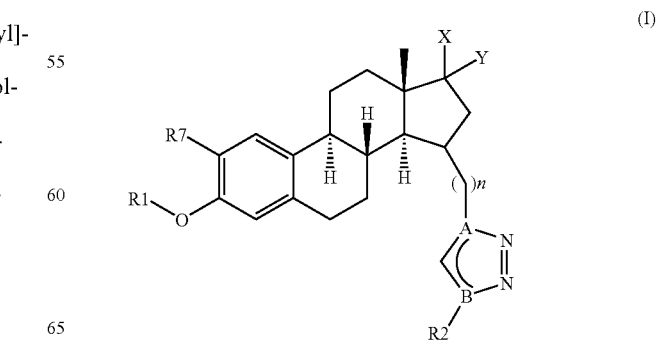

(I)

wherein
A represents N and B represents C
n represents 1, 2, 3, 4, 5 or 6
X, Y individually represent F, or X and Y together represent =O
$R^1$ is selected from the group consisting of:
- (a) —H,
- (b) —$(C_1-C_6)$alkyl, which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$OR^3$, —$SR^3$ or —$COOR^3$ moieties,
  - or which is optionally substituted by aryl, in which the aryl moiety is optionally substituted by 1 or 2 substituents selected from the group consisting of halogen, hydroxyl or —$(C_1-C_6)$alkyl, and
- (c) -phenyl, which is optionally substituted by halogen, carbonitril, —$OR^3$, —$SR^3$, —$COOR^3$, or —$(C_1-C_6)$alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —$(C_1-C_6)$alkyl moieties,
  wherein each $R^3$ is independently selected from the group consisting of H, —$(C_1-C_6)$alkyl, optionally substituted by 1, 2 or 3 halogens and/or optionally substituted by 1, 2 or 3 hydroxyl moieties; and aryl, optionally substituted by 1, 2 or 3 halogens, $R^2$ is selected from the group consisting of:
- (a) —$(C_1-C_8)$alkyl,
  which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
- (b) aryl or aryl-$(C_1-C_8)$alkyl,
  in which the aryl moiety may be monocyclic or bicyclic; and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties;
  and in which the alkyl moiety is optionally substituted by 1, 2 or 3 halogens;
- (c) heteroaryl or heteroaryl-$(C_1-C_8)$alkyl,
  in which the heteroaryl moiety contains one, two or three heteroatoms independently selected from the group consisting of N, O or S, the number of N atoms being 0, 1, 2 or 3, and the number of O and S atoms each being 0, 1 or 2,
  and which heteroaryl moiety is optionally substituted by halogen, carbonitril, nitro, —$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ or —$COR^4$ moieties,
  and in which the alkyl moiety is optionally substituted by 1, 2 or 3 halogens;
- (d) $(C_3-C_8)$cycloalkyl or $(C_3-C_8)$cycloalkyl-$(C_1-C_8)$alkyl,
  in which the cycloalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties,
- (e) cycloheteroalkyl or cycloheteroalkyl-$(C_1-C_8)$alkyl,
  in which the cycloheteroalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties; and
- (f) —$(C_1-C_8)$alkanoyl wherein
each $R^4$ and $R^5$ is independently selected from the group consisting of H, —$(C_1-C_6)$alkyl, optionally substituted by 1, 2 or 3 halogens and/or optionally substituted by 1, 2 or 3 hydroxyl moieties; and aryl and aryl-$(C_1-C_6)$alkyl, optionally substituted in the aryl moiety by 1, 2 or 3 halogens, or
$R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and
$R^6$ represents —$(C_1-C_6)$alkyl, which is optionally substituted by 1, 2 or 3 halogens and/or optionally substituted by 1, 2 or 3 hydroxyl moieties;

$R^7$ is selected from the group consisting of
- (a) H,
- (b) $(C_1-C_4)$alkyl,
- (c) $(C_1-C_4)$alkoxy, and
- (d) $(C_1-C_4)$alkoxy-$(C_1-C_4)$alkyl moiety, and/or all stereoisomers, and/or physiologically compatible salts, and/or metabolites, and/or solvates, and/or prodrugs thereof, characterized in that
a compound of general formula XII

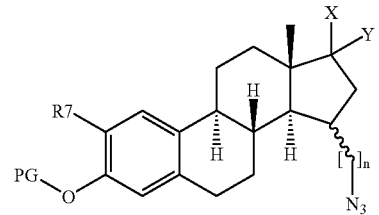

(XII)

wherein X, Y, $R^7$ and n have the meanings as defined above and PG is a common protecting group,
is reacted by a copper catalyzed coupling with a terminal alkine of formula A,

(A)

wherein $R^2$ has the meanings as defined above,
wherein different copper sources are used, selected from the group consisting of copper sources wherein copper has the oxidation states 0, I or II, and
wherein the protecting group is replaced after the coupling reaction by $R^1$, which has the meaning as defined above.

According to another aspect, the invention relates to a process to prepare the compounds of the invention of formula (Ic)

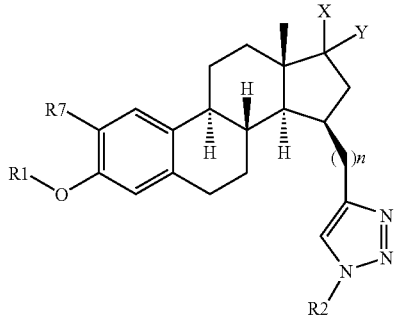

wherein
n represents 1, 2, 3, 4, 5 or 6
X, Y individually represent F, or X and Y together represent =O
$R^1$ is selected from the group consisting of:
(d) —H,
(e) —($C_1$-$C_6$)alkyl, which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$OR^3$, —$SR^3$ or —$COOR^3$ moieties,
or which is optionally substituted by aryl, in which the aryl moiety is optionally substituted by 1 or 2 substituents selected from the group consisting of halogen, hydroxyl or —($C_1$-$C_6$)alkyl, and
(f) -phenyl, which is optionally substituted by halogen, carbonitril, —$OR^3$, —$SR^3$, —$COOR^3$, or —($C_1$-$C_6$)alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —($C_1$-$C_6$)alkyl moieties,
wherein each $R^3$ is independently selected from the group consisting of H, —($C_1$-$C_6$)alkyl, optionally substituted by 1, 2 or 3 halogens and/or optionally substituted by 1, 2 or 3 hydroxyl moieties; and aryl, optionally substituted by 1, 2 or 3 halogens,
$R^2$ is selected from the group consisting of:
(g) —($C_1$-$C_8$)alkyl,
which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
(h) aryl or aryl-($C_1$-$C_8$)alkyl,
in which the aryl moiety may be monocyclic or bicyclic; and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties;
and in which the alkyl moiety is optionally substituted by 1, 2 or 3 halogens;
(i) heteroaryl or heteroaryl-($C_1$-$C_8$)alkyl,
in which the heteroaryl moiety contains one, two or three heteroatoms independently selected from the group consisting of N, O or S, the number of N atoms being 0, 1, 2 or 3, and the number of O and S atoms each being 0, 1 or 2,
and which heteroaryl moiety is optionally substituted by halogen, carbonitril, nitro, —$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ or —$COR^4$ moieties,
and in which the alkyl moiety is optionally substituted by 1, 2 or 3 halogens;
(j) ($C_3$-$C_8$)cycloalkyl or ($C_3$-$C_8$)cycloalkyl-($C_1$-$C_8$)alkyl,
in which the cycloalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties,
(k) cycloheteroalkyl or cycloheteroalkyl-($C_1$-$C_8$)alkyl,
in which the cycloheteroalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties; and
(l) —($C_1$-$C_8$)alkanoyl
wherein
each $R^4$ and $R^5$ is independently selected from the group consisting of H, —($C_1$-$C_6$)alkyl, optionally substituted by 1, 2 or 3 halogens and/or optionally substituted by 1, 2 or 3 hydroxyl moieties; and aryl and aryl-($C_1$-$C_6$)alkyl, optionally substituted in the aryl moiety by 1, 2 or 3 halogens, or
$R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N
atoms being 0, 1 or 2 and the number of O and S atoms each being 0, 1 or 2, or which ring optionally contains a sulfoxide moiety in addition to the nitrogen atom, and
$R^6$ represents —($C_1$-$C_6$)alkyl, which is optionally substituted by 1, 2 or 3 halogens and/or optionally substituted by 1, 2 or 3 hydroxyl moieties;
$R^7$ is selected from the group consisting of
(e) H,
(f) ($C_1$-$C_4$)alkyl,
(g) ($C_1$-$C_4$)alkoxy, and
(h) ($C_1$-$C_4$)alkoxy-($C_1$-$C_4$)alkyl moiety,
and/or all stereoisomers, and/or physiologically compatible salts, and/or metabolites, and/or solvates, and/or prodrugs thereof, characterized in that a compound of general formula (XXXII-Ia)

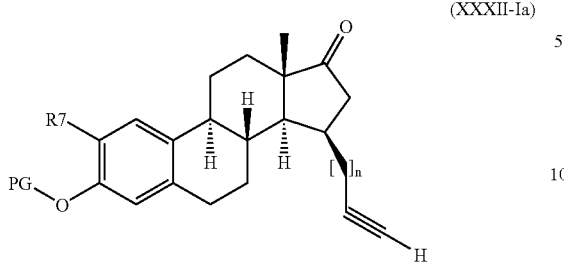

(XXXII-Ia)

wherein $R^7$ and n have the meanings as defined above and PG is a common protecting group,
is reacted by a Cu (I)-catalyzed coupling in the presence of an azide (e.g. NaN3) with a halide of formula B,

(B)

wherein $R^2$ has the meanings as defined above,
wherein a modification of the $C_{17}$ keto group affords compounds of formula (Ic) with X, Y=F, and
wherein the protecting group is replaced after the coupling reaction by $R^1$, which has the meaning as defined above.

According to another aspect, the invention relates to a process to prepare the compounds of the invention of formula (Id)

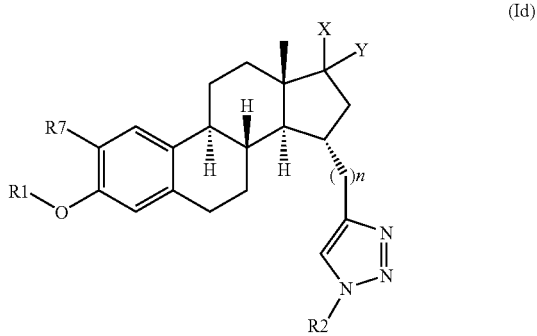

(Id)

wherein
n represents 3, or 4
X, Y individually represent F, or X and Y together represent =O
$R^1$ is selected from the group consisting of:
(g) —H,
(h) —$(C_1$-$C_6)$alkyl, which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$OR^3$, —$SR^3$ or —$COOR^3$ moieties,
or which is optionally substituted by aryl, in which the aryl moiety is optionally substituted by 1 or 2 substituents selected from the group consisting of halogen, hydroxyl or —$(C_1$-$C_6)$alkyl, and
(i) -phenyl, which is optionally substituted by halogen, carbonitril, —$OR^3$, —$SR^3$, —$COOR^3$, or —$(C_1$-$C_6)$ alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —$(C_1$-$C_6)$alkyl moieties,
wherein each $R^3$ is independently selected from the group consisting of H, —$(C_1$-$C_6)$alkyl, optionally substituted by 1, 2 or 3 halogens and/or optionally substituted by 1, 2 or 3 hydroxyl moieties; and aryl, optionally substituted by 1, 2 or 3 halogens,
$R^2$ is selected from the group consisting of:
(m) —$(C_1$-$C_8)$alkyl,
which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
(n) aryl or aryl-$(C_1$-$C_8)$alkyl,
in which the aryl moiety may be monocyclic or bicyclic;
and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties;
and in which the alkyl moiety is optionally substituted by 1, 2 or 3 halogens;
(o) heteroaryl or heteroaryl-$(C_1$-$C_8)$alkyl,
in which the heteroaryl moiety contains one, two or three heteroatoms independently selected from the group consisting of N, O or S, the number of N atoms being 0, 1, 2 or 3, and the number of O and S atoms each being 0, 1 or 2,
and which heteroaryl moiety is optionally substituted by halogen, carbonitril, nitro, —$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ or —$COR^4$ moieties,
and in which the alkyl moiety is optionally substituted by 1, 2 or 3 halogens;
(p) $(C_3$-$C_8)$cycloalkyl or $(C_3$-$C_8)$cycloalkyl-$(C_1$-$C_8)$alkyl,
in which the cycloalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties,
(q) cycloheteroalkyl or cycloheteroalkyl-$(C_1$-$C_8)$alkyl,
in which the cycloheteroalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$, or —$COR^4$ moieties; and
(r) —$(C_1$-$C_8)$alkanoyl
wherein
each $R^4$ and $R^5$ is independently selected from the group consisting of H, —$(C_1$-$C_6)$alkyl, optionally substituted by 1, 2 or 3 halogens and/or optionally substituted by 1, 2 or 3 hydroxyl moieties; and aryl and aryl-$(C_1-C_6)$alkyl, optionally substituted in the aryl moiety by 1, 2 or 3 halogens, or $R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and $R^6$ represents —$(C_1-C_6)$alkyl, which is optionally substituted by 1, 2 or 3 halogens and/or optionally substituted by 1, 2 or 3 hydroxyl moieties;

$R^7$ is selected from the group consisting of
(i) H,
(j) $(C_1-C_4)$alkyl,
(k) $(C_1-C_4)$alkoxy, and
(l) $(C_1-C_4)$alkoxy-$(C_1-C_4)$alkyl moiety, and/or all stereoisomers, and/or physiologically compatible salts, and/or metabolites, and/or solvates, and/or prodrugs thereof, characterized in that a compound of general formula (XXXII-Ib)

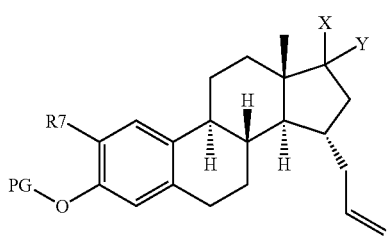

(XXXII-Ib)

wherein $R^7$ has the meanings as defined above and PG is a common protecting group,
is reacted with a triazole allyl compound of formula C,

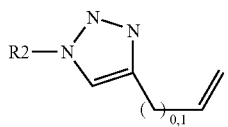

(C)

wherein $R^2$ has the meanings as defined above,
wherein a modification of the $C_{17}$ keto group affords compounds of formula (Id) with X, Y=F, and
wherein the protecting group is replaced after the coupling reaction by $R^1$, which has the meaning as defined above.

Additionally, the invention relates to a compound of the invention for use as a medicament.

In another aspect, a pharmaceutical composition, containing a pharmacologically active quantity of a compound of formula (I) as defined herewithin and conventional auxiliaries and/or carriers is described.

According another aspect, the invention concerns the use of a compound of formula (I), as defined herein, for the treatment or prevention of a steroid hormone dependent disease or disorder in a mammal, in particular a human. In addition, the invention relates to the use of a compound of the invention for the manufacture of a medicament for the treatment or prevention of a steroid hormone dependent disease or disorder in a mammal, in particular a human. Preferably, the steroid hormone dependent disease or disorder is a disease or disorder requiring the inhibition of a 17β-hydroxysteroid dehydrogenase enzyme, preferably of the 17β-HSD type 1, 17β-HSD type 2 or 17β-HSD type 3. Preferably the steroid hormone dependent disease or disorder is an estradiol dependent disease or disorder. Alternatively, the steroid dependent disease or disorder is an androgen-dependent disease or disorder.

Furthermore, the invention also relates to a method of treating a mammal such as a human having a condition related to 17β-hydroxysteroid dehydrogenase enzyme activity, preferably 17β-HSD1, 17β-HSD2 or 17β-HSD3 activitym, or which condition can be treated by inhibition of one of said enzymes, comprising administering to the mammal an amount of a compound of this invention, or a salt or a prodrug thereof, which amount is effective to treat the condition. Administration of compounds of this invention in combination with other pharmaceuticals used in treatment of the listed conditions is contemplated.

The conditions to be treated include but are not limited to malign estradiol dependent diseases or disorders such as breast cancer, ovarian cancer, uterine cancer, endometrial cancer, and endometrial hyperplasia. Preferably, the malign disease or disorder is characterized by a detectable level of 17β-HSD1 expression within a cancer tissue sample. A detectable level of 17β-HSD1 expression means that a certain level of 17β-HSD1 mRNA or of 17β-HSD1 protein can be detected by conventional molecular biology methods such as hybridization, PCR reactions, Northern or Western Blotting etc. An alternative detection method for 17β-HSD1 expression is the measurement of the corresponding enzyme activity.

According to a further aspect of the invention, the estradiol dependent disease is breast cancer and the mammal is a human post-menopausal female.

Furthermore, the conditions to be treated include but are not limited to benign estradiol dependent diseases or disorders such as endometriosis, uterine fibroids, uterine leiomyoma, adenomyosis, dysmenorrhea, menorrhagia, metrorrhagia, and urinary dysfunction.

In a further embodiment, the invention relates to use of an effective amount of a compound of the invention for the treatment or prevention of one of the aforementioned benign gynaecological diseases or disorders in a mammal whereby the mammal is a human, preferably a female and most preferably a pre- or peri-menopausal female.

According to a further aspect of the present invention, the steroid hormone dependent disease or disorder is an androgen-dependent disease or disorder. Preferably, said androgen-dependent disease or disorder is selected from the group consisting of prostate cancer, prostadynia, benign prostatic hyperplasia, urinary dysfunction, lower urinary tract syndrome, acne, seborrhea, androgenetic alopecia, hirsutism, precocious puberty, adrenal hyperplasia, polycystic ovarian syndrome and prostatitis.

According to a further aspect of the invention, the steroid hormone dependent disease or disorder to be treated is an estrogen- or androgen dependent disease or disorder requiring the lowering of the endogeneous estrogen or androgen concentration in a generalized or tissue-specific manner.

Therefore, further steroid-dependent diseases which may be treated with an effective amount of a compound of the invention are selected from the group consisting of squamous cell carcinoma, colon cancer, osteoporosis, rheumatoid arthritis, type I and II diabetes, systemic lupus erythematosus, multiple sclerosis, myastenia gravis, thyroiditis, vasculitis, ulcerative colitis, Crohn's disease, psoriasis, contact dermatitis, graft versus host and host versus graft disease (organ rejection following transplantation), eczema, asthma, tissue wounds, skin wrinkles and cataracts.

Additionally, the compounds of the invention might be useful for blocking spermatogenesis and as an anti-fertility agent for males.

According to a further embodiment, a compound of the present invention may be used for the enhancement of cognitive function, i.e. in the treatment or prevention of cognitive dysfunctions, such as senile dementia, including Alzheimer's disease.

The disclosed compounds are also useful as diagnostic agents (e.g. in diagnostic kits or for use in clinical laboratories) for screening for the presence or absence of 17β-HSD1, 17β-HSD2 and/or 17β-HSD3 enzyme activity.

Some Advantages

One key advantage of the present invention is that the compounds of the present invention can act as selective 17β-HSD1, 17β-HSD2 or 17β-HSD3 inhibitors. Another advantage of the compounds of the present invention is that they may be potent in vivo and suited for the therapeutic use in mammals, especially humans. Some of the compounds of the present invention may be non-estrogenic compounds. Here, the term "non-estrogenic" means exhibiting no or substantially no estrogenic activity on the estrogen receptor. Another advantage is that some of the compounds may not be capable of being metabolised to compounds which display or induce hormonal activity. Some of the compounds of the present invention are also advantageous in that they may be orally active.

DETAILED DESCRIPTION OF THE INVENTION

Definitions

The following terms are used to describe various constituents of the chemical composition useful in this invention. The terms are defined as follows:

As used herein, the terms "comprising" and "including" are used herein in their open, non-limiting sense.

The word "compound" shall here be understood to cover any and all isomers (e.g., enantiomers, stereoisomers, diastereomers, rotomers, and tautomers), racemates or any mixture of isomers, prodrugs, and any pharmaceutically acceptable salt of said compound, unless the formula depicting the compound explicitly shows a particular stereochemistry.

Where the plural form is used for compounds, salts, and the like, this is taken to mean also a single compound, salt, or the like.

The term "17β-hydroxysteroid dehydrogenase type I" or "17β-HSD1" for short is used for the enzyme EC 1.1.1.62 and reduces estrone (E1) to the biologically active estrogen, estradiol (E2).

The terms "inhibit" and "inhibition" include the meaning of to reduce and/or eliminate and/or mask and/or prevent a certain enzyme action.

The term "17β-HSD1 inhibitor" as used herein with respect to the compound of the present invention means a compound that can inhibit 17β-HSD1 activity, such as to reduce and/or eliminate and/or mask and/or prevent the action of 17β-HSD1. The 17β-HSD1 inhibitor may act as a reversible or irreversible inhibitor of 17β-HSD1. The ability of compounds to inhibit 17β-HSD1 activity can be assessed using cell lines recombinantly expressing the human 17β-HSD1 enzyme. Details on a suitable Assay Protocol are presented in the Examples section. It is to be noted that the compound of the present invention may have other beneficial properties in addition to or in the alternative to its ability to inhibit 17β-HSD1 activity; in particular a 17β-HSD1 inhibitor may have antagonistic activity towards the nuclear estrogen receptor.

The terms "selective" and "selectivity" as used herein with respect to the compounds of the present invention means a compound that can inhibit 17β-HSD1, 17β-HSD2 and/or 17β-HSD3 activity, and shows a higher inhibition value for these particular targets than with regard to other enzyme targets, in particular with regard to the 17β-HSD1 enzyme, and that has weak or no affinity for nuclear receptors, in particular that has weak or no affinity for the ER. Preferably a compound of the present invention has at least about a 100 fold selectivity to a desired target (e.g. 17β-HSD1), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

The term "substituted" means that the specified group or moiety bears one or more substituents. Where any group may carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents.

Any asymmetric carbon atoms may be present in the (R)-, (S)- or (R,S)-configuration preferably in the (R)- or (S)-configuration, whichever is most active, unless the stereochemistry is explicitly depicted in the corresponding compound formula. Substituents at a double bond or a ring may be present in cis (=Z—) or trans (=E-) form, unless the stereochemistry is explicitly depicted in the corresponding compound formula.

The compounds of formula I have a defined stereochemistry within the steroidal core structure according to the natural configuration for estrogenic steroids such as estradiol:

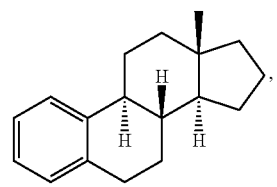

The stereochemistry within the steroidal core structure is always shown in the corresponding compound formula and should not vary within the scope of the present invention, whereas the stereochemistry at the carbon atoms in the steroidal core carrying additional side chains and the stereochemistry of any asymmetric carbon atom within the side chains themselves is not fixed. Therefore, the term "compounds of formula I" or "compounds of formula II" etc also comprises the stereoisomers of the depicted compounds, unless a particular stereochemistry is explicitly shown within the formula. The stereochemistry shown in the respective formula prevails over the general term "stereoisomers".

The compounds of the formula I contain at least one additional chiral carbon atom, namely the carbon atom carrying the side chain in the 15-position of the steroid structure. The compounds can thus be present at least in two optically active stereoisomeric forms or as a racemate. The present invention includes both the racemic mixtures and the isomerically pure compounds of the formula I. The position of the substituents within the C15 position is characterized by α or β. A C15β derivative according to the present invention is represented by a compound of the following formulae (Ia) and (Ic)

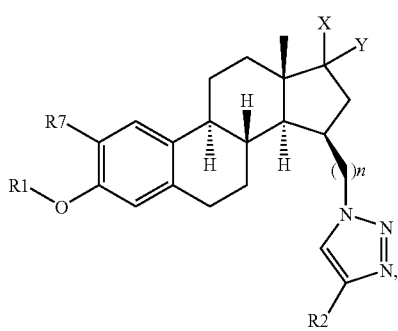

(Ia)

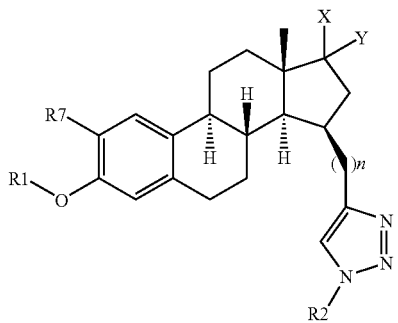

(Ic)

whereas a C15α derivative according to the present invention is represented by a compound of the following formulae (Ib) and (Id)

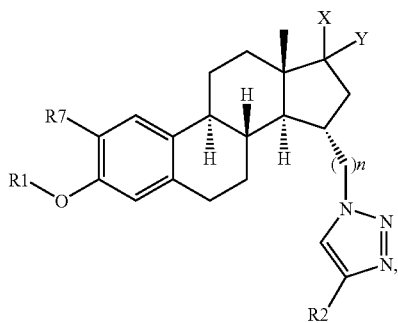

(Ib)

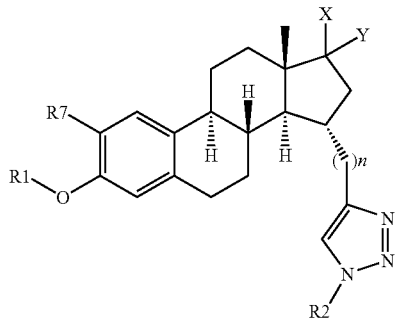

(Id)

The compounds of the present invention may contain further asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention, unless a particular stereochemistry is explicitly depicted in the formula representing a respective compound.

The term "halogen" refers to fluorine, bromine, chlorine, and iodine atoms. Preferred in the context of the present invention are F, Cl and Br.

The terms "dihalogen", "trihalogen" and "perhalo" refer to two, three and four halogen substituents, respectively, each individually selected from the group consisting of fluorine, bromine, chlorine, and iodine atoms.

For the purpose of the present invention, the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus $C_1$-$C_4$-alkyl refers to alkyl of 1-4 carbon atoms, inclusive, or methyl, ethyl, propyl, butyl and isomeric forms thereof.

The term "alkyl" stands for a hydrocarbon radical which may be linear or branched, with single or multiple branching, whereby the alkyl group comprises the number of carbon atoms as indicated by the prefix. The term ($C_1$-$C_8$)alkyl is exemplified by such groups as methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl, heptyl, octyl and the like. The alkyl or ($C_1$-$C_8$)alkyl group may be partially unsaturated, forming such groups as, for example, vinyl, propenyl (allyl), butenyl, pentenyl, pentinyl, hexenyl, octadienyl, and the like.

The term "cyclo($C_3$-$C_8$)alkyl" comprises cyclopropyl, cyclobutyl, cyclopentyl, cyclohexyl, cycloheptyl, cyclooctyl and isomeric forms thereof such as methylcyclopropyl; 2- or 3-methylcyclobutyl; 2-, or 3-methylcyclopentyl, and the like. The "cycloalkyl" group may also be partly unsaturated, forming such groups as, for example, cyclohexenyl, cyclopentenyl, cyclooctadienyl, and the like. Furthermore, the term "cyclo($C_3$-$C_8$)alkyl-($C_1$-$C_4$)alkyl" which refers to a alkyl group of 1 to 4 carbon atoms as described above substituted with a cyclo($C_3$-$C_8$)alkyl group as described above, comprises such groups as for example cyclopropylmethyl, cyclohexylmethyl, cyclopentylethyl or cyclohexenylethyl.

The term "(C$_1$-C$_4$)alkoxy" refers to a group —O—(C$_1$-C$_4$) alkyl with the (C$_1$-C$_4$)alkyl group as defined above.

The term "amino" refers to a group —NRR', wherein R and R' are residues as particularly defined herein.

The term "amido" refers to a group —(C=O)—NRR', wherein R and R' are residues as particularly defined herein.

The term "alkanoyl" refers to a group —(C=O)-alkyl. Preferably alkanoyl is —(C$_1$-C$_8$)alkanoyl referring to a group —(C=O)—(C$_1$-C$_8$)alkyl, with —(C$_1$-C$_8$)alkyl as defined herewithin. More preferred alkanoyl is —(C$_1$-C$_4$)alkanoyl referring to a group —(C=O)—(C$_1$-C$_4$)alkyl, with —(C$_1$-C$_4$)alkyl as defined herewithin.

The term "acyl" refers to a group —(C=O)—R, also depicted as —COR, wherein R is a residue as particularly defined herein.

The term "carboxyl" refers to a group —(C=O)—O—R, also depicted as —COOR, wherein R is a residue as particularly defined herein.

The term "aryl" refers to an aromatic carbocyclic group comprising 6 to 14, more preferably 6 to 10, carbon atoms and having at least one aromatic ring or multiple condensed rings in which at least one ring is aromatic. Preferably, aryl is phenyl, naphthyl, indanyl, indenyl, fluorenyl, 1,2,3,4-tetrahydro-naphthalen-1-yl or even biphenyl. Additionally, the term "aryl" includes benzyl.

The term "arylalkyl" refers to an alkyl group substituted with up to three independently selected aryl groups; preferably the term "arylalkyl" refers to "aryl-(C$_1$-C$_8$)-alkyl" or aryl-(C$_1$-C$_4$)-alkyl, whereby the aryl is an aryl group as defined above. Aryl-(C$_1$-C$_4$)alkyl is preferably benzyl (—CH$_2$-phenyl) or phenethyl (—CH$_2$—CH$_2$-phenyl).

The term "cycloheteroalkyl" refers to a four- to eight-membered heterocyclic ring containing at least one heteroatom, such as N, O or S, the number of N atoms being 0, 1, 2 or 3 and the number of O and S atoms each being 0, 1 or 2, which system may be saturated, partly unsaturated or hydroaromatic, and which ring can be part of a multiple condensed ring-system in which some rings may be aromatic. Examples of such cycloheteroalkyls include pyrrolidinyl, tetrahydrofuryl, tetrahydrothiophenyl, tetrahydropyridinyl, azetidinyl, thiazolidinyl, oxazolidinyl, piperidinyl, morpholinyl, thiomorpholinyl, piperazinyl, azepanyl, diazepanyl, oxazepanyl, thiazepanyl, dihydro-1H-pyrrolyl, 3,6-dihydro-2H-pyridinyl, 1,3-dihydro-benzoimidazolyl and the like. Preferred examples of such cycloheteroalkyl groups are pyrrolidinyl, morpholinyl, tetrahydrofuryl, piperidinyl or azepanyl. The cycloheteroalkyl group may optionally be substituted, whereby the substituents may be attached to any carbon or nitrogen atom of the cycloheteroalkyl moiety.

The term "heteroaryl" refers to an aromatic carbocyclic group of having a single 4 to 8 membered ring or multiple condensed rings comprising 6 to 14, more preferably 6 to 10, ring atoms and containing at least one heteroatom, such as N, O or S, within at least one ring, the number of N atoms being 0, 1, 2 or 3 and the number of O and S atoms each being 0, 1 or 2; in which group at least one heterocyclic ring is aromatic. Examples of such groups include pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, indolyl, quinolinyl, isoquinolinyl, benzothiazolyl, benzoimidazolyl, 1,3-dihydro-benzoimidazolyl, benzofuran, benzo[b]thiophene and the like. Preferably, heteroaryl is quinolinyl, furyl, benzoimidazolyl, pyridinyl, thienyl, indolyl, benzo[b]thiophene, pyridinyl, imidazolyl, pyrazolyl or thiazolyl.

The statement is made that when two side chains are found on a single N, they can be combined, including the N to which they are attached, into a heterocyclic ring of 5-, 6-, 7- or 8 atoms, which can be saturated or contain one or more double bonds between the ring atoms, and which ring can optionally contain 1 or 2 additional heteroatoms selected from the group consisting of N, O or S, the number of additional N atoms being 0, 1 or 2 and the number of O and S atoms each being 0, 1 or 2, or which ring optionally contains a sulfoxide moiety in addition to the nitrogen atom; and which ring can be part of a multiple condensed ring-system, in which some rings may be aromatic. Preferred examples of such ring systems, including the N, to which the respective side chains are attached, comprise:

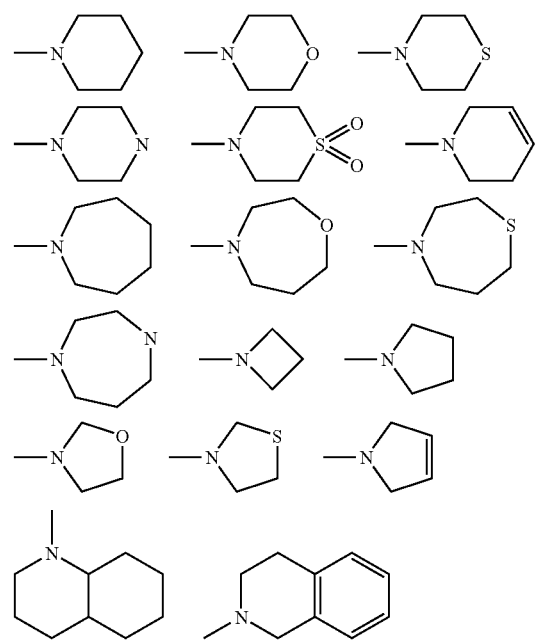

The following table lists terms and the specific structural group to which they refer.

TABLE 1

| description of specific structural groups | |
|---|---|
| TERM | GROUP |
| hydroxyl | —OH |
| sulfoxide | [S(=O)$_2$ group] |
| carbonitril | —CN |
| formyl | [CHO group] |
| phenyl | [phenyl ring] |
| naphthyl | [naphthyl ring] |

TABLE 1-continued description of specific structural groups

| TERM | GROUP |
|---|---|
| benzenesulfonyloxy | 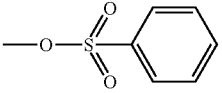 |
| benzylmethylamino | 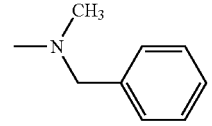 |
| dimethylamino | —N(CH$_3$)$_2$ |
| acetyl |  |
| cyclohexyl |  |
| dioxothiomorpholin-4-yl | 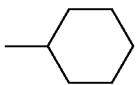 |
| methoxy | —O—CH$_3$ |
| hydroxymethyl | —CH$_2$—OH |
| methoxycarbonyl |  |
| nitro |  |
| trihalomethoxy | —O—CX$_3$ with X =F, Cl, Br, I |
| trihalomethyl | —CX$_3$ with X =F, Cl, Br, I |
| pyridine-2-yl |  |
| benzyl | 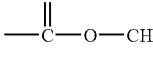 |
| pyridine-3-yl |  |
| pyridine-4-yl | 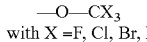 |
| imidazol-4-yl | 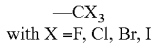 |
| cyclopropyl | 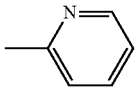 |

TABLE 1-continued description of specific structural groups

| TERM | GROUP |
|---|---|
| cyclopentyl | 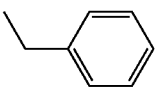 |
| fur-2-yl | 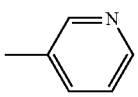 |
| fur-3-yl | 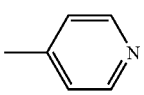 |
| thiophen-2-yl | 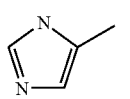 |
| thiophen-3-yl |  |
| cyclohexylmethyl | 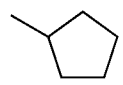 |

The term "pro-drug" as used herein, represents derivatives of the compounds of the invention that are drug precursors which, following administration to a patient by any known route, release the drug in vivo via a chemical or physiological process. As used herein, the term "pro-drug" include metabolic precursors. Pro-drugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Pro-drugs as therapeutics", P. Ettmayer et al., Expert Opin. Ther. Patents, 14(3), 277-280, 2004, "Lessons learned from marketed and investigational pro-drugs", J. Med. Chem., 47, 2393-2404, 2004). In particular, pro-drugs are derivatives of the compounds of the invention in which functional groups carry additional substituents which may be cleaved under physiological conditions in vivo and thereby releasing the active principle of the compound (e.g., a pro-drug on being brought to a physiological pH or through an enzyme action is converted to the desired drug form). Pro-drugs of the compounds mentioned above are also within the scope of the present invention. Pro-drugs that are metabolised to compounds having formula (I) belong to the invention. In particular this relates to compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxylmethylene derivative, an O-(acyloxymethylene carbamate) derivative, carbamate, ester, amide or enaminone.

The terms "common protecting group" and "conventional protecting groups" refer to groups introduced into a molecule by chemical modification of specific functional groups in order to obtain chemoselectivity in certain reactions. Examples of protecting groups include but are not limited to benzyl, trimethylsilyl, tert-butyloxycarbonyl, 9-fluorenylmethyloxycarbonyl, dimethylacetal.

The term "physiologically compatible salts" refers to salt forms that are physiologically compatible (i.e. pharmacologically acceptable) and substantially non-toxic to the subject being administered the compounds of the invention. Physiologically compatible salts of compounds of formula I include conventional and stoichiometrical acid-addition salts or base-addition salts formed from suitable non-toxic organic or inorganic acids or inorganic bases. Acid addition salts, for example, from compounds of formula I with a basic nitrogen atom are formed preferably with organic or inorganic acids. Suitable inorganic acids are, for example, halogenic acids such as hydrochloric acid, sulfuric acid, or phosphoric acid. Suitable organic acids are, for example, carboxylic, phosphonic, or sulfonic acids, for example acetic acid, propionic acid, glycolic acid, lactic acid, hydroxybutyric acid, malic acid, malenic acid, malonic acid, salicylic acid, fumaric acid, succinic acid, adipic acid, tartaric acid, citric acid, glutaric acid, 2- or 3-glycerophosphoric acid and other mineral and carboxylic acids well known to those skilled in the art. The salts are prepared by contacting the free base forms with a sufficient amount of the desired acid to produce a salt in the conventional manner. Compounds containing acidic substituents may also form salts with inorganic or organic bases. Examples of suitable bases for salt formation include, but are not limited to, inorganic bases such as alkali or alkaline earth-metal (e.g., sodium, potassium, lithium, calcium, or magnesium) hydroxides, and those derived from ammonium hydroxides (e.g., a quaternary ammonium hydroxide such as tetramethylammonium hydroxide). Also contemplated are salts formed with pharmaceutical acceptable amines such as ammonia, alkyl amines, hydroxyalkylamines, N-methylglucamine, benzylamines, piperidines, and pyrrolidines and the like. Certain compounds will be acidic in nature, e.g. those compounds which possess a carboxyl or phenolic hydroxyl group. Salts of phenols can be made by heating acidic compounds with any of the above mentioned bases according to procedures well known to those skilled in the art.

The term "metabolites" refers to active compounds derived from catabolism of a compound of formula I upon introduction into a biological milieu, such as a human. The term "metabolites" includes primary metabolites as well as secondary metabolites of a compound of formula I.

The term "solvates" pertains to the association of suitable organic solvent molecules with molecules or ions of a compound of formula I. As used herein, the term "solvates" refers both to stable solvates, containing a defined number of solvent molecules pro molecule of a compound of formula I, and inclusion complexes, which are less stable and contain a variable number of solvent molecules pro molecule of a compound of formula I.

The term "composition" is intended to encompass a product comprising the specified ingredients in the specified amounts, as well as any product which results, directly or indirectly, from combination of the specified ingredients in the specified amounts.

The phrase "effective amount" as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically acceptable excipient(s)/carrier(s) utilized, and like factors within the knowledge and expertise of the attending physician.

EMBODIMENTS (SUBCLAIMS AND FURTHER EMBODIMENTS)

It will be appreciated that the compounds and methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

In one embodiment, the invention relates to compounds of formula (I), (Ia), (Ib), (Ic), (Id), (Ix) or (Iy), wherein n represents 2, 3, 4, 5 or 6, preferably n represents 2, 3, 4 or 6, more preferably n represents 3 or 4.

Another embodiment relates to compounds as previously defined, wherein $R^1$ is selected from the group consisting of —H, —($C_1$-$C_6$)alkyl, -phenyl or —($C_1$-$C_4$)alkyl-phenyl, preferably from —H, -methyl or -benzyl.

According to another embodiment, the invention discloses compounds of formula, (Ib), (Ic), (Id), (Ix) or (Iy), wherein X and Y individually represent F or X and Y together represent =O, wherein $R^7$ is ethyl, methoxy, ethoxy, methoxyethyl, propyl or hydrogen (—H), preferably $R^7$ is hydrogen.

One embodiment relates to compounds of the invention, wherein $R^2$ is selected from the group consisting of:
(a) —($C_1$-$C_7$)alkyl, which is optionally substituted by halogen, —$OR^4$, —O—$SO_2$—$R^4$, —$NR^4R^5$, or —$COR^4$; the number of said substituents being 1, 2 or 3 for halogen, and 1 or 2 for any combination of said halogen, —$OR^4$, —$NR^4R^5$, —O—$SO_2$—$R^4$ and —$COR^4$ moieties; preferably —($C_1$-$C_6$)alkyl, which is optionally substituted by —$OR^4$, —O—$SO_2$—$R^4$, —$NR^4R^5$; the number of said substituents being 1 or 2 for any combination of said —$OR^4$, —O—$SO_2$—$R^4$ and —$NR^4R^5$ moieties; more preferably —($C_1$-$C_5$)alkyl, which is optionally substituted by benzenesulfonyloxy, benzyl-methyl-amino, cyclohexyl, dimethylamino, dioxothiomorpholin-4-yl, formyl, hydroxyl, methoxy, or phenyl,
(b) aryl or aryl-($C_1$-$C_4$)alkyl, in which the aryl moiety is monocyclic or bicyclic; and which aryl moiety is optionally substituted by halogen, carbonitril, nitro, —$OR^4$, —$R^6$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —$NR^4R^5$, —$COOR^4$ and —$COR^4$ moieties; and in which the alkyl moiety is optionally substituted by 1, 2 or 3 halogens; preferably aryl or aryl-($C_1$-$C_2$)alkyl, in which the aryl moiety is phenyl, benzyl or naphthyl; and which aryl moiety is optionally substituted by halogen, carbonitril, nitro, —$OR^4$, —$R^6$, —$NR^4R^5$, or —$COOR^4$; the number of said substituents being 1, 2, 3 or 4 for halogen, and 1 or 2 for any combination of said halogen, carbonitril, nitro, —$OR^4$, —$R^6$—$NR^4R^5$ and —$COR^4$ moieties; more preferably phenyl or naphthyl, which are optionally substituted by carbonitril, dimethylamino, formyl, hydroxyl, hydroxymethyl, methoxy, methoxycarbonyl, methyl, nitro, trihalomethoxy, trihalomethyl, or 1 or 2 halogens,
(c) heteroaryl or heteroaryl-($C_1$-$C_4$)alkyl, in which the heteroaryl moiety contains one, two or three heteroatoms independently selected from the group consisting of N, O or S, the number of N atoms being 0, 1, 2 or 3, and the number of O and S atoms each being 0, 1 or 2, and which heteroaryl moiety is optionally substituted by halogen, nitro, —$OR^4$, —$R^6$, —$NR^4R^5$, —$COOR^4$ or —$COR^4$, the number of said substituents being 1, 2, 3 or 4 for halogen, and 1 or 2 for any combination of said halogen, nitro, —$OR^4$, —$R^6$, —$NR^4R^5$, —$COOR^4$ and —$COR^4$ moieties, and in which the alkyl moiety is optionally substituted by 1, 2 or 3 halogens; preferably heteroaryl or heteroaryl-($C_1$-$C_2$)alkyl, in which the heteroaryl moiety contains one, two or three heteroatoms independently selected from the group consisting of N, O or S, the number of N atoms being 0, 1 or 2, and the number of O and S atoms each being 0 or 1, and which is optionally substituted by —$R^6$; more preferably pyridine-2-yl, pyridine-3-yl, pyridine-4-yl, fur-2-yl, fur-3-yl, thiophen-2-yl, thiophen-3-yl, or imidazol-4-yl, and which are optionally substituted by methyl, (d) ($C_3$-$C_7$)cycloalkyl or ($C_3$-$C_7$)cycloalkyl-($C_1$-$C_4$)alkyl, in which the cycloalkyl moiety is optionally substituted by halogen, —$OR^4$, —$R^6$, —$NR^4R^5$, or —$COR^4$; the number of said substituents being 1, 2 or 3 for halogen, and 1 or 2 for any combination of said halogen, —$OR^4$, —$R^6$—$NR^4R^5$ and —$COR^4$ moieties; preferably ($C_3$-$C_6$)cycloalkyl or ($C_3$-$C_6$)cycloalkyl-($C_1$-$C_2$)alkyl, in which the cycloalkyl moiety is optionally substituted by halogen, —$OR^4$ and —$R^6$; the number of said substituents being 1, 2 or 3 for halogen, and 1 or 2 for any combination of said halogen, —$OR^4$, or —$R^6$ moieties; more preferably cyclopropyl, cyclopentyl, or cyclohexyl, and which are optionally substituted by hydroxyl, (e) cycloheteroalkyl or cycloheteroalkyl-($C_1$-$C_4$)alkyl, in which the cycloheteroalkyl moiety is optionally substituted by halogen, —$OR^4$, or —$R^6$; the number of said substituents being 1, 2 or 3 for halogen, and 1 or 2 for any combination of said halogen, —$OR^4$ and —$R^6$ moieties; and cycloheteroalkyl or cycloheteroalkyl-($C_1$-$C_2$)alkyl, in which the cycloalkyl moiety is selected from the group consisting of piperidinyl, morpholinyl, thiomorpholinyl, piperazyl, pyryl, pyrrolidinyl, tetrahydrofuryl, azepanyl and tetrahydrothienyl, and which cycloheteroalkyl moiety is optionally substituted by —$OR^4$ or —$R^6$; and (f) —($C_1$-$C_4$)alkanoyl, preferably acetyl.

Within the substituent $R^2$, the residues $R^4$ and $R^5$ are each independently selected from the group consisting of H, —($C_1$-$C_4$)alkyl, optionally substituted by 1, 2 or 3 halogens and/or optionally substituted by 1, 2 or 3 hydroxyl moieties; and aryl and aryl-($C_1$-$C_4$)alkyl, optionally substituted in the aryl moiety by 1, 2 or 3 halogens, or $R^4$ and $R^5$ form together with the nitrogen atom, to which they are attached, a cyclic 6-membered ring system, which is saturated or contains one or more double bonds between the ring atoms, and which ring optionally contains a sulfoxide moiety in addition to the nitrogen atom, and $R^6$ represents —($C_1$-$C_4$)alkyl, which is optionally substituted by 1, 2 or 3 halogens, and/or optionally substituted by 1, 2 or 3 hydroxyl moieties. Preferably, each $R^4$ and $R^5$ is independently selected from the group consisting of H, —($C_1$-$C_4$)alkyl, optionally substituted by 1, 2 or 3 halogens and/or optionally substituted by hydroxyl; and phenyl or phenyl-($C_1$-$C_2$)alkyl, or $R^4$ and $R^5$ form together with the nitrogen atom, to which they are attached, a cyclic 6-membered ring system, which is saturated or contains one or more double bonds between the ring atoms, and which ring optionally contains a sulfoxide moiety in addition to the nitrogen atom, and $R^6$ represents —($C_1$-$C_4$)alkyl, which is optionally substituted by 1, 2 or 3 halogens and/or optionally substituted by hydroxyl.

Administration Forms and Treatment Methods

The method of the invention is primarily intended for treatment in a mammal, preferably in humans and other primates, of steroid hormone dependent diseases or disorders, in particular estradiol dependent diseases or disorders, wherein the steroid hormone dependent disease or disorder preferably requires the inhibition of a 17β-hydroxysteroid dehydrogenase (HSD) enzyme, preferably the type 1 17β-hydroxysteroid dehydrogenase (HSD) enzyme [EC 1.1.1.62].

The compounds may be administered orally, dermally, parenterally, by injection, by pulmonal or nasal delivery, or sublingually, rectally or vaginally in dosage unit formulations. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical application or transdermal administration. One or more compounds may be present in association with one or more non-toxic pharmaceutically acceptable auxiliaries such as excipients, adjuvants (e.g. buffers), carriers, inert solid diluents, suspending agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated for example as immediate release, sustained release, pulsatile release, two or more step release, depot or other kind of release formulations.

The manufacture of the pharmaceutical compositions according to the invention may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc. Suitable auxiliaries and further ingredients may be such as recommended for pharmacy, cosmetics and related fields and which preferably are listed in the European Pharmacopoeia, FDA approved or cited in the "GRAS" list (FDA List of food additives that are 'generally recognized as safe' (GRAS)).

One mode of application of the compounds of general formula I or of pharmaceutical compositions comprising one or more of said compounds is oral application, e.g., by tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the compounds suitable for the purposes of the present invention as defined above can be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the active ingredients may also be dispersed in a microparticle, e.g. a nanoparticulate, composition.

For parenteral administration, the active agents can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the active agent can be in the form of an aqueous, lipid, oily or other kind of solution or suspension or even administered in the form of liposomes or nano-suspensions.

Transdermal application can be accomplished by suitable patches, as generally known in the art, specifically designed for the transdermal delivery of active agents, optionally in the presence of specific permeability enhancers. Furthermore, also emulsions, ointments, pastes, creams or gels may be used for transdermal delivery.

Another suitable mode of administration is via intravaginal devices (e.g. vaginal rings) or intrauterine systems (IUS) and intrauterine devices (IUD), respectively, containing reservoirs for controlled release of active agents over extended periods of time. Such IUS or IUDs (as, e.g., MIRENA™) is introduced into the uterine cavity where it continuously releases defined amounts of hormone for up to 5 years (or until the system is removed).

For rectal or vaginal administration of the drug the compounds may also be administered in the form of suppositories. These compositions can be prepared by mixing the drug with a suitable non-irritating excipient which is solid at ordinary temperatures but liquid at the rectal or vaginal temperature and will therefore melt in the rectum or vagina to release the drug.

A further drug formulation is a formulation intended for the topical, local and/or regional administration of the compound to the reproductive organs, in particular to a body region selected from the group consisting of the uterus, fallopian tubes, peritoneal space, pelvic cul-de-sac, ovaries, and urinogenital tract, in amounts effective to treat various conditions, particularly local diseases of the female reproductive system, such as pelvic, uterine, cervical and vaginal diseases, as described e.g. within EP 0 977 555 A1 (and related U.S. Pat. No. 5,993,856), U.S. Pat. No. 5,993,856, U.S. Pat. No. 6,652,874, or U.S. Pat. No. 6,416,778. The formulation comprises drug particles, preferably in the form of a micro- or nano-particles, suitable for regional administration of an effective amount of drug, wherein the effective amount is a dosage which results in low serum drug levels and reduced side effects as compared to systemic administration of the drug. In particular, the formulation comprises a carrier promoting quick uptake of the drug into the blood stream, a carrier manipulating release of drug, or a carrier promoting adhesion of the drug selected from the group consisting of a liquid suspension or dispersion, a hydrogel suspension or dispersion, a topical ointment, a cream, a lotion, and a foam.

Another mode of application is by implantation of a depot implant comprising an inert carrier material, such as biologically degradable polymers or synthetic silicones such as e.g. silicone rubber. Such implants are designed to release the active agent in a controlled manner over an extended period of time (e.g. 3 to 5 years).

It will be appreciated by those skilled in the art that the particular method of administration will depend on a variety of factors, all of which are considered routinely when administering therapeutics.

The actually required dosages of the agents of this invention for any given patient will depend upon a variety of factors, including, but not limited to the activity of the specific compound employed, the particular 17beta HSD type 1, type 2 or type 3 related condition being treated, the particular composition formulated, the mode of administration, time and duration of administration, route of administration and the particular site being treated, and furthermore the age of the patient, the body weight of the patient, the general health of the patient, the gender of the patient, the diet of the patient, rate of excretion, drug combinations, and the severity of the condition undergoing therapy.

It will be further appreciated by one skilled in the art that the optimal course of treatment, i.e., the mode of treatment and the daily number of doses of a compound of formula I or a pharmaceutically acceptable salt thereof given for a defined number of days, can be ascertained by those skilled in the art using conventional treatment tests. Optimal dosages for a given set of conditions may be ascertained by those skilled in the art using conventional dosage-determination tests in view of the experimental data for a given compound. For oral administration, an exemplary daily dose generally employed will be from about 0.001 µg/kg to about 10 mg/kg of total body weight, whereby courses of treatment may be repeated at appropriate time intervals. Administration of pro-drugs may be dosed at weight levels that are chemically equivalent to the weight levels of the fully active compounds. The daily dosage for parenteral administration will generally be from about 0.001 µg/kg to about 10 mg/kg of total body weight. A daily rectal dosage regimen will generally be from about 0.001 µg/kg to about 20 mg/kg of total body weight. A daily vaginal dosage regimen will generally be from about 0.001 µg/kg to about 10 mg/kg of total body weight. The daily topical dosage regimen will generally be from about 0.01 µg to about 10 mg administered between one to four times daily. The transdermal concentration will generally be that required to maintain a daily dose of from 0.001 µg/kg to 10 mg/kg of total body weight. The total dosage of administration forms releasing the drug compound over a prolonged period of time, i.e. from about several weeks to some years, depends on the time of administration, on the kind of device (intravaginal devices, intrauterine systems, intrauterine devices, implants etc.) and on the kind of release behaviour of the particular device. In general, the daily released dose of active compound will be from about 0.001 µg/kg to about 1 mg/kg of total body weight. Since the devices often only need to achieve a certain local and/or regional concentration of active compound, the daily released dosage can be lower in comparison to e.g. oral administration.

Abbreviations and Acronyms

As employed herein, the following terms have the indicated meanings.

TABLE 2 terms with indicated meanings

| 9-BBN | 9-borabicyclo [3.3.1]nonane | MEOH | METHANOL |
|---|---|---|---|
| 18-crown-6 | 1,4,7,10,13,16-hexaoxa-cyclooctadecane | MgSO$_4$ | magnesium sulfate |
| Ac$_2$O | acetic anhydride | MS | mass spectroscopy |
| aq. | aqueous | MsCl | mesyl chloride |
| Bn | benzyl | MTBE | Methyl-tert-butylether |
| brine | saturated sodium chloride solution | µM | micro molar |
| Celite ® | CAS No 68855-54-9 | NaCl | sodium chloride |
| CuI | copper iodide | nM | nanomolar |
| CuSO$_4$ | copper sulfate | NMO | 4-methylmorpholine N-oxide |
| DAST | N,N-diethylaminosulfur trifluoride | NaN$_3$ | sodium azide |
| DCM | dichloromethane | Na$_2$SO$_4$ | sodium sulfate |
| Diglyme | diethylene glycol | Na$_2$S$_2$O$_5$ | sodium metabisulfite |

TABLE 2-continued terms with indicated meanings

| | dimethyl ether | | |
|---|---|---|---|
| DMAP | 4-(Dimethylamino)-pyridine | NaBH$_4$ | sodium tetrahydridoborate |
| DMF | Dimethyl formamide | NADPH | nicotinamide adenine dinucleotide phosphate-oxidase |
| DMSO | dimethyl sulfoxide | NH$_3$ | ammonia |
| Et$_3$N | triethyl amine | NH$_4$Cl | ammonium chloride |
| EtOAc | ethyl acetate | NH$_4$OOCH | ammonium formate |
| EtOH | ethyl alcohol | NaHCO$_3$ | sodium bicarbonate |
| GRAS | generally recognized as safe | NMO | N-methylmorpholin-N-oxid |
| h. | hours | NMR | nuclear magnetic resonance |
| H$_2$ | hydrogen | o- | ortho |
| H$_2$O | water | p- | para |
| HCl | hydrochloric acid | PG | protection group |
| hept. | heptane | ph- | phenyl |
| HMPA | hexamethyl-phosphoramide | Pd/C | carbon-supported palladium catalyst |
| HPLC | high performance liquid chromatography | ppm | parts per million |
| i- | iso | RT | room temperature |
| I$_2$ | iodine | sat. | saturated |
| IUS | intrauterine systems | SiO$_2$ | silicium dioxide |
| K$_2$CO$_3$ | potassium carbonate | T | temperature |
| KH$_2$PO$_4$ | potassium dihydrogen phosphate | TBAF | tetra-n-butylammonium fluoride |
| KH | potassium hydride | TBME | tert-butyl methyl ether |
| KOH | potassium hydroxide | THF | tetrahydrofurane |
| LC-MS | liquid chromatography with MS | TLC | Thin Layer Chromatography |
| LiCl | lithium chloride | TMNO | trimethylamine-N-oxide.hydrate |
| m- | meta | TMS | trimethylsilyl |
| Me$_3$N | trimethylamine | TMSCl | trimethylsilyl chloride |
| Me$_3$NO•.2H$_2$O | trimethylaminoxid-dihydrat | TPAP | tetrapropylammonium perruthenate |
| ME | METHYL | TsOH/TosOH | toluenesulfonic acid |
| MeO | methoxy | | |

General Preparative Methods

The compounds of the present invention may be prepared by use of known chemical reactions and procedures. Nevertheless, the following general preparative methods are presented to aid the reader in synthesizing the 17-β-hydroxysteroid dehydrogenase inhibitors with specific details provided below in the experimental section to illustrate working examples.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

The synthesis of substituted estratrien derivatives bearing a substituted triazole in position C$_{15}$ and carrying optionally additional modifications of the steroidal core at positions C$_2$, C$_3$ and/or C$_{17}$ may be introduced in the following order of general chemical modifications.

General Synthesis Schemes a) A compound of formula (Ix) can be synthesised by the introduction of the R$^7$ substituent in C$_2$ position—if present in the final compound—which has to take place first, starting from the 17β-estradiol using methods well known in the art (Steps A). In parallel, the C$_{17}$—OH function may be oxidized to the corresponding keto function. Depending on the desired nature of R$^1$, a suitable group also functioning as protecting group may be introduced at this point. Then, the estron derivative is converted into the central intermediate, the 15,16-unsaturated estrone (Steps B), which is further derivated in the C$_{15}$ position by introduction of the basic azide side chain to generate the central intermediate (Steps C-I). If desired, the modification of the C$_{17}$ function preferably takes place before finalizing the introduction of the azide side chain (Steps C-II). Compounds of the present invention may then be prepared by a process comprising coupling of the obtained azide intermediate with a terminal alkyne H—C≡C—R$^2$ as depicted below (Step D). If necessary, the C$_{17}$ keto function might be protected with conventional protecting groups during this coupling step. Finally, if desired, the protection group in C$_1$ position may be separated to deliver the C$_3$—OH derivative or may be further substituted with an alternative R$^1$ side chain (Steps E).

Synthesis of a Compound of Formula (Ix):

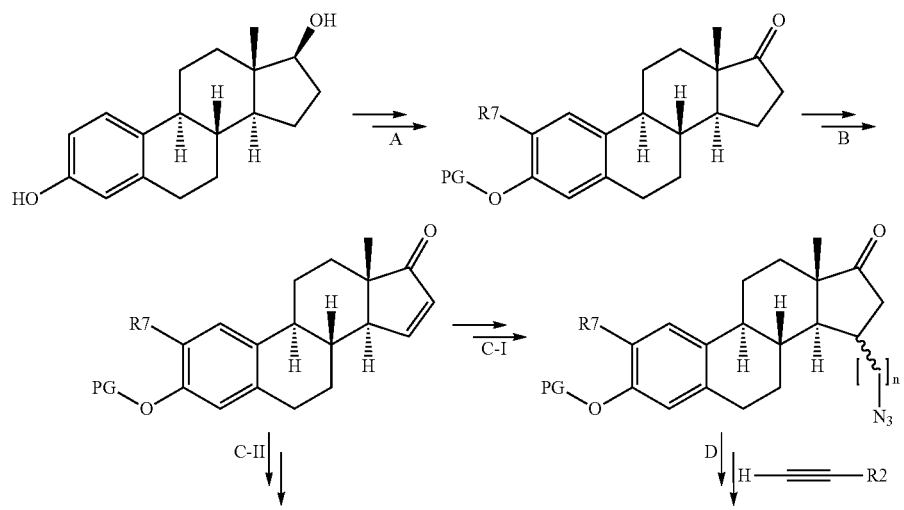

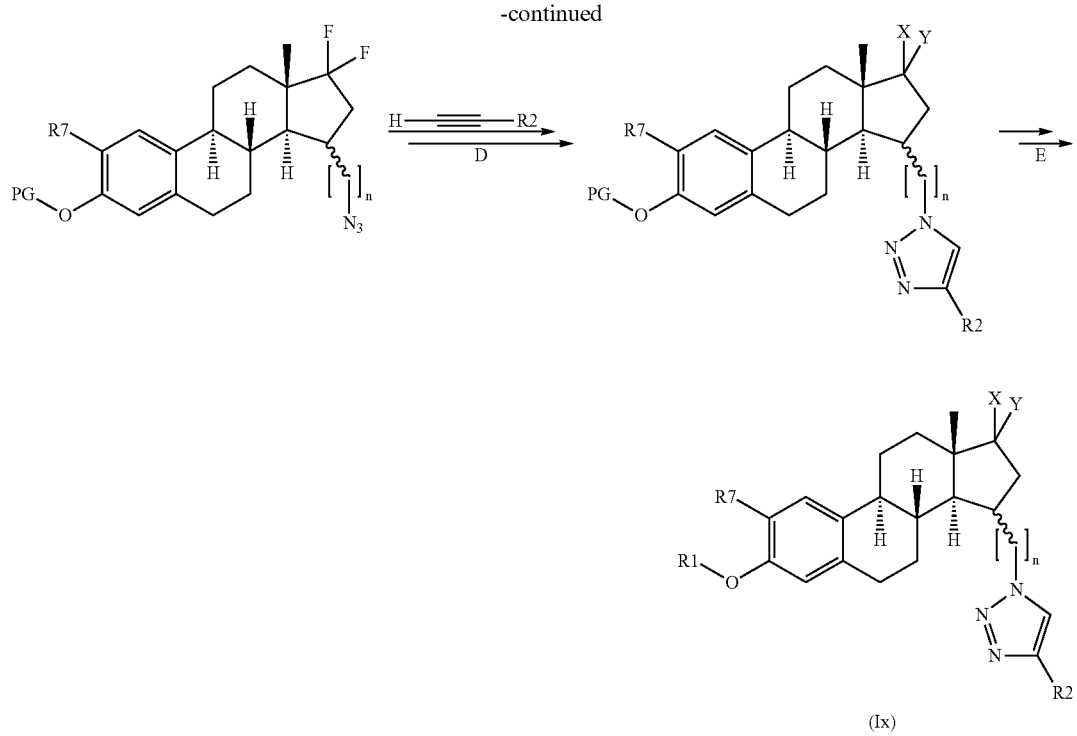

(Ix)

wherein $R^1$, $R^2$, $R^7$, X and Y have the meanings as defined herein, and PG is a common protecting group like benzyl.

Step A: The synthesis of estratrien derivatives with variations at $C_2$ is described in general and vor exemplary compounds in detail in international patent application WO 2006/032885 (and related US 2006/0128766) and in PCT application WO 2006/125800.

Step B: The preparation of the 15, 16 unsaturated estron derivate is described in detail in PCT application WO 2005/047303 and in PCT application WO 2006/125800.

Step C-I: The synthesis of the $C_{15}$ substituted azide derivate might be achieved by conventional synthesis methods as already depicted within international patent application WO 2005/047303 and in PCT application WO 2006/125800 and as depicted herein below.

Step C-II: In addition to the reaction of Step C-I, the difluorination of the $C_{17}$ atom of the estron core has to be carried out. This is a reaction well known in the art and was already disclosed in U.S. Pat. No. 3,413,321 and U.S. Pat. No. 3,347,878. Furthermore, the difluorination of the $C_{17}$ atom of the estron core may be achieved using the DAST reagent [Liu et al (1992) "Synthesis of high affinity fluorine-substituted ligands for the androgen receptor. Potential agents for imaging prostatic cancer by positron emission tomography." J Med Chem. 35(11):2113-29]. Depending on the nature of the azide intermediate or in order to enable library synthesis, it might be necessary that some of the reaction steps to introduce the $C_{15}$ azide side chain, have to be carried out after having introduced the respective fluoro group (see also PCT application WO 2006/125800 for some examples). A typical scenario might be that after optional introduction of the $R^7$ residue in $C_2$ position, the 15,16-unsaturated intermediate is prepared. This is further derivatized to the alcohol intermediate (see section "Intermediates"). Then, the fluoro group is introduced into $C_{17}$ position of the steroidal core. The so-obtained intermediate is then used for further modification of the $C_{15}$ side chain and introduction of the $R^2$ substituent. Finally, any protection groups in $C_3$ position might be cleaved off.

Step D: The coupling of the azide with a terminal alkinyl delivering the desired triazole derivatives may be carried out by using a method for the formation of 1,4 disubstituted triazoles well known to one skilled in the art of organic synthesis (see e.g. WO 2006/063585 (and related US 2006/128766) and WO 2003/101972 (and related US 2005/0222427) and references cited therein).

Step E: In case that $R^1$ represents —H, or optionally substituted —($C_1$-$C_6$)alkyl, phenyl or —($C_1$-$C_6$)alkylphenyl, then the substituent may already have been introduced during synthesis of the Intermediates as explained for $R^1$=H, $R^1$=methyl and $R^1$=benzyl or can now be introduced by replacement or derivatisation of the present $R^1$ substituent.

b) A compound of formula (Ic) can be synthesised by the introduction of the $R^7$ substituent in $C_2$ position—if present in the final compound—which has to take place first, starting from the 17β-estradiol using methods well known in the art (Steps A). In parallel, the $C_{17}$—OH function may be oxidized to the corresponding keto function. Depending on the desired nature of $R^1$, a suitable group also functioning as protecting group may be introduced at this point. Then, the estron derivative is converted into the central intermediate, the 15,16-unsaturated estrone (Steps B), which is further derivated in the $C_{15}$ position by introduction of the corresponding alkine compound in a Grignard reaction (Steps F). The compounds of formula (Ic) are then prepared from the corresponding R2 Halides via in situ generated azides in the presence of azides (e.g. NaN3) (Steps G). Then, if desired, the modification of the $C_{17}$ function takes place (Steps H). Finally, if desired, the protection group in $C_1$ position may be separated to deliver the $C_3$—OH derivative or may be further substituted with an alternative $R^1$ side chain (Steps J).

Synthesis of a Compound of Formula (Ic):

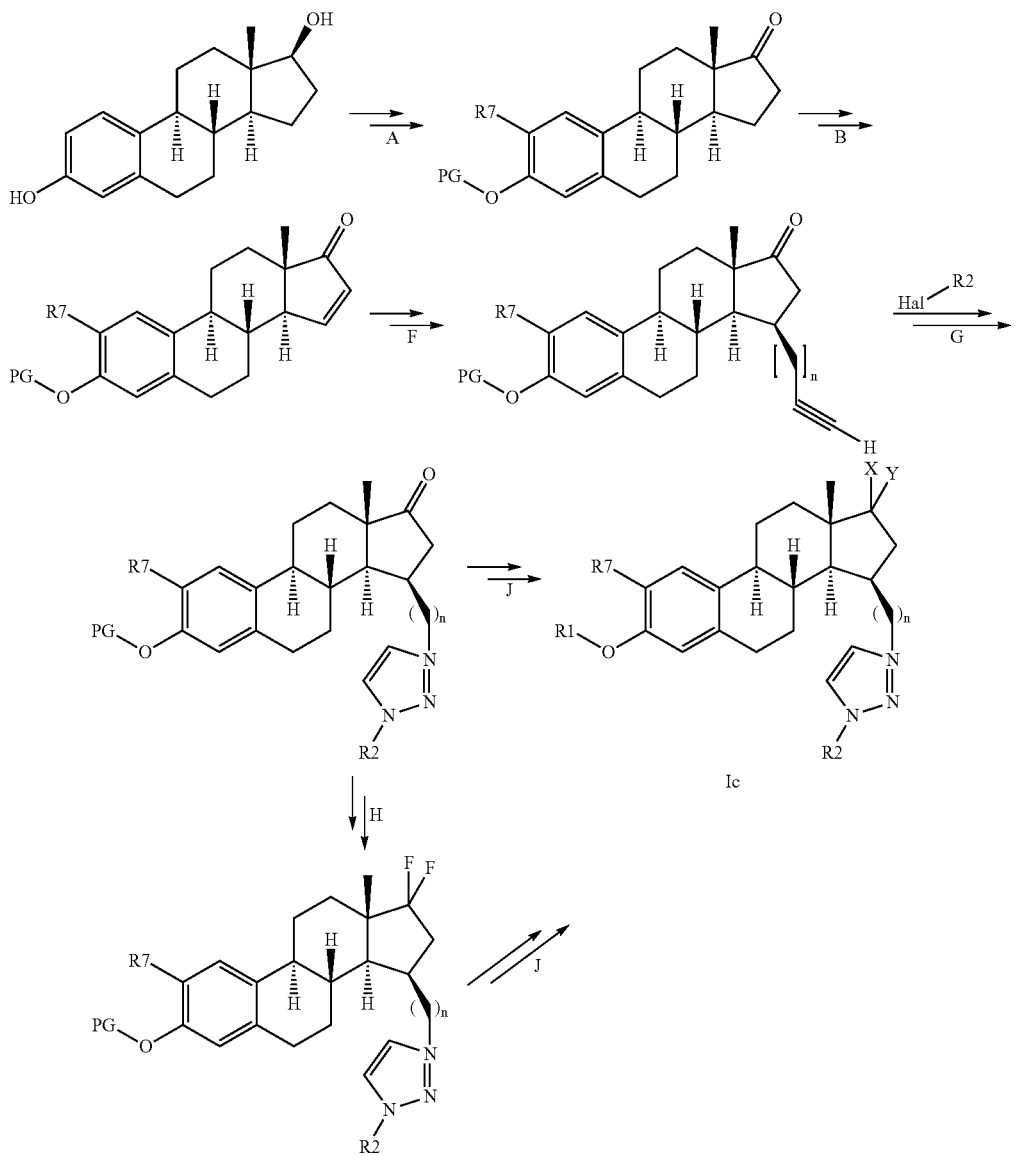

wherein $R^1$, $R^2$, $R^7$, X and Y have the meanings as defined herein, and PG is a common protecting group like benzyl.

Step A: The synthesis of estratrien derivatives with variations at $C_2$ is described in general and vor exemplary compounds in detail in international patent application WO 2006/032885 and in PCT application WO 2006/125800.

Step B: The preparation of the 15, 16 unsaturated estron derivate is described in detail in PCT application WO 2005/047303 and in PCT application WO 2006/125800.

Step F: The 15,16-unsaturated estron is coupled with the corresponding alkine compound in a Grignard reaction.

Step G: The Triazoles are prepared from the alkine substituted estron derivate and the corresponding R2 Halides via in situ generated azides. The one pot synthesis for specific aryl triazoles is described in detail in Andersen J, Bolvig S, Liang X (2005) "Efficient One-Pot Synthesis of 1-Aryl 1,2,3-Triazoles from Aryl Halides and Terminal Alkynes in the Presence of Sodium Azide" Synlett, 2005, 19:2941.

Step H: Fluorination with Deoxoflur results converts the keto triazoles into the corresponding di-fluoro triazoles Step J: Deprotection of the oxygen by introduction of R1 group.

c) Compounds of formula (Id) can be synthesised by the introduction of the $R^7$ substituent in $C_2$ position—if present in the final compound—which has to take place first, starting from the 17β-estradiol using methods well known in the art (Steps A). In parallel, the $C_{17}$—OH function may be oxidized to the corresponding keto function. Depending on the desired nature of $R^1$, a suitable group also functioning as protecting group may be introduced at this point. Then, the estron derivative is converted into the central intermediate, the 15,16-unsaturated estrone (Steps B), which is further derivated in the $C_{15}$ position by introduction of the corresponding alkene compound (Steps K). Coupling with the triazole allyl compound synthesised (Steps N) from the corresponding allyl alkine affords the allyl triazoles (Steps M). Reduction of the double bond leads to the triazole compound. Then, if desired, the modification of the $C_{17}$ function takes place (Steps H). Finally, if desired, the protection group in $C_1$ position may be separated to deliver the $C_3$—OH derivative or may be further substituted with an alternative $R^1$ side chain (Steps J).

Synthesis of Compounds of Formula (Id):
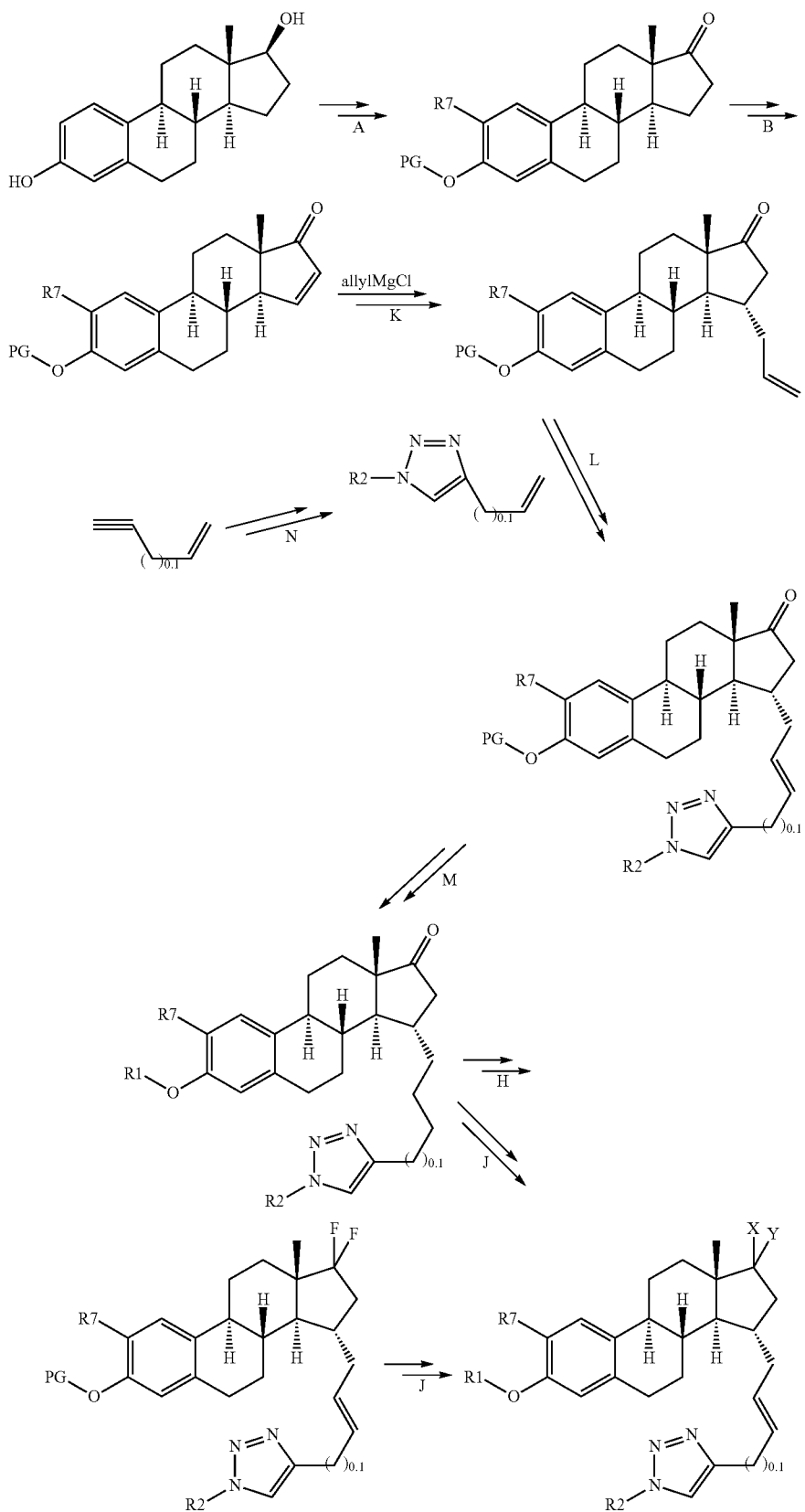

wherein $R^1$, $R^2$, $R^7$, X and Y have the meanings as defined herein, and PG is a common protecting group.

Step A: The synthesis of estratrien derivatives with variations at $C_2$ is described in general and vor exemplary compounds in detail in international patent application WO 2006/032885 and in PCT application WO 2006/125800.

Step B: The preparation of the 15, 16 unsaturated estron derivate is described in detail in PCT application WO 2005/047303 and in PCT application WO 2006/125800.

Step K: The preparation of the 15, 16 unsaturated allyl derivate is described in detail in WO 2006/125800.

Step L: Introduction of the Triazole moiety synthesized from the corresponding allyl alkine (Step N) and chain elongation (e.g. via Metathesis).

Step M: Reduction of the double bond lead to the O-protected Triazoles.

Step H: Fluorination with Deoxoflur results converts the keto triazoles into the corresponding di-fluoro triazoles Step J: Deprotection of the oxygen by introduction of R1 group.

Experimental Section

Examples of preparations of compounds of the invention are provided in the following detailed synthetic procedures. In the tables of compounds to follow, the synthesis of each compound is referenced back to these exemplary preparative steps.

The compounds of formula I may be prepared using the reactions and techniques described in this section. The reactions are performed in solvents that are appropriate with respect to the reagents and materials employed and that are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis, that the functionality present on various positions of the molecules used as the starting compounds or intermediates in the syntheses, must be compatible with the reagents and reactions proposed. Not all compounds of formula I falling into a given class may be compatible with some of the reaction conditions required in some of the methods described. Such restrictions of substituents or functional groups which are compatible with the reaction conditions will be readily apparent to one skilled in the art and alternative methods can be used.

In single compound synthesis as well as in combinatorial synthesis all reactions were stirred magnetically or shaked with an orbital shaker unless otherwise indicated. Sensitive liquids and solutions were transferred via syringe or canula, and introduced into reaction vessels through rubber septa, in these cases the reaction were carried out under a positive pressure of dry argon or dry nitrogen. Commercial grade reagents and solvents were used without further purification. All temperatures are reported uncorrected in degrees Celsius (° C.). Unless otherwise indicated, all parts and percentages are by volume. Thin-layer chromatography (TLC) was performed on Merck®; pre-coated glass-backed silica gel or aluminium sheets 60A F-254250 um plates. Visualization of plates was effected by one or more of the following techniques: (a) ultraviolet illumination (254 nm or 266 nm), (b) exposure to iodine vapor, (c) spraying of the plate with Schlittler's reagent solution followed by heating, (d) spraying of the plate with anisaldehyde solution followed by heating, and/or (e) spraying of the plate with Rauxz reagent solution followed by heating. Column chromatography (flash chromatography) was performed using 230-630 mesh ICN, SiliTech 60A silica gel. $^1$H-NMR spectra were measured with a Bruker ARX (400 MHz) or Bruker ADVANCE (500 MHz) spectrometer with the solvent as indicated. HPLC electrospray mass spectra (HPLC ES-MS) were obtained using the following method and equipment: Samples were separated by reversed phase high pressure liquid chromatography (RP-HPLC) coupled to a quadrupol MS. HPLC was performed at a flow of 1000 ul/min using Xter-MS C18 columns (i. d. 4.6 mm, length 50 mm, particle size 2.5 um) or Phenomenex LunaC18 (2) 30*4.6 mm columns. For most samples, a gradient from 0% eluent B to 95% B was run in 10 min, with eluent A consisting of water, 10 mM ammonium-acetate at pH 5+5% acetonitrile and eluent B consisting of acetonitrile. Two different setups were used: 1. Waters Alliance 2795 coupled to a Waters ZQ MS, a Waters 2996 diode array detector (DAD) and an evaporative light scattering detector (ELSD, EL-ELS1000, PolymerLabs). Ionization: electrospray positive and negative mode ES+/−. or 2. LC200 pump (PE) coupled to an API100 MS (Applied Biosystems Sciex), a variable wavelength detector Waters 2487 set to 225 nm, and an ELSD (Sedex 75), ES+. In both setup versions spectra were scanned with a scan range of m/z 100 to 800 or 100 to 900. Gas chromatography-mass spectra (GC-MS) analyses were performed with an Agilent 6890 gas chromatograph equipped with an DB-5MS column (0.25 i. d., length 30 m) and an Agilent 5973 MSD quadrupol detector (ionization with electron impact (EI) at 70 eV; source temperature 230 C). NMR spectra, LRMS, elemental analyses and HRMS of the compounds were consistent with the assigned structures.

The Synthesis of Estron Derivatives of Formula Ix
Intermediates of Compounds of Formula Ix The synthesis of estratrien derivatives with variations at C2 is described in detail in PCT application WO 2006/125800.

The synthesis of estron derivatives carrying an alkyl side chain with an azide group in C15 position as depicted in the following general formula

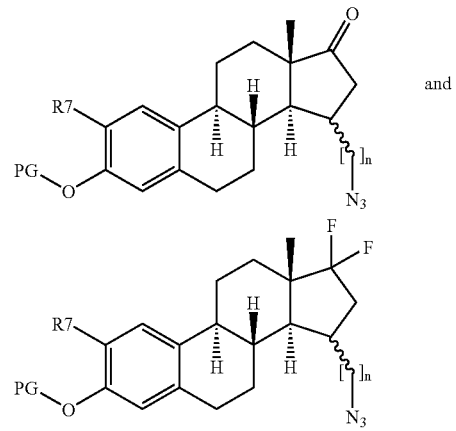

and is described for compounds with $R^7$=H in C2 position in patent application WO 2005/047303 and for compounds with $R^7 \neq H$ in C2 position or with an optional difluoro group in C17 position in the PCT application WO 2006/125800 (intermediate compounds of general formula XLIII). Typically, the corresponding alcohol derivatives are used as intermediates for the azide synthesis. A possible synthesis route to obtain such alcohol intermediates—also with different chain length in the $C_{15}$ substituent and different stereochemistry in $C_{15}$— is described for compounds with $R^7$=H in $C_2$ position in patent application WO 2005/047303 and for compounds with $R^7 \neq H$ in $C_2$ position or with an optional difluoro group in $C_{17}$ position in the PCT application WO 2006/125800 (intermediate compounds of general formula XXXI and XXXII).

Alternatively, certain azide intermediates with X and Y=O for the synthesis of formula (Ix) compounds may be prepared stereoselectively via the following route (scheme 1).

scheme 1: preparation route azide intermediate (XII-I), $R^7$ as defined in formula (I) and PG a common protecting group

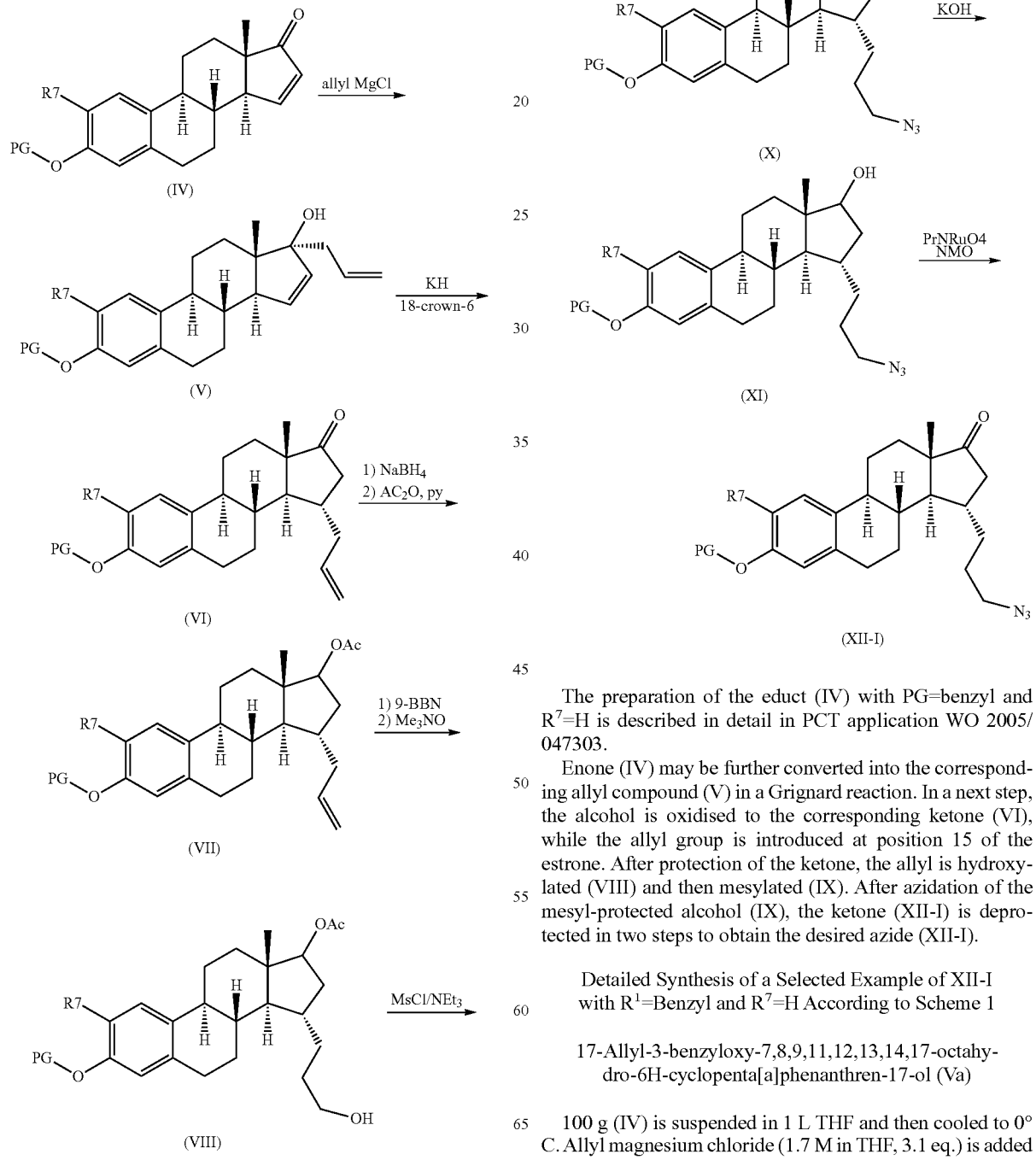

The preparation of the educt (IV) with PG=benzyl and $R^7$=H is described in detail in PCT application WO 2005/047303.

Enone (IV) may be further converted into the corresponding allyl compound (V) in a Grignard reaction. In a next step, the alcohol is oxidised to the corresponding ketone (VI), while the allyl group is introduced at position 15 of the estrone. After protection of the ketone, the allyl is hydroxylated (VIII) and then mesylated (IX). After azidation of the mesyl-protected alcohol (IX), the ketone (XII-I) is deprotected in two steps to obtain the desired azide (XII-I).

Detailed Synthesis of a Selected Example of XII-I with $R^1$=Benzyl and $R^7$=H According to Scheme 1

17-Allyl-3-benzyloxy-7,8,9,11,12,13,14,17-octahydro-6H-cyclopenta[a]phenanthren-17-ol (Va)

100 g (IV) is suspended in 1 L THF and then cooled to 0° C. Allyl magnesium chloride (1.7 M in THF, 3.1 eq.) is added carefully at such a rate that −5° C. T<0° C. After complete addition, the mixture is stirred for 4 h at RT, and then poured in ice-cooled sat. NH$_4$Cl (3.5 L). The aqueous layer is extracted twice with DCM (2×750 mL). The combined organic layers are dried over Na$_2$SO$_4$, concentrated and stripped with THF (250 mL) to give (Va) as a yellow solid (113.5 g quant.).

15-Allyl-3-benzyloxy-6,7,8,9,11,12,13,14,15,16-decahydro-cyclopenta[a]phenanthren-17-one (VIa)

30% KH in mineral oil (5.2 eq.) is washed with heptane (2×250 mL) and suspended in THF (400 mL). A solution of (Va) (57.1 g, 143 mmol) and 18-crown-6 (191 g, 722 mmol) in THF (1.1 L) was added carefully. During the addition, H$_2$ evolves, T rises from 18° C. to 26° C. and the color darkens. The mixture is stirred for 4 hrs at RT and is then poured in sat. NH$_4$Cl (2.5 L). The mixture is extracted with EtOAc (3×500 mL) and the combined organic layers are washed with brine (500 mL), dried over Na$_2$SO$_4$, concentrated and stripped with toluene. The crude residue is taken up in toluene filtered and concentrated to give crude (Via) as a red/brown-oil. This is purified (with a tedious column) over SiO$_2$ (DCM:heptane 2:1, later 7:2) to give (VIa) (72%) as a white solid.

Acetic acid 15-allyl-3-benzyloxy-13-methyl-7,8,9,11,12,13,14,15,16,17-decahydro-6H-cyclopenta[a]phenanthren-17-yl ester (VIIa)

To steroid (VIa) (204 mmol) in THF (1225 mL) and water (325 mL) is added NaBH$_4$ (4 eq.) in portions under cooling with a waterbath. After 0.5 h. the reaction mixture is warmed to 20° C. with a waterbath. The reaction mixture is stirred for 3.5 h after which sat. NH$_4$Cl (870 mL) is added very carefully, while cooling with a cold waterbath. The layers are separated and the aqueous layer is extracted with EtOAc (3×750 mL). The combined organic layers are washed with brine (750 mL), dried overnight over Na$_2$SO$_4$ and concentrated to give 15-Allyl-3-benzyloxy-13-methyl-7,8,9,11,12,13,14,15,16, 17-decahydro-6H-cyclopenta[a]phenanthren-17-ol (97%) as a thick yellow/green oil which is dissolved in pyridine (840 mL). DMAP (0.5 g) is added and carefully Ac$_2$O (373 mL). After the addition of ca. 40 mL, the temperature rises a few degrees. After the temperature has stabilised, addition is continued. The color changes to yellow and the reaction is stirred overnight at RT. After TLC-analysis reveals almost complete conversion, the mixture is poured in 2500 mL water and 400 mL ice. The resulting mixture is extracted with DCM (3×840 mL) and the combined organic layers are washed with water (840 mL) and brine (840 mL), dried over Na$_2$SO$_4$ and concentrated to give crude acetate (VIIa). The crude oil, which contained pyridine, is taken up in DCM and washed with 1 M citric acid (2×500 mL) and sat. NaHCO$_3$ (500 mL). The DCM layer is dried over Na$_2$SO$_4$ and concentrated to give acetate (VIIa) (78.5 mL, 90%) as an orange oil which is used without purification in the next step.

Acetic acid 3-benzyloxy-15-(3-hydroxy-propyl)-13-methyl-7,8,9,11,12,13,14,15,16,17-decahydro-6H-cyclopenta[a]phenanthren-17-yl ester (VIIIa)

To allyl (VIIa) (47.2 mmol) in THF (300 mL) is added 0.5 M 9-BBN (1.5 eq.) at 10° C. fast. After stirring at RT for 2 h., an additional portion of 0.5 M 9-BBN (0.8 eq.) is added and the mixture is stirred an additional 2.5 hours at RT. Diglyme (430 mL), EtOH (150 mL) and Me$_3$NO. 2H$_2$O (6.8 eq.) are added and the mixture is heated to 150° C., while removing Me$_3$N, THF and EtOH with a Dean-Stark trap. The mixture is kept an additional hour at 150° C. and then cooled to RT overnight. After NMR analysis revealed complete conversion, water (500 mL) and EtOAc (500 mL) are added. The layers are separated, the aqueous layer is extracted with EtOAc (2×500 mL) and the combined organic layers are ished with 10% Na$_2$S$_2$O$_5$ (500 mL), water (500 mL) and brine (500 mL). Drying over Na$_2$SO$_4$ and concentrating give crude (VIIIa). Most diglyme is removed by Kugelrohr distillation, which give 23.0 g yellow/orange oil. The oil is purified over 1.3 L SiO$_2$ (DCM:MeOH, 97:3) to give (VIIIa) (89%) as a yellow oil.

Acetic acid 3-benzyloxy-15-(3-methanesulfonyloxy-propyl)-13-methyl-7,8,9,11,12,13,14,15,16,17-decahydro-6H-cyclopenta[a]phenanthren-17-yl ester (IXa)

Alcohol (VIIIa) (42 mmol) in THF (400 mL) is cooled with a waterbath and Et$_3$N (1.2 eq.) is added followed by dropwise addition of MsCl (1.2 eq.). The mixture is stirred at RT and monitored by TLC. After 1 h. complete conversion is observed by TLC and EtOAc (500 mL) and water (300 mL) are added. The layers are separated and the organic layer is ished with sat. NaHCO$_3$ (300 mL). The combined aqueous layers are extracted with EtOAc (500 mL) and the combined organic layers are ished with brine (300 mL), dried over Na$_2$SO$_4$ and concentrated to give mesylate (IXa) (24.4 g (contains traces of solvent, quant.) as a light yellow oil.

Acetic acid 15-(3-azido-propyl)-3-benzyloxy-13-methyl-7,8,9,11,12,13,14,15,16,17-decahydro-6H-cyclopenta[a]phenanthren-17-yl ester (Xa)

To mesylate (IXa) (42 mmol) in DMF (430 mL) is added NaN$_3$ (3 eq.) and the resulting mixture is stirred 4 hr. at 70° C. and then overnight at RT. After NMR-analysis revealed complete conversion, the reaction mixture is poured in 1 L ice/water, extracted with EtOAc (1 L, 750 mL, 500 mL) and ished with water (6×300 mL) and brine (400 mL). The organic layer is dried over Na$_2$SO$_4$ and concentrated to give (Xa) (19.8 g, quant.) as an orange oil.

15-(3-Azido-propyl)-3-benzyloxy-13-methyl-7,8,9, 11,12,13,14,15,16,17-decahydro-6H-cyclopenta[a]phenanthren-17-ol (XIa)

To azide (Xa) (29 mmol) in THF (150 mL) and MeOH (140 mL) is added KOH (4⅓ eq.) in water (140 mL). The reaction is stirred 2.5 hr. at 55° C. after which NMR-analysis revealed complete conversion and the mixture is cooled to 30° C. EtOAc (400 mL) is added, the layers are separated and the organic layer is ished with water (160 mL, 240 mL). The combined aqueous layers are extracted with EtOAc (2×240 mL) and the organic layers are combined, ished with brine (320 mL), dried over Na$_2$SO$_4$ and concentrated to give azido-alcohol (XIa) (98%) as a yellow oil which crystallises as a white solid upon standing.

15-(3-Azido-propyl)-3-benzyloxy-13-methyl-6,7,8,9, 11,12,13,14,15,16-decahydro-cyclopenta[a]phenanthren-17-one (XII-Ia)

To azido-alcohol (XIa) (28.3 mmol) in acetone (200 mL), cooled with a waterbath, is added NMO (3 eq.) followed by the addition of TPAP (994 mg, 2.8 mmol, 0.1 eq.). The waterbath is removed and the reaction is stirred at RT and monitored by TLC analysis. After 0.5 h. the reaction is driven to complete conversion and the reaction mixture is filtered over Celite®. The Celite® is ished extensively with acetone and the filtrate is concentrated to give 17.7 g crude (XII-Ia) as a black oil. The oil is purified by column chromatography over SiO₂ (1 L, DCM) to give (XII-Ia) (86%) as a light yellow oil.

Alternatively, certain intermediates with X and Y=O of formula (Ix) compounds may be prepared stereoselectively via the following route (scheme 2).

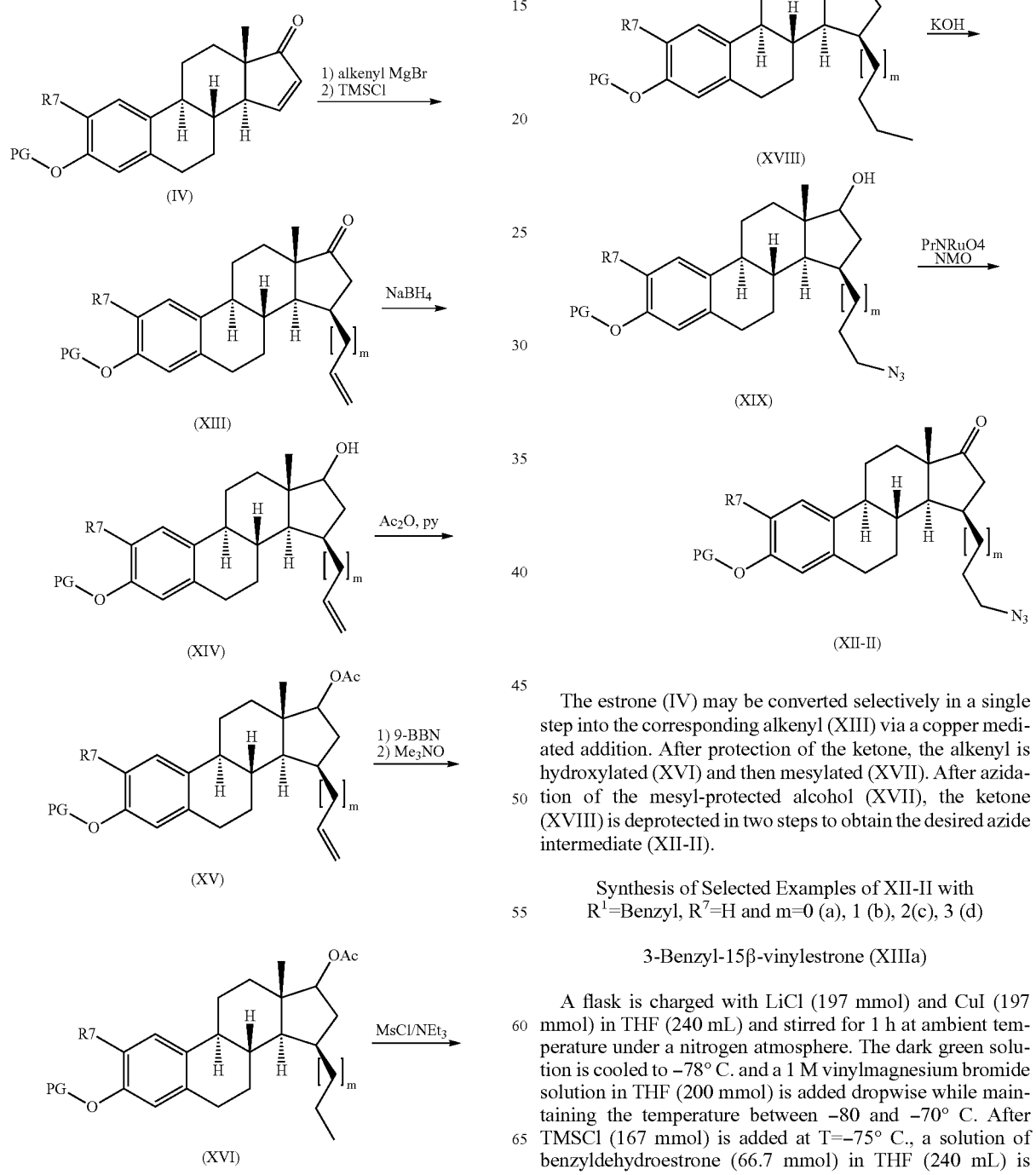

The estrone (IV) may be converted selectively in a single step into the corresponding alkenyl (XIII) via a copper mediated addition. After protection of the ketone, the alkenyl is hydroxylated (XVI) and then mesylated (XVII). After azidation of the mesyl-protected alcohol (XVII), the ketone (XVIII) is deprotected in two steps to obtain the desired azide intermediate (XII-II).

Synthesis of Selected Examples of XII-II with R¹=Benzyl, R⁷=H and m=0 (a), 1 (b), 2(c), 3 (d)

3-Benzyl-15β-vinylestrone (XIIIa)

A flask is charged with LiCl (197 mmol) and CuI (197 mmol) in THF (240 mL) and stirred for 1 h at ambient temperature under a nitrogen atmosphere. The dark green solution is cooled to −78° C. and a 1 M vinylmagnesium bromide solution in THF (200 mmol) is added dropwise while maintaining the temperature between −80 and −70° C. After TMSCl (167 mmol) is added at T=−75° C., a solution of benzyldehydroestrone (66.7 mmol) in THF (240 mL) is added dropwise at T=−80 and −72° C. The dark brown reaction mixture is stirred for 2½ h at −74° C. After the mixture is allowed to reach a temperature of 15° C., it is quenched with sat. NH$_4$Cl (300 mL). The formed suspension is filtered over Celite® and the residue is ished with water and THF. The filtrate is diluted with 1 M HCl (250 mL). The aqueous layer is extracted with EtOAc (3×200 mL). The combined organic layers are ished with 1 M HCl (300 mL). The formed suspension is filtered over Celite® and the organic layer is separated. The organic layer is ished with 2 M ammonia (2×300 mL), until the blue color of the water layer had nearly vanished, ished with brine (300 mL), dried over MgSO$_4$ and concentrated in vacuo leaving a brown solid (25 g). The solid is purified by column chromatography (SiO$_2$, DCM/hept=7:3) leaving (XIIIa) (24%) as a yellow solid.

3-Benzyl-15β-allylestrone (XIIIb)

Synthesized according to the procedure of (XIIIa) using LiCl (125 mmol), CuI (125 mmol), THF (250 mL), 1 M allylmagnesium bromide sol. in EtO$_2$ (125 mmol), TMSCl (104 mmol), benzyldehydroestrone (41.8 mmol) in THF (250 mL) yielding (XIIIb) (90%).

3-Benzyl-15β-buten-3-ylestrone (XIIIc)

Preparation of 4-butenyl-magnesiumbromide: Mg turnings (223 mmol) are activated with I$_2$ crystals under a nitrogen atmosphere. A mixture of 4-bromobutene (195 mmol) in THF (200 mL) is added dropwise in such a rate, that the solution is kept at reflux. After complete addition the mixture is refluxed for an additional 30 min. before cooling it to ambient temperature. Further, the same procedure as described for 3-benzyl-15β-vinylestrone (XIIIa), using LiCl (200 mmol), CuI (201 mmol), THF (280 mL), freshly prepared 4-butenyl-magnesiumbromide solution, TMSCl (201 mmol), benzyldehydroestrone (55.8 mmol) in THF (260 mL), is used to yield (XIIIc) (75%) after column purification.

3-Benzyl-15β-penten-4-ylestrone (XIIId)

Synthesized according to the procedure of (XIIIc) using LiCl (159 mmol), CuI (159 mmol), THF (225 mL), Mg turnings (4.3 g), 5-bromo-1-pentene (18.4 mL) in THF (150 mL), TMSCl (159 mmol), benzyldehydroestrone (44 mmol) in THF (210 mL) to yield (XIIId) (19.6 g) which is used without further purification.

3-Benzyl-15β-vinylestradiol (XIVa)

To a solution of (XIIIa) (16.4 mmol) in THF (90 mL) is added water (25 mL). Subsequently NaBH$_4$ (64 mmol) is added portionwise. The mixture is stirred for 3 h. and then quenched with aq. sat. NH$_4$Cl. The layers are separated, and the aq. layer is extracted with EtOAc (2×100 mL). The combined organic layers are ished with brine, dried over Na$_2$SO$_4$ and concentrated in vacuo yielding (XIVa) (7.45 g) as a yellow solid, which is used without further purification.

3-Benzyl-15β-allylestradiol (XIVb)

Synthesized according to the procedure of (XIVa) with (XIIIb) (37 mmol), NaBH$_4$ (177 mmol), THF (260 mL), water (70 mL) to yield (XIVb) (83%) as a pale glass, which is used without further purification.

3-Benzyl-15β-buten-3-ylestradiol (XIVc)

Synthesized according to the procedure of (XIVa) with (XIIIc) (42 mmol), NaBH$_4$ (174 mmol), THF (260 mL), water (70 mL) to yield (XIVc) (17.5 g) as a pale oil, which is used without further purification.

3-Benzyl-15β-penten-4-ylestradiol (XIVd)

Synthesized according to the procedure of (XIVa) with (XIIId) (32 mmol), NaBH$_4$ (127 mmol), THF (200 mL), water (50 mL) to yield (XIVd) (98%) as a yellow oil, which is used without further purification.

3-Benzyl-15β-vinyl-17-acetylestradiol (XVa)

Acetic anhydride (373 mmol) is added to a solution of (XIVa) (7.45 g) in pyridine (85 mL). The mixture is stirred overnight at ambient temperature and heated for an additional 3 h at 60° C. The mixture is concentrated in vacuo. The residue is taken up in a mixture of water (150 mL) and DCM (200 mL). 2 spoons of NaCl are added to improve phase separation. The layers are separated and the aq. layer is extracted with DCM (2×100 mL). The combined organic layers are dried over Na$_2$SO$_4$ and concentrated in vacuo to give (XVa) (7.9 g) as a brown oil (containing residual pyridine). Purification by automated column chromatography on the Isco-companion (100%→heptane 100% DCM) gives (XVa) (67%) as a colorless oil.

3-Benzyl-15β-allyl-17-acetylestradiol (XVb)

Synthesized according to the procedure of (XVa) from (XIVb) (31.5 mmol), Ac$_2$O (690 mmol), pyridine (160 mL) to give (XVb) (91%) as a yellow oil after column chromatography (SiO$_2$, DCM/hept.=7/3).

3-Benzyl-15β-buten-3-yl-17-acetylestradiol (XVc)

Synthesized according to the procedure of (XVa) from (XIVc) (42 mmol), Ac$_2$O (1.08 mol), pyridine (212 mL) to give (XVc) (91%) as a yellow oil after column chromatography (SiO$_2$, DCM/hept.=7/3).

3-Benzyl-15β-penten-4-nyl-17-acetylestradiol (XVd)

Synthesized according to the procedure of (XVa) from (XIVd) (31 mmol), Ac$_2$O (692 mmol), pyridine (212 mL) to give (XVd) (80%) as a white solid after column chromatography (SiO$_2$, EtOAc/hept.=1/9).

3-Benzyl-15β-(2-hydroxyethyl)-17-acetylestradiol (XVIa)

A solution of (XVa) (11 mmol) in THF (75 mL) is cooled to 10° C. After addition of 9-BBN (0.5 M in THF, 16.3 mmol) the mixture is stirred for 2 h at ambient temperature. An additional amount of 9-BBN (16 mL) is added and the mixture is stirred for another 2.5 h at ambient temperature. Diglyme (125 mL), ethanol (40 mL) and TMNO (75 mmol) are added. The mixture is heated to 150° C., while distilling off the trimethylamine, THF and ethanol with a Dean-Stark trap. The mixture is stirred for 1 h at 150° C. After cooling to ambient temperature, water (250 mL) and EtOAc (250 mL) are added. The layers are separated and the aq. layer is extracted with EtOAc (2×250 mL). The combined organic layers are ished with 10% Na$_2$S$_2$O$_5$ (250 mL) and dried over Na₂SO₄. The layer is concentrated in vacuo. The residue is heated in high vacuum at 200° C. to remove residual volatiles to give crude (XVIa) (6.3 g).

Purification by automated column chromatography on the Isco-companion gives (XVIa) (41%) as a yellow oil.

3-Benzyl-15β-(3-hydroxypropyl)-17-acetylestradiol (XVIb)

Synthesized according to the procedure of (XVIa) from (XVb) (47.2 mmol), THF (260 mL), 9-BBN 0.5 M in THF (70 mmol), Me₃NO.H₂O (323 mmol), EtOH (140 mL), diglyme (430 mL) to yield (XVIb) (86%) as a pale oil after column chromatography (SiO₂, DCM/MeOH=97/3).

3-Benzyl-15β-(4-hydroxybutyl)-17-acetylestradiol (XVIc)

Synthesized according to the procedure of (XVIa) from (XVc) (38 mmol), THF (350 mL), 9-BBN 0.5 M in THF (57.5 mmol), Me₃NO.H₂O (267 mmol), EtOH (118 mL), diglyme (431 mL) to yield (XVIc) (83%) as a pale oil after column chromatography (SiO₂, DCM/MeOH=97/3).

3-Benzyl-15β-(5-hydroxypentyl)-17-acetylestradiol (XVId)

Synthesized according to the procedure of (XVIa) from (XVd) (30 mmol), THF (150 mL), 9-BBN 0.5 M in THF (45 mmol), Me₃NO.H₂O (211 mmol), EtOH (80 mL), diglyme (300 mL) to yield compound (XVId) (89%) as a yellow oil after column chromatography (SiO₂, EtOAc/MeOH=17/3).

3-Benzyl-15β-(2-O-mesylethyl)-17-acetylestradiol (XVIIa)

To a solution of alcohol (XVIa) (4.6 mmol) in THF (50 mL) are added Et₃N (5.5 mmol) and methanesulfonylchloride (5.5 mmol). The resulting suspension is stirred overnight. The mixture is extracted with EtOAc (50 mL). The organic layer is ished with sat. NaHCO₃ (50 mL). The combined aq. layers are extracted with EtOAc (2×75 mL). The combined organic layers are ished with brine. The organic layer is dried over Na₂SO₄ and concentrated in vacuo to give (XVIIa) (58%) as an oil.

3-Benzyl-15β-(3-O-mesylpropyl)-17-acetylestradiol (XVIIb)

Synthesized according to the procedure of (XVIIa) from (XVIb) (40.6 mmol), MsCl (48.8 mmol), NEt₃ (48.8 mmol), THF (400 mL) to yield (XVIIb) (96%) as a pale solid, that is used without further purification.

3-Benzyl-15β-(4-O-mesylbutyl)-17-acetylestradiol (XVIIc)

Synthesized according to the procedure of (XVIIa) from (XVIc) (31.7 mmol), MsCl (38 mmol), NEt₃ (38 mmol), THF (160 mL). Yielding (XVIIc) (18.1 g) as a pale solid, that is used without further purification.

3-Benzyl-15β-(5-O-mesylpentyl)-17-acetylestradiol (XVId)

Synthesized according to the procedure of (XVIIa) from (XVId) (24 mmol), MsCl (30 mmol), NEt₃ (30 mmol), THF (100 mL) to yield (XVIId) (14.0 g) as a yellow oil, that is used without further purification.

3-Benzyl-15β-(2-azido-ethyl)-17-acetylestradiol (XVIIIa)

Sodium azide (8.1 mmol) is added to a solution of (XVIIa) (2.6 mmol) in DMF (25 mL). The mixture is heated at 70° C. for 4 h. The reaction is cooled to ambient temperature and poured out over ice-water (500 mL). The mixture is extracted with EtOAc (3×250 mL). The combined organic layers are ished with brine, dried over Na₂SO₄ and concentrated in vacuo to give crude (XVIIIa) (1.35 g). Purification by column chromatography (SiO₂, DCM) gave (XVIIa) (79%) as a colorless oil, which solidified upon standing.

3-Benzyl-15β-(3-azido-propyl)-17-acetylestradiol (XVIIIb)

Synthesized according to the procedure of (XVIIIa) from (XVIIb) (39 mmol), NaN₃ (117 mmol), DMF (430 mL) to yield (XVIIIb) (88%) as a pale solid after column chromatography (SiO₂, DCM).

3-Benzyl-15β-(4-azido-butyl)-17-acetylestradiol (XVIIIc)

Synthesized according to the procedure of (XVIIIa) from (XVIIc) (18.1 g, max 31.7 mmol), NaN₃ (98.6 mmol), DMF (350 mL) to yield (XVIIIc) (85%) as a yellow oil after column chromatography (SiO₂, DCM).

3-Benzyl-15β-(5-azido-pentyl)-17-acetylestradiol (XVIIId)

Synthesized according to the procedure of (XVIIIa) from (XVIId) (14 g), NaN₃ (50 mmol), DMF (120 mL) to yield (XVIIId) (87%).

3-Benzyl-15β-(2-azido-ethyl)-estradiol (XIXa)

To a solution of (XVIIIa) (2.1 mmol) in THF (12 mL) are added MeOH (10 mL) and a KOH (10 mL, 5%). The mixture is stirred for 3 h at 55° C. The reaction is monitored by TLC. The mixture is cooled to ambient temperature and extracted with EtOAc (50 mL). The organic layer is ished with water (50 mL). The combined aq. layers are extracted with EtOAc (2×50 mL). The combined organic layers are ished with brine, dried over Na₂SO₄ and concentrated in vacuo to give (XIXa) (95%) as a oil, which is used without further purification.

3-Benzyl-15β-(3-azido-propyl)-estradiol (XIXb)

Synthesized according to the procedure of (XIXa) from (XVIIIb) (32.2 mmol), KOH, (143 mmol), MeOH (160 mL), THF (175 mL), H₂O (160 mL) to yield (XIXb) (14.7 g) as a yellow oil, which is used without further purification.

3-Benzyl-15β-(4-azido-butyl)-estradiol (XIXc)

Synthesized according to the procedure of (XIXa) from (XVIIIc) (27 mmol), KOH, (117 mmol), MeOH (130 mL), THF (145 mL), H₂O (130 mL) to yield (XIXc) (13.4 g) as a yellow oil, which is used without further purification.

3-Benzyl-15β-(5-azido-pentyl)-estradiol (XIXd)

Synthesized according to the procedure of (XIXa) from (XVIIId) (21 mmol), KOH, (94 mmol), MeOH (50 mL), THF (120 mL), H$_2$O (105 mL) to yield (XIXd) (95%) as a pale oil, which is used without further purification.

3-Benzyl-15β-(2-azido-ethyl)-estrone (XII-IIa)

NMO (6 mmol) and TPAP (0.2 mmol) are added to a solution of (XIXa) (2.0 mmol) in acetone (25 mL). The mixture is stirred for 3 h at ambient temperature. The mixture is filtered over Celite® and the filtercake is ished with acetone (2×50 mL). The filtrate is concentrated in vacuo to give (XII-IIa) (730 mg) as a brown solid. Purification by filtration over SiO$_2$ with DCM gives (XII-IIa) (66%) as a white solid.

3-Benzyl-15β-(3-azido-propyl)-estrone (XII-IIb)

Synthesized according to the procedure of (XII-IIa) from (XIXb) (14.7 g), TPAP, (3.3 mmol), NMO (99.1 mmol), acetone (300 mL) to yield (XII-IIb) (86%) as a pale solid.

3-Benzyl-15β-(4-azido-butyl)-estrone (XII-IIc)

Synthesized according to the procedure of (XII-IIa) from (XIXc) (13.5 g), TPAP, (2.70 mmol), NMO (81 mmol), acetone (260 mL) to yield (XII-IIc) (85%) as an off white solid after filtration over SiO$_2$ with DCM as eluent.

3-Benzyl-15β-(5-azido-pentyl)-estrone (XII-IId)

Synthesized according to the procedure of (XII-IIa) from (XIXd) (20 mmol), TPAP, (2 mmol), NMO (61 mmol), acetone (200 mL) to yield (XII-IId) (67%) as a white solid after column chromatography (SiO$_2$, EtOAc/hept.=1/9→3/17).

Alternatively, certain intermediates with X and Y=O of formula (I) compounds may be prepared stereoselectively via the following route (scheme 3).

scheme 3: prepartion route azide intermediate (XII-III), R$^7$ as defined above, I = 3-5 and PG is a common protecting group like benzyl

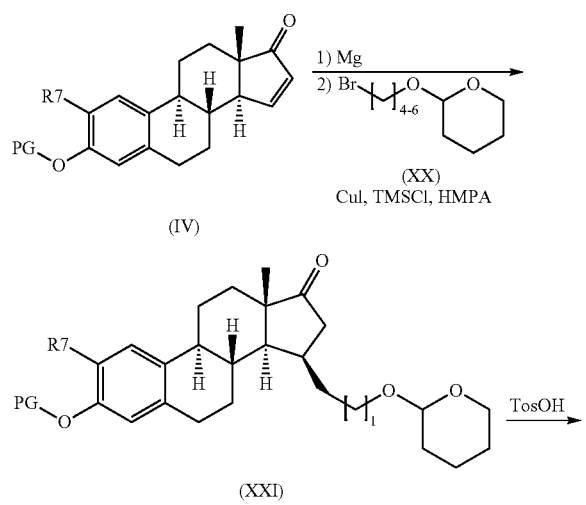

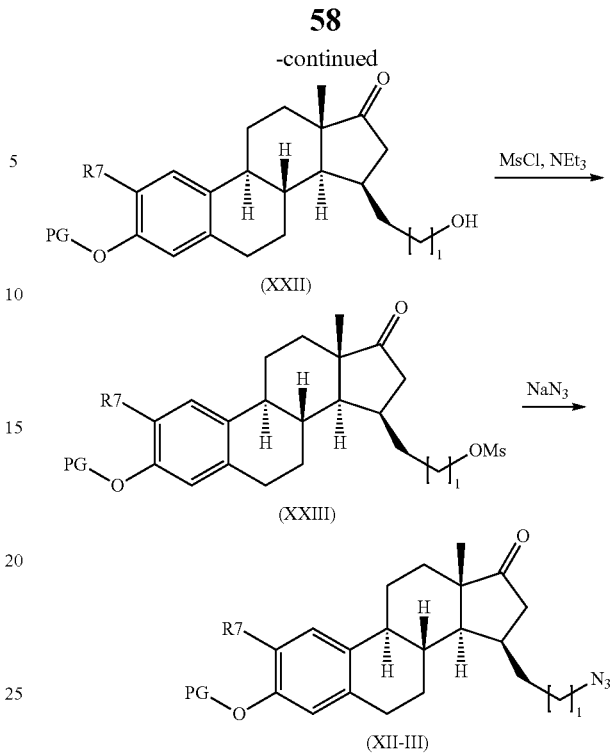

The estrone (IV) may be converted in a Grignard reaction into the corresponding alkoxy-THP derivative (XXI). Without protection of the ketone, it is further hydroxylated (XXII) and then mesylated (XVII). After azidation of the mesyl-protected alcohol (XVII), the ketone (XVIII) is deprotected in two steps to obtain the desired azide intermediate (XII-II).

Synthesis of Selected Examples of XII-III with R$^1$=benzyl, R$^7$=H and I=5

2-(6-Bromo-hexyloxy)-tetrahydro-pyran (XX)

Bromohexanol (54.67 g) is dissolved in TBME (250 mL) and dried over Na$_2$SO$_4$. After filtration, TsOH (0.6 mmol) is added and the solution is cooled in an ice bath. 3,4-Dihydropyran (394 mmol) is added dropwise, while maintaining the temperature around 2-3° C. After complete addition the reaction mixture is allowed to reach ambient temperature overnight. The mixture is ished with sat. NaHCO$_3$ (2×200 mL). The aqueous layer is extracted with TBME (200 mL) and the combined organic layers are ished with brine (200 mL). After drying over Na$_2$SO$_4$ (containing some K$_2$CO$_3$), the solvent is evaporated to yield (XX) as a colourless oil (90%), which is stored at 4° C. over K$_2$CO$_3$ and is used without further purification.

3-Benzyl-15β-[6-(tetrahydro-pyran-2-yloxy)-hexyl]-estrone (XXIa)

Magnesium turnings (5.9 eq.) are activated by I$_2$ and two drops of pure (XX). Then (XX) (4 eq.) in THF (dry, 400 mL) is added dropwise at such a rate that reflux is maintained. The reaction mixture is heated up to prevent the reaction from stopping. After complete addition the mixture is refluxed for 45 minutes and then cooled to ambient temperature. The Grignard reagent is transferred into a flask which contained CuI (0.35 eq.) and HMPA (4.3 eq.); then cooled to −40° C. Enone (IV) (67 mmol) and TMSCl (2.2 eq.) in THF (dry, 400 mL) are added dropwise at a temperature between −45° C. and −40° C. After complete addition, the black reaction mixture is allowed to warm up to ambient temperature and stirred overnight. The mixture is then poured out over an ice cold solution of NH$_4$Cl (10%, 500 mL). The layers are separated and the aqueous layer is extracted with EtOAc (2×400 mL). The combined organic layers are ished with 1 M HCl solution (2×200 mL), 25% NH$_{3(aq.)}$ solution, brine (200 mL) and dried over Na$_2$SO$_4$. The solvent is evaporated and the brown oil obtained (XXIa) (>100%) is used without purification in the following step.

3-Benzyl-15β-(6-hydroxyhexyl)-estrone (XXIIa)

The crude steroid (XXIa) (73.54 g) is dissolved in MeOH (240 mL) and TsOH (0.62 eq. compared to (IV)) is added. The orange solution is stirred at ambient temperature overnight. Water (150 mL) is added and the solvent is evaporated. More water (70 mL) is added and the mixture is extracted with EtOAc (250 mL, 200 mL). The organic layers are dried on Na$_2$SO$_4$ and the solvent is evaporated. The remaining brown oil (50 g) is purified by column chromatography (SiO$_2$, heptane/EtOAc=3/7), yielding (XXII) as a yellow oil (20.60 g, 0.045 mol, 67% over 2 steps). As some impurities are still visible on NMR, a recrystallization (EtOAc/heptane=1/3) is performed and (XXII) is obtained as a white solid (26 mmol).

3-Benzyl-15β-(6-O-mesylhexyl)-estrone (XXIIIa)

(XXIIa) (43 mmol) is dissolved in THF (250 mL); triethylamine (1.5 eq.) and methanesulfonyl chloride (1.5 eq.) are added. After stirring for two hours at ambient temperature the conversion is complete and EtOAc is added (500 mL). The mixture is ished with water (250 mL) and with a sat. NaHCO$_3$ (400 mL). The combined aqueous layers are extracted with EtOAc (400 mL); the organic layers are ished with brine (250 mL), dried over Na$_2$SO$_4$ and concentrated in vacuo affording 23 g as a yellow oil (XXIIIa), which is used in the following steps without further purification.

3-Benzyl-15β-(6-O-azido-hexyl)-estrone (XIIIa)

(XXIIIa) (43 mmol) is dissolved in DMF (230 mL) and sodium azide (2 eq.) is added. The mixture is stirred at 70° C. for 3 hours and then to cool to ambient temperature. The mixture is diluted with EtOAc (600 mL) and ished with water (400 mL, 300 mL). The aqueous layers are extracted with EtOAc (400 mL) and the combined organic layers are ished with brine (300 mL). After drying the organic phase over Na$_2$SO$_4$ and filtration, the solvent is removed at reduced pressure. The last traces of solvents are removed at high vacuum (7 mbar) at 65° C. and (XII-IIIa) is obtained as an orange oil (97%).

A synthesis route of certain azide intermediates (XII) with R$^7$=H of formula (I) starting from the respective alcohols is described in patent application WO 2005/047303 and with R$^7$≠H in the PCT application WO 2006/125800.

Synthesis Scheme for the Compounds of Formula (Ix) of the Inventions

Certain compounds of formula Ix can be prepared via the following route:

scheme 4: preparation route I of compounds of formula (Ix) with configuration at C$_{15}$ being either alpha or beta and X, Y, R$^2$, R$^7$ and n as defined above, library synthesis

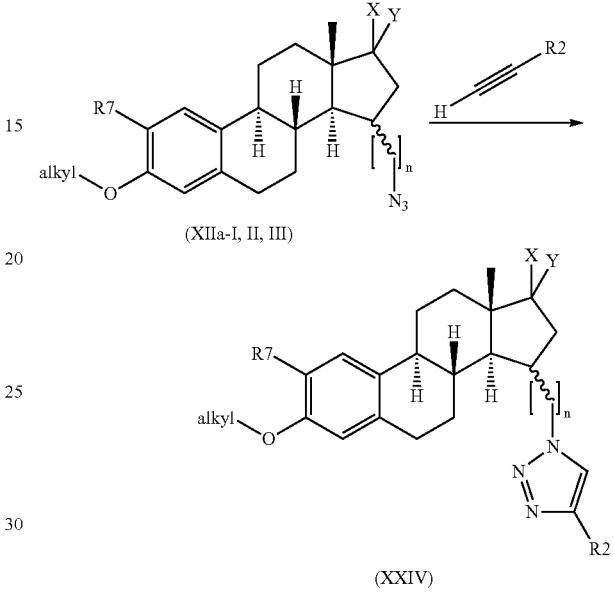

(XIIa-I, II, III)

(XXIV)

1,4 disubstituted triazoles (XXIV) can be synthesized by a copper catalyzed coupling of an azide (XIIa-I, II, III) with a terminal alkyne in the presence of sodium ascorbate as reducing agent and a minor amount of water (see e.g. V. V. Rostovtsev, L. G. Green, V. V. Fokin, K. B. Sharpless, "A Stepwise Huisgen Cycloaddition Process: Copper(I)-Catalyzed Regioselective Ligation of Azides and Terminal Alkynes" Angew. Chem., 2002, 41(14), 2596-2599 and WO 2003/101972). A possible alternative is the copper(I) catalysed method at room temperature or higher (e.g. ≦80° C.). Different copper sources, with copper in different oxidation states such as 0, I or II may be used as well, non-limiting examples of which are CuX (with X=Cl, Br, I), CuOAc and Cu (see e.g. WO 2006/063585). Typically, an amount of Cu-source in the range 0.1 to 10% by mole relative to the amount of the alkyne or azide is used at low temperatures in solvents such as MeOH, EtOH, tert-BuOH 1,4-dioxane, AcN, DMSO, acetone, DMF, NMP or THF. The above coupling may also be performed thermally thus without a catalyst as Cu). However, this process may also lead to 1,5-disubstituted triazoles.

Synthesis of XXIV 0.05 mmol Azide (XIIa-I, II, III), 0.05 mmol alkyne derivatives, approx. 1 mg sodium ascorbate and 0.5 mg CuSO$_4$ are added together and dissolved in 4 ml water/ethanol (2:1). After irradiation of the samples in a microwave oven (sealed 10 ml tubes, Personal Chemistry, Emrys Optimizer) for 300 sec. at 120° C. the reaction mixture is cooled to ambient temperature and diluted with 4 ml ethylacetate and extracted with brine. The organic layer is separated and after drying over Na$_2$SO$_4$ evaporated to dryness in a vacuum centrifuge. After quality control by LC-MS the compounds are used for biological testing Alternatively, compounds of formula (Ix) can be prepared via the following route (scheme 5):

scheme 5: preparation route I of compounds of formula (Ix) with configuration at $C_{15}$ being either alpha of beta and $R^2$, $R^7$ and n as defined above, library synthesis

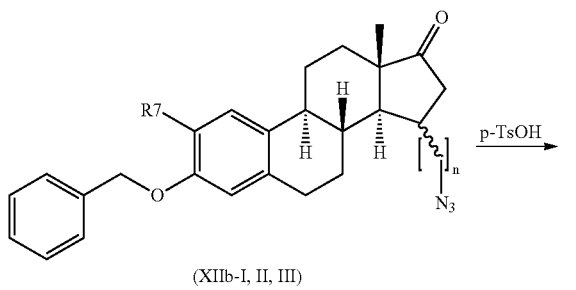

(XIIb-I, II, III)

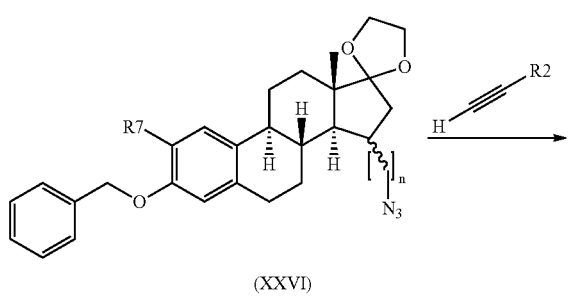

(XXVI)

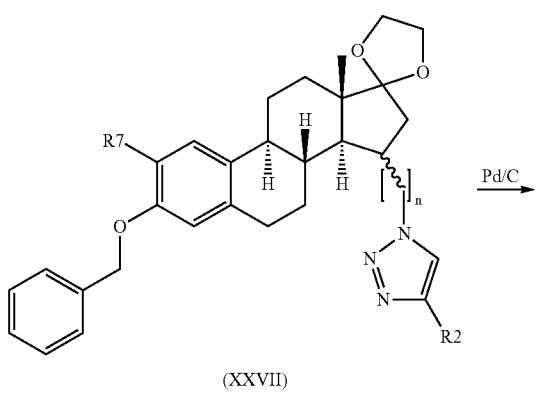

(XXVII)

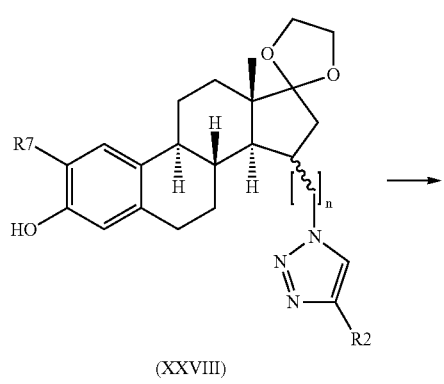

(XXVIII)

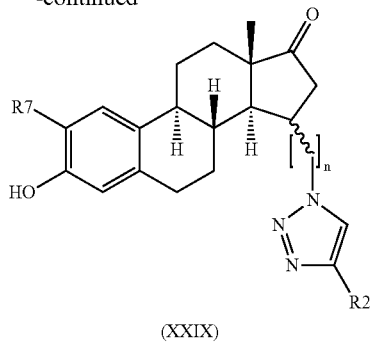

(XXIX)

Synthesis of XXIX

Compounds XXVI

Azide (XIIb-I, II, III) (25 mmol), triethylortoformate (7.5 eq.), ethylene glycol (11 eq.) and TsOH (0.06 eq.) are stirred at 40° C. overnight. The reaction mixture is poured in ice/water (1 L) containing pyridine (5 mL) and stirred for 2 h. The mixture is extracted with EtOAc (3×350 mL) and the combined organic layers are washed with water (300 ml) and brine (300 mL), dried over $Na_2SO_4$ and concentrated to give crude (XXVI), which is purified twice by column chromatography over $SiO_2$ (1 L and 700 mL, DCM) to give (XXVI).

Compounds XXVII 0.09 mmol Azide XXVI, 0.09 mmol alkyne derivatives, approx. 2 mg sodium ascorbate and 1 mg $CuSO_4$ are added together and dissolved in 5 ml water/ethanol (2:1). After irradiation of the samples in a microwave oven (sealed 10 ml tubes, Personal Chemistry, Emrys Optimizer) for 300 sec. at 120° C. the reaction mixture is cooled to ambient temperature and diluted with 4 ml ethylacetate and extracted with brine. The organic layer was separated and after drying over $Na_2SO_4$ evaporated to dryness in a vacuum centrifuge.

After quality control by LC-MS the compounds (XXVII) are used for further synthesis without purification.

Compounds XXVIII

To the triazol derivatives (XXVII) 0.75 mmol ammonium formiate 50 mg Pd/C (10%) and 5 ml methanol are added. After irradiation of the samples in a microwave oven (sealed 10 ml tubes, Personal Chemistry, Emrys Optimizer) for 120 sec. at 90° C. the reaction mixture is cooled to ambient temperature and filtrated over celtite and washed twice with 1 ml methanol. The methanol solution is evaporated to dryness in a vacuum centrifuge. The crude product is separated between 4 ml EtOAc and 4 ml water. The organic layer is dried over $Na_2SO_4$ and evaporated to dryness in a vacuum centrifuge.

After quality control by LC-MS the compounds (XXVIII) are used for further synthesis without purification.

Compounds XXIX

To the debenzylated triazol derivatives (XXVIII) 50 mg polymer bound para toluene suolfonic acid and 5 ml methanol/water (1:1) is added. After irradiation of the samples in a microwave oven (sealed 10 ml tubes, Personal Chemistry, Emrys Optimizer) for 300 sec. at 150° C. the reaction mixture is cooled to ambient temperature and the methanol is evaporated in a vacuum centrifuge. To the residue 4 ml EtOAc and 4 ml water are added. The organic layer is separated, dried over $Na_2SO_4$ and evaporated to dryness in a vacuum centrifuge.

After quality control by LC-MS the compounds are used for biological testing

Selected Examples for Preparation of XXVI with R⁷=H

Benzyl-5-(3-Azido-propyl)-3-hydroxy-13-methyl-6,7,8,9,11,12,13,14,15,16-decahydro-cyclopenta[a]phenanthren-17-one ethylene glycol acetal (XXVI-Ia)

Ketone (XII-Ia) (25 mmol), triethylortoformate (7.5 eq.), ethylene glycol (11 eq.) and TsOH (0.06 eq.) are stirred at 40° C. overnight. The reaction mixture is poured in ice/water (1 L) containing pyridine (5 mL) and stirred for 2 h. The mixture is extracted with EtOAc (3×350 mL) and the combined organic layers are washed with water (300 ml) and brine (300 mL), dried over $Na_2SO_4$ and concentrated to give crude (XXVI-Ia) (15.2 g) as a yellow oil. The crude oil was purified twice by column chromatography over $SiO_2$ (1 L and 700 mL, DCM) to give (XXVI-Ia) (73%) as a light yellow oil. At low temperature a white foam is formed which melts at RT.

1-{2-[3-(benzyloxy)-13-methyl-6,7,8,9,11,12,13,14,15,16-decahydrospiro[cyclopenta[a]phenanthrene-17,2'-[1,3]dioxolan]-15-yl]ethyl}triaza-1,2-dien-2-ium (XXVI-IIa)

Ethylene glycol (3 mL) and TsOH (0.05 mmol) are added to a suspension of (XII-IIa) (1.3 mmol) in triethyl orthoformate (10 mL). The reaction mixture is stirred at 55° C. (external) overnight. The reaction mixture is poured out over a mixture of ice-water (90 mL) and pyridine (0.3 mL) and stirred for 3 h. The mixture is extracted with EtOAc (3×50 mL). The combined organic layers are extensively washed with water (9×75 mL) and brine. The organic layer is dried over $Na_2SO_4$ and concentrated in vacuo to give (XXVI-IIa) (910 mg) as an oil. Purification by column chromatography ($SiO_2$, DCM) gives (XXVI-IIa) (67%) as a colorless oil.

1-{3-[3-(benzyloxy)-13-methyl-6,7,8,9,11,12,13,14,15,16-decahydrospiro[cyclopenta[a]phenanthrene-17,2'-[1,3]dioxolan]-15-yl]propyl}triaza-1,2-dien-2-ium (XXVI-IIb)

Synthesized according to the procedure of (XXVI-IIa) from (XII-IIb) (27.5 mmol), triethyl orthoformate (165.2 mmol), ethylene glycol (220 mmol), TsOH (2.75 mmol) to yield (XXVI-IIb) (73%) as a pale oil after column chromatography ($SiO_2$, DCM).

1-{4-[3-(benzyloxy)-13-methyl-6,7,8,9,11,12,13,14,15,16-decahydrospiro[cyclopenta[a]phenanthrene-17,2'-[1,3]dioxolan]-15-yl]butyl}triaza-1,2-dien-2-ium (XXVI-IIc)

Synthesized according to the procedure of (XXVI-IIa) from (XII-IIc) (22.9 mmol), triethyl orthoformate (169 mmol), ethylene glycol (250 mmol), TsOH (1.35 mmol) to yield (XXVI-IIc) (95%) as a pale oil after column chromatography ($SiO_2$, DCM).

1-{5-[3-(benzyloxy)-13-methyl-6,7,8,9,11,12,13,14,15,16-decahydrospiro[cyclopenta[a]phenanthrene-17,2'-[1,3]dioxolan]-15-yl]pentyl}triaza-1,2-dien-2-ium (XXVI-IId)

Synthesized according to the procedure of (XXVI-IIa) from (XII-IId) (14 mmol), triethyl orthoformate (82 mmol), ethylene glycol (109 mmol), TsOH (1 mmol) to yield (XXVI-IId) (99%) as a yellow oil.

1-{6-[3-(benzyloxy)-13-methyl-6,7,8,9,11,12,13,14,15,16-decahydrospiro[cyclopenta[a]phenanthrene-17,2'-[1,3]dioxolan]-15-yl]hexyl}triaza-1,2-dien-2-ium (XXVI-IIIa)

Synthesized according to the procedure (XXVI-IIa) from (XII-IIa) (41 mmol), triethyl orthoformate (273 mmol), ethylene glycol (332 mmol), TsOH (4 mmol) to yield (XXVI-IIIa) (22 g) as a yellow oil.

Selected Examples for Preparation of XXIX with R⁷=H

I. With R²=m-OH-phenyl

3-Benzyloxy-15-[3-(4-m-hydroxyphenyl-[1,2,3]triazol-1-yl)-propyl]-13-methyl-6,7,8,9,11,12,13,14,15,16-decahydro-cyclopenta[a]phenanthren-17-one ethylene glycol acetal (XXVII-Ia-I)

Azide (XXVI-Ia) (1.4 mmol), 3-hydroxyphenylacetylene (2 eq.), L-ascorbic acid sodium salt (0.1 eq.) and $CuSO_4.5H_2O$ (0.01 eq.) are heated in a microwave in a 2:1 water:EtOH mixture (8 mL) at 120° C. for 10 min. The reaction mixture is transferred to a flask with MeOH and the alcohols are removed by evaporation. Water (30 mL) is added and the mixture is extrated with EtOAc (3×50 mL). The combined organic layers are washed with brine (50 mL) dried over $Na_2SO_4$ and concentrated to give 948 mg crude (XXVII-Ia-I) as an orange oil. This is purified by automated column chromatrography (Rf=0.27 with DCM w. 2.5% MeOH) to give (XXVII-Ia-I) (43%) as a white foam.

3-Hydroxy-15-[3-(4-m-hydroxyphenyl-[1,2,3]triazol-1-yl)-propyl]-13-methyl-6,7,8,9,11,12,13,14,15,16-decahydro-cyclopenta[a]phenanthren-17-one ethylene glycol acetal (XXVIII-Ia-I)

(XXVII-Ia-I) (1.1 mmol), $NH_4OOCH$ (7.2 eq.) and 10% Pd/C (650 mg) in MeOH (25 mL) are heated in the microwave for 3 min. at 90° C. After cooling, the mixture is filtered over Celite®, and the Celite® is washed with MeOH (200 mL). The filtrate is concentrated and the residue is taken up in EtOAc (200 mL) and washed with water (30 mL). The organic layer is dried over $Na_2SO_4$ and concentrated to give (XXVIII-Ia-I) (81%) as a white foam.

3-Hydroxy-15-[3-(4-m-hydroxyphenyl-[1,2,3]triazol-1-yl)-propyl]-13-methyl-6,7,8,9,11,12,13,14,15,16-decahydro-cyclopenta[a]phenanthren-17-one (XXIX-Ia-I), Further Referred to as Compound 22

(XXVIII-Ia-I) (0.89 mmol) and a few mg of TsOH in MeOH:water 1:1 (20 mL) with a few drops of acetone are heated in the microwave for 5 min. at 150° C. The mixture is transferred to a flask and MeOH was evaporated. To the residue is added water (30 mL) and a few drops $NaHCO_3$ and the mixture is extracted with EtOAc (3×75 mL). The combined organic layers are washed with brine (30 mL), dried over $Na_2SO_4$ and concentrated to give (XXIX-Ia-I) (88%) as an off white solid.

¹H-NMR ($CD_3OD/\delta$/ppm): 0.75, m, 1H, 1.0, s, 3H, 1.2-1.6, m, 7H, 1.8, m, 3H, 2.0, m, 4H, 2.2-2.4, m, 3H, 2.6-2.9, m, 3H, 4.5, t, 2H, 6.4, m, 1H, 6.5, dd, 1H, 7.1, d, 1H, 7.3, m, 3H, 8.3, s, 1H

II. With R²=p-Me-phenyl

3-Benzyloxy-15-[3-(4-p-tolyl-[1,2,3]triazol-1-yl)-propyl]-13-methyl-6,7,8,9,11,12,13,14,15,16-decahydro-cyclopenta[a]phenanthren-17-one ethylene glycol acetal (XXVII-Ia-II)

Azide (XXVI-Ia) (2.9 mmol), p-tolylacetylene (2 eq.), L-ascorbic acid sodium salt (0.1 eq.) and CuSO$_4$.5H$_2$O (0.01 eq.) are heated in a microwave in a 2:1 water:EtOH mixture (16 mL) at 120° C. for 10 min. The reaction mixture is transferred to a flask with MeOH and EtOAc. The MeOH, EtOH and EtOAc are removed by evaporation and water (30 mL) is added to the residue, which is extracted with EtOAc (3×50 mL). The combined organic layers are washed with brine (50 mL) dried over Na$_2$SO$_4$ and concentrated to give 1.68 g of (XXVII-Ia-II) as a light yellow solid. This was purified by automated column chromatography (Rf=0.32 with DCM w. 2.5% IPA) to give pure (XXVII-Ia-II) (83%) as a white foam.

3-Hydroxy-15-[3-(4-p-tolyl-[1,2,3]triazol-1-yl)-propyl]-13-methyl-6,7,8,9,11,12,13,14,15,16-decahydro-cyclopenta[a]phenanthren-17-one ethylene glycol acetal (XXVIII-Ia-II)

(XXVII-Ia-II) (2.4 mmol), NH$_4$OOCH (7.2 eq.) and 10% Pd/C (1.4 g) are suspended in MeOH (25 mL) and the mixture is heated in the microwave for 3 min. at 90° C. After filtration over Celite®, the Celite® is washed with 300 mL MeOH and the filtrate is concentrated. The residue is taken up in 250 mL EtOAc and washed with water (50 mL). The organic layer is dried over Na$_2$SO$_4$ and concentrated to give ca. 300 mg of the above product. The Celite® is washed 200 mL DCM and the filtrate is concentrated. The residue is taken up in 250 mL EtOAc and washed with water (50 mL). The organic layer is dried over Na$_2$SO$_4$, combined with the EtOAc fraction and concentrated to give 956 mg of a mixture of product and starting material. This is purified by automated column chromatography (Rf=0.42 with EtOAc:heptane 1:1) to give (XXVIII-Ia-II) (30%) as a white solid.

3-Hydroxy-15-[3-(4-p-tolyl-[1,2,3]triazol-1-yl)-propyl]-13-methyl-6,7,8,9,11,12,13,14,15,16-decahydro-cyclopenta[a]phenanthren-17-one (XXIX-Ia-II), Further Referred to as Compound 25

(XXVIII-Ia-II) (0.71 mmol) and a few mg of TsOH is heated in 15 mL of MeOH:water (1:1) and a few drops of acetone in the microwave for 5 min. at 150° C. The reaction mixture is transferred to a flask and the MeOH is removed. Water (30 mL) and a few drops of sat. NaHCO$_3$ are added. The mixture is extracted with EtOAc (75 mL) and DCM (2×75 mL). The combined organic layers are dried over Na$_2$SO$_4$, concentrated to yield (XXIX-Ia-II) (73%).
$^1$H-NMR (CDCl$_3$/δ/ppm): 1.0, s, 3H, 1.3, m, 3H, 1.5, m, 1H, 1.7, m, 4H, 1.8-2.1, m, 4H, 2.2, m, 2H, 2.4, s, 4H, 2.8, m, 3H, 4.4, t, 2H, 4.6, s, 1H, 6.5, m, 1H, 6.6, dd, 1H, 7.1, d, 1H, 7.2, m, 2H, 7.7, m, 3H

III. With R²=p-MeO-phenyl

3-Benzyloxy-15-[3-(4-O-anisoyl-[1,2,3]triazol-1-yl)-propyl]-13-methyl-6,7,8,9,11,12,13,14,15,16-decahydro-cyclopenta[a]phenanthren-17-one ethylene glycol acetal (XXVII-Ia-III)

Azide (XXVI-Ia) (3.06 mmol), ethynyl-p-anisoyl (2 eq.), L-ascorbic acid sodium salt (0.1 eq.) and CuSO$_4$.5H$_2$O (0.01 eq.) are heated in a microwave in a 2:1 water:EtOH mixture (16 mL) at 120° C. for 10 min. The reaction mixture is transferred to a flask with EtOAc and the EtOAc and EtOH are removed by evaporation. Water (30 mL) is added and the mixture is extrated with EtOAc (3×50 mL). The combined organic layers are washed with brine (50 mL) dried over Na$_2$SO$_4$ and concentrated to give 2 g crude (XXVII-Ia-III). This was purified by automated chromatography (Rf=0.44 with DCM w. 2.5% IPA) to give the (XXVII-Ia-III) (47%) as a white solid.

3-Hydroxy-15-[3-(4-0-anisoyl-[1,2,3]triazol-1-yl)-propyl]-13-methyl-6,7,8,9,11,12,13,14,15,16-decahydro-cyclopenta[a]phenanthren-17-one ethylene glycol acetal (XXVIII-Ia-III)

(XXVII-Ia-III) (1.45 mmol), NH$_4$OOCH (7.2 eq.) and 10% Pd/C (750 mg) in MeOH (50 mL) are heated in the microwave for 5 min. at 90° C. The mixture is filtered over Celite® and the residue is washed with 100 mL MeOH and 100 mL DCM. The filtrate is concentrated and the residue is taken up in EtOAc (250 mL), washed with water (50 mL), dried over Na$_2$SO$_4$ and concentrated to give (XXVIII-Ia-III) (91%) as a colorless oil.

3-Hydroxy-15-[3-(4-O-anisoyl-[1,2,3]triazol-1-yl)-propyl]-13-methyl-6,7,8,9,11,12,13,14,15,16-decahydro-cyclopenta[a]phenanthren-17-one (XXIXI-Ia-II), Further Referred to as Compound 20

(XXVIII-Ia-III) (1.45 mmol) and TsOH (few mg) in 1:1 water:MeOH (30 mL) containing a few drops acetone are heated in the microwave at 150° C. for 300 sec. The reaction mixture is transferred to a flask and MeOH is removed by evaporation. A few drops of sat. NaHCO$_3$ and water (30 mL) are added to the residue and the resulting mixture is extracted with EtOAc (3×50 mL). The combined organic layers are washed with brine (50 mL), dried over Na$_2$SO$_4$ and concentrated to give a mixture of (XXVIII-Ia-III) and (XXIXI-Ia-III) (492 mg) as a white foam. This is suspended in 1:1 water:MeOH (30 mL) containing a few drops acetone, and a few mg of TsOH is added. The mixture is heated in the microwave at 150° C. for 300 sec. The reaction mixture is transferred to a flask and MeOH is removed by evaporation. A few drops of sat. NaHCO$_3$ and water (30 mL) are added to the residue and the resulting mixture is extracted with EtOAc (50 mL) and DCM (2×50 mL). The combined organic layers are dried over Na$_2$SO$_4$ and concentrated to yield (XXIXI-Ia-III).
$^1$H-NMR (CDCl$_3$/δ/ppm): 1.0, s, 3H, 1.30, m, 2H, 1.4-1.60, m, 3H, 1.80, m, 2H, 1.8-2.10, m, 5H, 2.1-2.40, m, 3H, 2.80, m, 3H, 3.80, s, 3H, 4.40, m, 2H, 4.70, s, 1H, 6.50, m, 1H, 6.60, dd, 1H, 7.00, d, 2H, 7.10, d, 1H, 7.70, s, 1H, 7.80, d, 2H

IV. With R²=i-butyl

3-Benzyloxy-15-[3-(4-isobutyl-[1,2,3]triazol-1-yl)-propyl]-13-methyl-6,7,8,9,11,12,13,14,15,16-decahydro-cyclopenta[a]phenanthren-17-one ethylene glycol acetal (XXVII-Ia-IV)

Azide (XXVI-Ia) (1.88 mmol), 4-methyl-1-pentyne (1 eq.), L-ascorbic acid sodium salt (0.1 eq.) and CuSO$_4$.5H$_2$O (0.01 eq.) are heated in a microwave in a 2:1 water:EtOH mixture (8 mL) at 120° C. for 300 sec. The reaction mixture is transferred to a flask with MeOH and the MeOH and EtOH are removed by evaporation. Water (30 mL) is added and the mixture is extrated with EtOAc (3×30 mL). The combined organic layers are washed with brine (20 mL) dried over Na₂SO₄ and concentrated to give (XXVII-Ia-IV) (76%) as a white foam.

3-Hydroxy-15-[3-(4-isobutyl-[1,2,3]triazol-1-yl)-propyl]-13-methyl-6,7,8,9,11,12,13,14,15,16-decahydro-cyclopenta[a]phenanthren-17-one ethylene glycol acetal (XXVIII-Ia-IV)

(XXVII-Ia-IV) (1.4 mmol), NH₄OOCH (7.2 eq.) and 10% Pd/C (1 g) in MeOH (28 mL) are heated in the microwave at 90° C. for 3 minutes. The reaction mixture is filtered over Celite® while still warm (which lead to some loss of material due to pressure build up) and the Celite® is flushed with MeOH (100 mL). The filtrate is concentrated and the residue taken up in EtOAc (100 mL), washed with water (20 mL), dried over Na₂SO₄ and concentrated to give (XXVIII-Ia-IV) (76%) as a light yellow oil.

3-Hydroxy-15-[3-(4-isobutyl-[1,2,3]triazol-1-yl)-propyl]-13-methyl-6,7,8,9,11,12,13,14,15,16-decahydro-cyclopenta[a]phenanthren-17-one (XXIX-Ia-IV), Further Referred to as Compound 31

(XXVIII-Ia-IV) (0.36 mmol) and TsOH (few mg) in 1:1 water:MeOH (8 mL) containing a few drops acetone are heated in the microwave at 150° C. for 300 sec. The reaction mixture is transferred to a flask and MeOH is removed by evaporation. A few drops of sat. NaHCO₃ and water (20 mL) are added to the residue and the resulting mixture is extracted with EtOAc (3×50 mL). The combined organic layers are washed with brine (20 mL), dried over Na₂SO₄ and concentrated to give (XXIX-Ia-IV) (99%) as a colorless oil.

¹H-NMR (CDCl₃/δ/ppm): 1.0, m, 9H, 1.2, m, 3H, 1.4-1.6, m, 1H, 1.7, m, 3H, 1.8-2.1, m, 7H, 2.1-2.5, m, 4H, 2.6, d, 2H, 2.8, m, 3H, 4.3, m, 4.8, b, 1H, 6.5, m, 1H, 6.6, m, 1H, 7.1, d, 1H

V. With R²=CH₂CH₂-phenyl

3-Benzyloxy-15-[3-(4-(2-phenylethane)-[1,2,3]triazol-1-yl)-propyl]-13-methyl-6,7,8,9,11,12,13,14,15,16-decahydro-cyclopenta[a]phenanthren-17-one ethylene glycol acetal (XXVII-Ia-V)

Azide (XXVI-Ia) (2.9 mmol), 4-phenyl-1-butyne (2 eq.), L-ascorbic acid sodium salt (0.1 eq.) and CuSO₄.5H₂O (0.01 eq.) are heated in a microwave in a 2:1 water:EtOH mixture (16 mL) at 120° C. for 10 min. The reaction mixture is transferred to a flask with EtOAc and the EtOAc and EtOH are removed by evaporation. Water (30 mL) is added and the mixture is extracted with EtOAc (3×50 mL). The combined organic layers are washed with brine (50 mL) dried over Na₂SO₄ and concentrated to give crude (XXVII-Ia-V) (1.85 g) as a red oil. The oil was purified with automated column chromatography (Rf=0.43 with DCM:IPA 97.5:2.5) to give (XXVII-Ia-V) (61%) as a sticky pink foam.

3-Hydroxy-15-[3-(4-(2-phenylethane)-[1,2,3]triazol-1-yl)-propyl]-13-methyl-6,7,8,9,11,12,13,14,15,16-decahydro-cyclopenta[a]phenanthren-17-one ethylene glycol acetal (XXVIII-Ia-V)

(XXVII-Ia-V) (1.76 mmol), NH₄OOCH (7.2 eq.) and 10% Pd/C (1 g) in MeOH (50 mL) are heated in the microwave for 5 min. at 90° C. The mixture is filtered over Celite® and the residue is washed with 250 mL MeOH. The filtrate is concentrated and the residue is taken up in EtOAc (250 mL), washed with water (50 mL), dried over Na₂SO₄ and concentrated to give (XXVIII-Ia-V) (75%) as a light yellow oil which solidified as a white solid.

3-Hydroxy-15-[3-(4-(2-phenylethane)-[1,2,3]triazol-1-yl)-propyl]-13-methyl-6,7,8,9,11,12,13,14,15,16-decahydro-cyclopenta[a]phenanthren-17-one (XXIX-Ia-V), Further Referred to as Compound 16

(XXVIII-Ia-V) (1.3 mmol) and a few mg TsOH in 30 mL MeOH:water 1:1 with a few drops acetone are heated in the microwave for 5 min. at 150° C. The reaction mixture is transferred to a flask and MeOH is removed by evaporation. A few drops of sat. NaHCO₃ and water (30 mL) are added to the residue and the resulting mixture is extracted with EtOAc (3×75 mL). The combined organic layers are washed with brine (20 mL), dried over Na₂SO₄, concentrated and yielded (XXIX-Ia-V) (504 mg with a purity of >94% according to HPLC).

¹H-NMR (CDCl₃/δ/ppm): 1.0, s, 3H, 1.3, m, 3H, 1.4-1.6, m, 2H, 1.7-1.8, m, 3H, 1.8-2.0, m, 4H, 2.1-2.4, m, 3H, 2.8, m, 3H, 3.0, m, 4H, 3.3-3.8, b, 1H, 4.3, t, 2H, 6.5, m, 1H, 6.6, dd, 1H, 7.1-7.3, m, 7H

VI. With R²=CH₂CH₂—CH(CH₃)₂

3-Benzyloxy-15-[3-(4-isopentyl-[1,2,3]triazol-1-yl)-propyl]-13-methyl-6,7,8,9,11,12,13,14,15,16-decahydro-cyclopenta[a]phenanthren-17-one ethylene glycol acetal (XXVII-Ia-VI)

Azide (XXVI-Ia) (2.99 mmol), 5-methyl-1-hexyne (2 eq.), L-ascorbic acid sodium salt (0.1 eq.) and CuSO₄.5H₂O (0.01 eq.) are heated in a microwave in a 2:1 water:EtOH mixture (16 mL) at 120° C. for 10 min. The reaction mixture is transferred to a flask with EtOAc and the EtOAc and EtOH are removed by evaporation. Water (30 mL) is added and the mixture is extracted with EtOAc (3×50 mL). The combined organic layers are washed with brine (50 mL) dried over Na₂SO₄ and concentrated to give (XXVII-Ia-VI) (78%) as an orange oil.

3-hydroxy-15-[3-(4-isopentyl-[1,2,3]triazol-1-yl)-propyl]-13-methyl-6,7,8,9,11,12,13,14,15,16-decahydro-cyclopenta[a]phenanthren-17-one ethylene glycol acetal (XXVIII-Ia-VI)

(XXVII-Ia-VI) (2.35 mmol), NH₄OOCH (7.2 eq.) and 10% Pd/C (1.25 g) in MeOH (50 mL) are heated in the microwave for 5 min. at 90° C. The mixture is filtered over Celite® and the residue is washed with 250 mL MeOH. The filtrate is concentrated and the residue is taken up in EtOAc (250 mL), washed with water (50 mL), dried over Na₂SO₄ and concentrated to give (XXVIII-Ia-VI) (56%) as an orange oil.

3-hydroxy-15-[3-(4-isopentyl-[1,2,3]triazol-1-yl)-propyl]-13-methyl-6,7,8,9,11,12,13,14,15,16-decahydro-cyclopenta[a]phenanthren-17-one WH0507-07 (XXIX-Ia-VI), Further Referred to as Compound 30

(XXVIII-Ia-VI) (1.3 mmol) and a few mg TsOH in 30 mL MeOH:water 1:1 with a few drops acetone are heated in the microwave for 5 min. at 150° C. The reaction mixture is transferred to a flask and MeOH is removed by evaporation. A few drops of sat. NaHCO$_3$ and water (30 mL) are added to the residue and the resulting mixture is extracted with EtOAc (3×50 mL). The combined organic layers are washed with brine (50 mL), dried over Na$_2$SO$_4$, concentrated and yield (XXIX-Ia-VI) (295 mg, with a purity of >94% according to HPLC).

$^1$H-NMR (CDCl$_3$/δ/ppm): 1.0, d, 9H, 1.2-1.4, m, 2H, 1.4-1.6, m, 11H, 1.6-1.8, m, 2H, 1.8-2.0, m, 5H, 2.0-2.4, m, 4H, 4.4, m, 2H, 6.5, m, 1H, 6.6, dd, 1H, 7.1, d, 1H, 7.3, s, 1H Selected Examples of Compounds of Formula I 3-Hydroxy-15β-[2-(4-phenethyl-[1,2,3]triazol-1-yl)-ethyl]-estra-1,3,5(10)-trien-17-one (1)

Compound No 1 is synthesised according to scheme 5.

$^1$H-NMR (CDCl$_3$/δ/ppm): 1.00, s, 3H, 1.33-1.43, m, 1H, 1.42-1.54, m, 2H, 1.62-1.72, m, 2H, 1.74-1.80, m, 1H, 1.83-1.92, m, 2H, 2.19-2.27, m, 4H, 2.32-2.41, m, 2H, 2.78-2.89, m, 2H, 2.98-3.03, m, 2H, 3.05-3.09, m, 2H, 4.21-4.28, m, 1H, 4.36, ddd, J=13.5, 7.7, 5.3 Hz, 1H, 6.44, s, 1H, 6.63, d, J=2.7 Hz, 1H, 6.67, dd, J=8.4, 2.6 Hz, 1H, 7.08, s, 1H, 7.10, d, J=8.2 Hz, 1H, 7.15-7.20, m, 3H, 7.23-7.29, m, 2H 3-Hydroxy-15β-{2-[4-(3,5-Difluoro-phenyl)-[1,2,3]triazol-1-yl]-ethyl}-estra-1,3,5(10)-trien-17-one (5)

Compound No 5 is synthesised according to scheme 5.

$^1$H-NMR (DMSO-d$_6$/δ/ppm): 0.96, s, 3H, 1.23-1.30, m, J=17.8, 11.7, 5.6 Hz, 1H, 1.32-1.37, m, 2H, 1.58-1.66, m, 1H, 1.67-1.73, m, J=11.6, 7.0 Hz, 2H, 1.74-1.80, m, 1H, 1.91-1.99, m, J=12.6, 12.6, 6.2, 6.2 Hz, 1H, 2.11-2.30, m, 4H, 2.30-2.38, m, 1H, 2.40-2.46, m, 1H, 2.64-2.72, m, 1H, 2.77-2.85, m, 1H, 4.41-4.50, m, 2H, 6.46, d, J=2.4 Hz, 1H, 6.51, dd, J=8.2, 2.4 Hz, 1H, 7.03, d, J=8.5 Hz, 1H, 7.17-7.23, m, J=9.4, 9.4, 2.3, 2.1 Hz, 1H, 7.53-7.58, m, J=8.7, 2.3 Hz, 2H, 8.77, s, 1H, 9.00, s, 1H 3-Hydroxy-15β-{3-[4-(3,5-Difluoro-phenyl)-[1,2,3]triazol-1-yl]-propyl}-estra-1,3,5(10)-trien-17-one (18)

Compound No 18 is synthesised according to scheme 5.

$^1$H-NMR (DMSO-d$_6$/δ/ppm): 0.90, s, 3H, 1.21-1.42, m, 4H, 1.41-1.58, m, 2H, 1.61-1.73, m, 2H, 1.74-1.82, m, 1H, 1.97-2.05, m, 2H, 2.12-2.20, m, 1H, 2.21-2.29, m, 2H, 2.36-2.39, m, 2H, 2.58-2.65, m, J=9.8, 6.3, 6.0 Hz, 2H, 4.40-4.49, m, 2H, 6.37, d, J=2.4 Hz, 1H, 6.50, dd, J=8.4, 2.6 Hz, 1H, 7.01, d, J=8.2 Hz, 1H, 7.21, tt, J=9.3, 2.4 Hz, 1H, 7.56, ddd, J=15.8, 7.1, 2.1 Hz, 2H, 8.75, s, 1H, 9.00, s, 1H 4-{1-[3-(3-Methoxy-15β-17-oxo-estra-1,3,5(10)-trien-15-yl)-propyl]-1H-[1,2,3]triazol-4-yl}-benzoic acid methyl ester (89)

Compound 89 is synthesized according to scheme 5.

$^{13}$C-NMR (CD$_3$OD/δ/ppm): 17.7, q, 1C, 25.5, t, 1C, 26.8, t, 1C, 27.9, t, 1C, 29.4, t, 1C, 30.4, t, 1C, 33.9, t, 1C, 34.0, d, 1C, 36.0, d, 1C, 42.4, t, 1C, 44.5, d, 1C, 47.1, s, 1C, 50.3, t, 1C, 52.1, q, 1C, 52.7, d, 1C, 55.2, q, 1C, 111.6, d, 1C, 113.8, d, 1C, 120.2, d, 1C, 125.5, d, 2C, 126.0, d, 1C, 129.7, s, 1C, 130.3, d, 2C, 132.1, s, 1C, 134.9, s, 1C, 137.6, s, 1C, 146.9, s, 1C, 157.8, s, 1C, 166.8, s, 1C, 220.0, s, 1C $^1$H-NMR (CD$_3$OD/δ/ppm): 0.99, s, 3H, 1.38-1.49, m, 5H, 1.60-1.68, m, 4H, 1.68-1.77, m, 1H, 1.83-2.00, m, 2H, 2.06-2.18, m, 1H, 2.23-2.30, m, 1H, 2.31-2.51, m, 2H, 2.78-2.85, m, 2H, 3.77, s, 3H, 3.94, s, 3H, 4.39-4.51, dd, 2H, 6.56-6.61, s, 1H, 6.67-6.74, d, 1H, 7.13-7.19, d, 1H, 7.84, s, 1H, 7.88-7.94, d, 2H, 8.10-8.11, d, 2H Further exemplary compounds of formula (Ix) with X and Y=O, prepared by library synthesis, are listed in table 3:

TABLE 3 selected examples of compounds of formula Ix

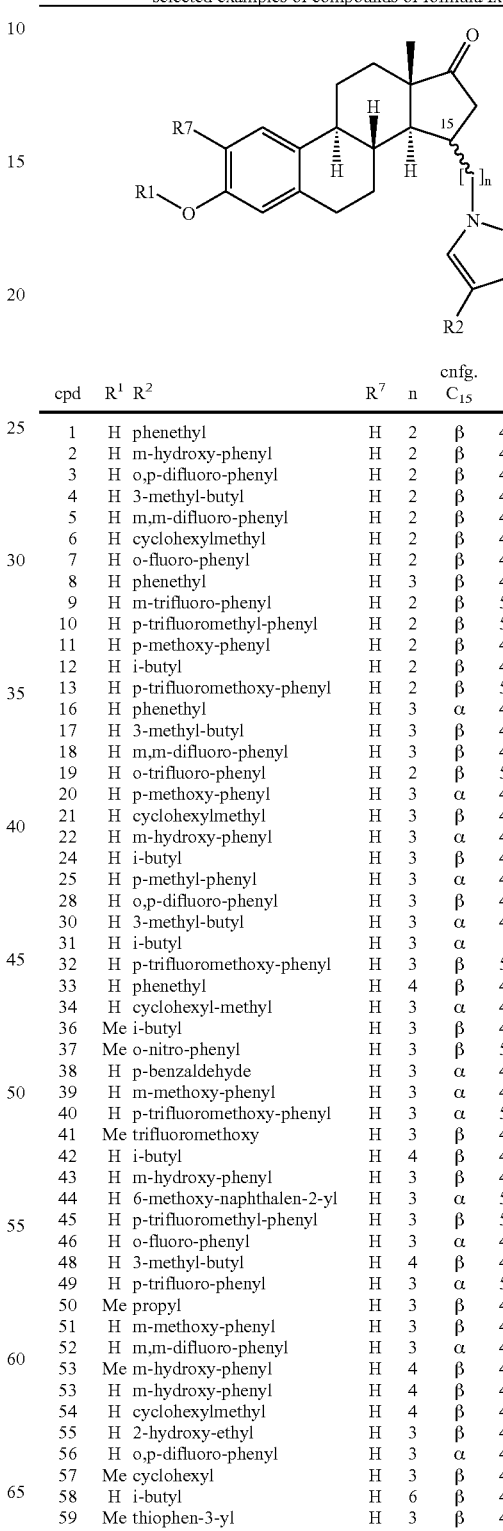

| cpd | R$^7$ | R$^2$ | R$^7$ | n | cnfg. C$_{15}$ | MS (m/z) | Rt (min) |
|---|---|---|---|---|---|---|---|
| 1 | H | phenethyl | H | 2 | β | 469.27 | 5.67 |
| 2 | H | m-hydroxy-phenyl | H | 2 | β | 457.24 | 5.1 |
| 3 | H | o,p-difluoro-phenyl | H | 2 | β | 477.22 | 5.91 |
| 4 | H | 3-methyl-butyl | H | 2 | β | 435.29 | 5.77 |
| 5 | H | m,m-difluoro-phenyl | H | 2 | β | 477.22 | 5.97 |
| 6 | H | cyclohexylmethyl | H | 2 | β | 461.3 | 6.01 |
| 7 | H | o-fluoro-phenyl | H | 2 | β | 459.23 | 5.79 |
| 8 | H | phenethyl | H | 3 | β | 483.29 | 5.84 |
| 9 | H | m-trifluoro-phenyl | H | 2 | β | 509.23 | 6.14 |
| 10 | H | p-trifluoromethyl-phenyl | H | 2 | β | 509.23 | 6.15 |
| 11 | H | p-methoxy-phenyl | H | 2 | β | 471.25 | 5.56 |
| 12 | H | i-butyl | H | 2 | β | 421.27 | 5.47 |
| 13 | H | p-trifluoromethoxy-phenyl | H | 2 | β | 525.22 | 6.2 |
| 16 | H | phenethyl | H | 3 | α | 483.29 | 5.85 |
| 17 | H | 3-methyl-butyl | H | 3 | β | 449.3 | 5.92 |
| 18 | H | m,m-difluoro-phenyl | H | 3 | β | 491.24 | 6.1 |
| 19 | H | o-trifluoro-phenyl | H | 2 | β | 509.23 | 5.91 |
| 20 | H | p-methoxy-phenyl | H | 3 | α | 485.27 | 5.72 |
| 21 | H | cyclohexylmethyl | H | 3 | β | 475.32 | 6.16 |
| 22 | H | m-hydroxy-phenyl | H | 3 | α | 471.25 | 5.26 |
| 24 | H | i-butyl | H | 3 | β | 435.29 | 5.64 |
| 25 | H | p-methyl-phenyl | H | 3 | α | 469.27 | 5.97 |
| 28 | H | o,p-difluoro-phenyl | H | 3 | β | 491.24 | 6.06 |
| 30 | H | 3-methyl-butyl | H | 3 | α | 449.3 | 5.94 |
| 31 | H | i-butyl | H | 3 | α | | |
| 32 | H | p-trifluoromethoxy-phenyl | H | 3 | β | 539.24 | 6.31 |
| 33 | H | phenethyl | H | 4 | β | 497.3 | 6.06 |
| 34 | H | cyclohexyl-methyl | H | 3 | α | 475.32 | 6.22 |
| 36 | Me | i-butyl | H | 3 | β | 449.3 | 6.65 |
| 37 | Me | o-nitro-phenyl | H | 3 | β | 514.26 | 6.65 |
| 38 | H | p-benzaldehyde | H | 3 | α | 483.25 | 5.58 |
| 39 | H | m-methoxy-phenyl | H | 3 | α | 485.27 | 5.78 |
| 40 | H | p-trifluoromethoxy-phenyl | H | 3 | α | 539.24 | 6.35 |
| 41 | Me | trifluoromethoxy | H | 3 | β | 433.27 | 6.26 |
| 42 | H | i-butyl | H | 4 | β | 449.3 | 5.89 |
| 43 | H | m-hydroxy-phenyl | H | 3 | β | 471.25 | 5.22 |
| 44 | H | 6-methoxy-naphthalen-2-yl | H | 3 | α | 535.28 | 6.19 |
| 45 | H | p-trifluoromethyl-phenyl | H | 3 | β | 523.24 | 6.28 |
| 46 | H | o-fluoro-phenyl | H | 3 | α | 473.25 | 5.97 |
| 48 | H | 3-methyl-butyl | H | 4 | β | 463.32 | 6.17 |
| 49 | H | p-trifluoro-phenyl | H | 3 | α | 523.24 | 6.3 |
| 50 | Me | propyl | H | 3 | β | 435.29 | 6.42 |
| 51 | H | m-methoxy-phenyl | H | 3 | β | 485.27 | 5.75 |
| 52 | H | m,m-difluoro-phenyl | H | 3 | α | 491.24 | 6.14 |
| 53 | Me | m-hydroxy-phenyl | H | 4 | β | 499.28 | 6.34 |
| 53 | H | m-hydroxy-phenyl | H | 4 | β | 485.27 | 5.43 |
| 54 | H | cyclohexylmethyl | H | 4 | β | 489.34 | 6.46 |
| 55 | H | 2-hydroxy-ethyl | H | 3 | β | 423.25 | 4.55 |
| 56 | H | o,p-difluoro-phenyl | H | 3 | α | 491.24 | 6.1 |
| 57 | Me | cyclohexyl | H | 3 | β | 475.32 | 6.99 |
| 58 | H | i-butyl | H | 6 | β | 477.34 | 6.36 |
| 59 | Me | thiophen-3-yl | H | 3 | β | 475.23 | 6.53 |

TABLE 3-continued selected examples of compounds of formula Ix

| cpd | R¹ | R² | R⁷ | n | cnfg. C$_{15}$ | MS (m/z) | Rt (min) |
|---|---|---|---|---|---|---|---|
| 60 | Me | p-hydroxymethyl-phenyl | H | 3 | β | 499.28 | 5.88 |
| 62 | H | methoxy-methyl | H | 2 | β | 409.24 | 4.74 |
| 63 | H | 2-hydroxy-ethyl | H | 2 | β | 409.24 | 4.39 |
| 64 | Me | o-fluoro-phenyl | H | 3 | β | 487.26 | 6.91 |
| 65 | H | m-trifluoro-phenyl | H | 3 | α | 523.24 | 6.28 |
| 66 | Me | phenethyl | H | 3 | β | 497.3 | 6.79 |
| 67 | H | m-trifluoromethyl-phenyl | H | 3 | β | 523.24 | 6.25 |
| 68 | Me | p-methoxy-phenyl | H | 3 | β | 499.28 | 6.6 |
| 69 | H | 3-methyl-butyl | H | 6 | β | 491.35 | 6.65 |
| 70 | Me | 3-methyl-butyl | H | 3 | β | 463.32 | 6.92 |
| 71 | Me | methoxy-methyl | H | 3 | β | 437.27 | 5.87 |
| 72 | H | o-trifluoro-phenyl | H | 3 | α | 523.24 | 6.06 |
| 73 | H | m,m-difluoro-phenyl | H | 4 | β | 505.25 | 6.31 |
| 74 | Me | m-methoxy-phenyl | H | 3 | β | 499.28 | 6.66 |
| 75 | Me | p-methyl-phenyl | H | 3 | β | 483.29 | 6.89 |
| 76 | Me | p-dimethylamino-phenyl | H | 3 | β | 512.32 | 6.77 |
| 77 | Me | thiophen-3-yl | H | 4 | β | 489.24 | 6.81 |
| 78 | Me | cyclohexyl-methyl | H | 3 | β | 489.34 | 7.18 |
| 79 | Me | phenethyl | H | 4 | β | 511.32 | 7.04 |
| 80 | Me | m-hydroxy-phenyl | H | 3 | β | 485.27 | 6.05 |
| 82 | Me | dimethylamino-methyl | H | 3 | β | 450.3 | 5.01 |
| 83 | Me | o-chloro-phenyl | H | 3 | β | 503.23 | 7.06 |
| 84 | H | o-trifluoromethyl-phenyl | H | 3 | β | 523.24 | 6.05 |
| 85 | Me | p-hydroxy-naphthalen-2-yl | H | 4 | β | 487.29 | 5.86 |
| 86 | H | 6-methoxy-naphthalen-2-yl | H | 4 | β | 549.3 | 6.38 |
| 87 | Me | m,m-difluoro-phenyl | H | 3 | β | 505.25 | 7 |
| 88 | Me | o,p-difluoro-phenyl | H | 3 | β | 505.25 | 7 |
| 90 | Me | p-methoxy-phenyl | H | 4 | β | 513.3 | 6.89 |
| 91 | Me | o-trifluoromethyl-phenyl | H | 3 | β | 537.26 | 6.99 |
| 92 | H | o,p-difluoro-phenyl | H | 4 | β | 505.25 | 6.29 |
| 93 | H | methoxy-methyl | H | 6 | β | 465.3 | 5.6 |
| 94 | Me | o-methoxy-phenyl | H | 3 | β | 499.28 | 6.78 |
| 95 | H | 2-hydroxy-ethyl | H | 6 | β | 465.3 | 5.15 |
| 96 | Me | hydroxymethyl | H | 3 | β | 423.25 | 5.38 |
| 97 | Me | propyl | H | 4 | β | 449.3 | 6.75 |
| 98 | Me | acetyl | H | 3 | β | 435.25 | 6.1 |
| 99 | Me | cyclohexyl-methyl | H | 4 | β | 503.35 | 7.5 |
| 100 | H | m-hydroxy-phenyl | H | 6 | β | 513.3 | 5.84 |
| 101 | H | hydroxyl-methyl | H | 3 | α | 409.24 | 4.53 |
| 102 | Me | benzo-p-nitrile | H | 3 | β | 494.27 | |
| 103 | H | methoxy-methyl | H | 3 | α | 423.25 | 4.92 |
| 104 | Me | benzylmethyl-amino | H | 3 | β | 526.33 | 6.26 |
| 105 | H | hydroxy-methyl | H | 6 | β | 451.28 | 5.13 |
| 106 | Me | pyridine-2-yl | H | 3 | β | 470.27 | 6.2 |
| 107 | H | methoxy-methyl | H | 3 | β | 423.25 | 4.92 |
| 108 | Me | p-benzaldehyde | H | 4 | β | 513.3 | 6.18 |
| 109 | Me | pyridine-4-yl | H | 3 | β | 470.27 | 5.91 |
| 110 | Me | 1-hydroxy-cyclopentyl | H | 3 | β | 477.3 | 5.91 |
| 111 | Me | cyclopropyl | H | 4 | β | 447.29 | 6.55 |
| 112 | Me | p-methyl-phenyl | H | 4 | β | 497.3 | 7.21 |
| 113 | Me | pyridine-3-yl | H | 3 | β | 470.27 | 5.91 |
| 114 | Me | 2-hydroxyethyl | H | 3 | β | 437.27 | 5.37 |
| 115 | Me | p-dimethylamino-phenyl | H | 4 | β | 526.33 | 7.05 |
| 116 | Me | o-fluoro-phenyl | H | 4 | β | 501.28 | 7.2 |
| 117 | H | o-trifluoromethyl-phenyl | H | 4 | β | 537.26 | 6.29 |
| 118 | H | hydroxy-methyl | H | 3 | β | 409.24 | 4.52 |
| 119 | Me | 6-methoxy-naphthalen-2-yl | H | 3 | β | 549.3 | 7.03 |
| 120 | Me | dioxo-thiomorpholin-4-yl-methyl | H | 4 | β | 554.29 | 5.79 |
| 121 | Me | o-chloro-phenyl | H | 4 | β | 517.25 | 7.36 |
| 122 | Me | hydroxyl-methyl | H | 4 | β | 437.27 | 5.66 |
| 123 | Me | m-methoxy-phenyl | H | 4 | β | 513.3 | 6.96 |
| 124 | Me | p-trifluoromethoxy-phenyl | H | 3 | β | 553.26 | 7.19 |
| 125 | Me | 3-methyl-3H-imidazol-4-yl | H | 3 | β | 473.28 | |
| 126 | Me | o-nitro-phenyl | H | 4 | β | 528.27 | 6.92 |
| 127 | H | o,p-difluoro-phenyl | H | 4 | β | 533.29 | 6.74 |
| 128 | H | phenethyl | H | 4 | β | 525.34 | 6.49 |
| 129 | Me | cyclohexyl | H | 4 | β | 489.34 | 7.3 |
| 130 | H | 2-hydroxy-ethyl | H | 4 | β | 437.27 | 4.73 |
| 131 | Me | p-trifluoromethyl-phenyl | H | 3 | β | 537.26 | 7.14 |
| 132 | Me | p-benzonitrile | H | 4 | β | 508.28 | 6.85 |
| 133 | Me | dioxo-thiomorpholin-4-yl-methyl | H | 3 | β | 540.28 | 5.53 |
| 134 | H | p-methyl-phenyl | H | 6 | β | 511.32 | 6.62 |
| 135 | H | p-methoxy-phenyl | H | 6 | β | 527.31 | 6.32 |
| 136 | Me | pyridine-4-yl | H | 4 | β | 484.28 | 6.24 |
| 137 | H | m-methoxy-phenyl | H | 6 | β | 527.31 | 6.41 |
| 138 | H | 2-hydroxy-ethyl | H | 3 | α | 423.25 | 4.56 |
| 139 | Me | i-butyl | H | 4 | β | 463.32 | 6.94 |
| 140 | H | m-trifluoromethyl-phenyl | H | 4 | β | 537.26 | 6.49 |
| 141 | H | methoxy-methyl | H | 4 | β | 437.27 | 5.14 |
| 142 | Me | methoxy-methyl | H | 4 | β | 451.28 | 6.18 |
| 143 | H | 6-methoxy-naphthalen-2-yl | H | 6 | β | 577.33 | 6.77 |
| 144 | Me | 3-methyl-butyl | H | 4 | β | 477.34 | 7.22 |
| 145 | Me | m,m-difluoro-phenyl | H | 4 | β | 519.27 | 7.25 |
| 146 | Me | o,p-difluoro-phenyl | H | 4 | β | 519.27 | 7.28 |
| 147 | Me | acetyl | H | 4 | β | 449.27 | 6.42 |
| 148 | H | m,m-difluoro-phenyl | H | 4 | β | 533.29 | 6.74 |
| 149 | H | hydroxy-methyl | H | 2 | β | 395.22 | 4.36 |
| 150 | Me | o-methoxy-phenyl | H | 4 | β | 513.3 | 7.08 |
| 151 | H | p-trifluoromethyl-phenyl | H | 4 | β | 537.26 | 6.49 |
| 152 | H | cyclohexylmethyl | H | 6 | β | 517.37 | 6.94 |
| 153 | Me | p-nitro-phenyl | H | 3 | β | 514.26 | 6.78 |
| 154 | Me | pyridine-3-yl | H | 4 | β | 484.28 | 6.22 |
| 155 | Me | o-trifluoromethyl-phenyl | H | 4 | β | 551.28 | 7.25 |
| 156 | Me | m-trifluoromethyl-phenyl | H | 3 | β | 537.26 | 7.14 |
| 157 | H | o-trifluoromethyl-phenyl | H | 6 | β | 565.29 | 6.72 |
| 158 | Me | p-nitro-phenyl | H | 4 | β | 528.27 | 7.05 |
| 159 | Me | p-trifluoromethoxy-phenyl | H | 4 | β | 567.27 | 7.42 |
| 160 | Me | 2-hydroxy-ethyl | H | 4 | β | 451.28 | 5.68 |
| 161 | H | p-trifluoromethoxy-phenyl | H | 4 | β | 581.29 | 6.92 |
| 162 | Me | pyridine-2-yl | H | 4 | β | 484.28 | 6.53 |
| 163 | Me | m-trifluoromethyl-phenyl | H | 4 | β | 551.28 | 7.39 |
| 164 | H | m-trifluoromethyl-phenyl | H | 6 | β | 565.29 | 6.89 |
| 165 | Me | benzenesulfonyl-methyl | H | 4 | β | 577.26 | 5.43 |
| 166 | H | p-trifluoromethyl-phenyl | H | 6 | β | 565.29 | 6.88 |
| 167 | Me | 6-methoxy-naphthalen-2-yl | H | 4 | β | 563.31 | 7.3 |
| 168 | H | o-fluoro-phenyl | H | 6 | β | 515.29 | 6.65 |
| 169 | Me | p-trifluoromethyl-phenyl | H | 4 | β | 551.28 | 7.38 |
| 170 | H | hydroxy-methyl | H | 4 | β | 423.25 | 4.72 |

All compounds according to this invention can be prepared as depicted in more detail above in schemes 1 to 5. It is evident that otherwise substituted or modified compounds as defined by formula (Ix) of the claims can be prepared analogously, e.g. by using substituted or modified analogues of the starting alkyne compound described in schemes 4 or 5. The selected examples presented should not be taken as limiting.

The Synthesis of Estron Derivatives of Formula (Iv):

Intermediates of Compounds of Formula (Iy)

The synthesis of estratrien derivatives with variations at $C_2$ is described in detail in PCT application WO 2006/125800.

Certain estrone alkine intermediates with X and Y=O for the synthesis of formula (Iy) compounds may be prepared via the following route

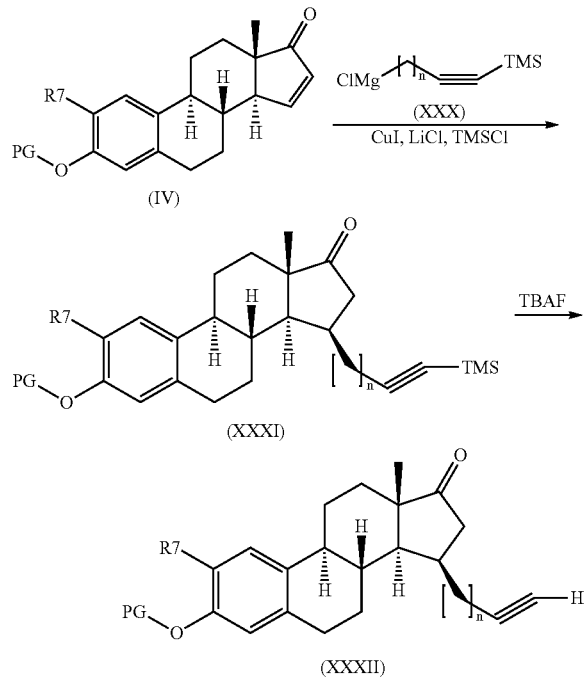

The preparation of the educt (IV) with e.g. $R^1$=benzyl and $R^7$=H is described in detail in PCT application WO 2005/047303.

The freshly prepared Grignard reagent (XXX) is firstly converted into the cuprate for directing the regioselectivity to the C15 at enone (IV). After deprotection by cleaving the TMS group, the respective alkine (XXXII) is obtained.

Detailed Synthesis of a Selected Example of XXXII with $R^7$=H and n=3 According to Scheme 6

5-Trimethylsilylpent-4-ynylmagnesium chloride (XXX)

To a mixture of magnesium (60 mmol) in dry THF (2.5 mL) a small amount of (5-Chloropent-1-ynyl)trimethylsilane and iodide are added. Gradually, more of a solution of (5-Chloropent-1-ynyl)trimethylsilane (60 mmol) in dry THF (17 mL) is added and additional heating is applied to keep the reaction going. After complete addition, the mixture is stirred for 2.5 h at reflux temperature. The obtained greenish solution containing (XXX) is used directly in the next step without further purification.

3-O-Benzyl-15-(5-trimethylsilylpent-4-ynyl)estrone XXXIa

A solution of copper(I)iodide (60 mmol) and lithium chloride (63 mmol) in dry THF (120 mL) is prepared. The mixture was cooled to −78° C. and a solution of the freshly prepared Grignard reagent (XXX) (60 mmol) in dry THF is added such that temperature was kept below −77° C. After complete addition, TMSCl (60 mmol) and a solution of 3-benzyldehydroestrone (17 mmol) in dry THF (85 mL) are added slowly. The reaction mixture is warmed to room temperature and stirred for 18 h. The reaction mixture is then filtered and poured into a sat. aqueous $NH_4Cl$ solution. The mixture is extracted with EtOAc (3×) and the combined organic layers are washed with 1N HCl, 30% aqueous ammonia (3×), and brine. The solution is dried with $Na_2SO_4$ and the solvent is evaporated. After purification by column chromatography ($SiO_2$, heptane/EtOAc gradient 10%→15%) compound (XXXIa) (90%) is obtained as a yellowish syrup.

$^1$H-NMR (CDCl$_3$/δ/ppm): 7.31-7.17, m, 5H, 7.05, d, 1H, 6.64, dd, 1H, 6.60, d, 1H, 4.87, s, 2H, 2.81-2.74, m, 2H, 2.28-2.08, m, 6H, 1.96-1.88, m, 1H, 1.80-1.72, m, 1H, 1.64-1.24, m, 10H, 0.90, s, 3H, 0.00, s, 9H.

3-O-Benzyl-15-(pent-4-ynyl)estrone (XXXIIa)

To a solution of compound (XXXIa) (15 mmol) in THF (46 mL) was added a 1 M solution of tetrabutylammonium fluoride in THF (23 mmol). The reaction mixture was stirred at room temperature and followed by TLC. After 1 h the reaction was complete and quenched with water. The mixture was extracted with MTBE (3×) and the combined organic layers were washed with water and brine and dried with $Na_2SO_4$. Evaporation of the solvent afforded compound (XXXIIa) (99%) as a yellow syrup.

$^1$H-NMR (CDCl$_3$/δ/ppm): 7.45-7.32, m, 5H, 7.20, d, 1H, 6.79, dd, 1H, 6.75, d, 1H, 5.04, s, 2H, 2.93-2.90, m, 2H, 2.44-2.21, m, 6H, 2.12-2.03, m, 1H, 1.97, t, 1H, 1.95-1.90, m, 1H, 1.74-1.45, m, 6H, 1.04, s, 3H.

Certain compounds of formula (Iy) can be prepared from the alkine intermediates via the following route:

scheme 7: preparation route of triazole compunds (Iy-I)

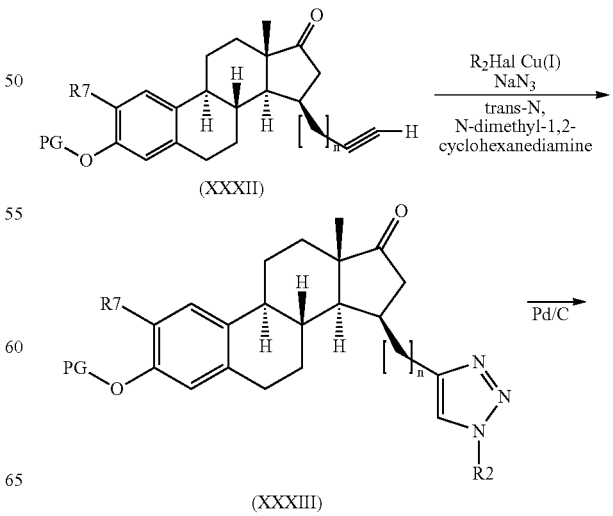

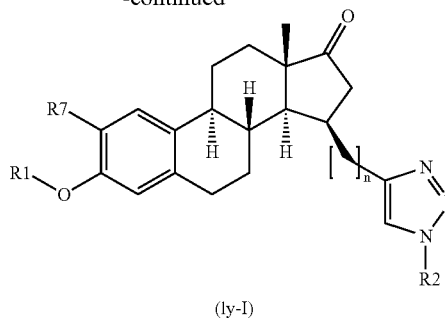

(Iy-I)

The alkine compound (XXXII) is transferred into the corresponding triazole compound (XXXIII) via an in situ generated azide using trans-N,N-dimethyl-1,2-cyclohexanediamine as ligand for Cu(I). After deprotection, the corresponding triazole (Iy-I) is afforded.

Detailed Synthesis of a Selected Example of (Iy-I) with $R^1$, $R^7$=H and n=3 According to Scheme 7

3-O-Benzyl-15-(3-(1-butyl-1H-1,2,3-triazol-4-yl)propyl)estrone (XXXIIa)

A mixture of compound (XXXII) (1.2 mmol), 1-iodobutane (1.2 mmol), sodium azide (2.3 mmol), sodium ascorbate (0.1 mmol), trans-N,N-dimethyl-1,2-cyclohexanediamine (0.2 mmol) and copper(I)iodide (0.1 mmol) in $H_2O$/DMSO 5:1 (3.5 mL) is heated in a microwave for 1.5 h at 100° C. Water is added and the mixture is extracted with EtOAc(3×). The combined org. layers are washed with water and dried with $Na_2SO_4$. Evaporation of the solvent and purification by column chromatography ($SiO_2$, heptane/EtOAc gradient 30%→50%) afford (XXXIIIa) (56%) as a milky syrup.

$^1$H-NMR ($CDCl_3$/δ/ppm): 7.45-7.31, m, 5H, 7.25, s, 1H, 7.19, d, 1H, 6.78, dd, 1H, 6.74, d, 1H, 5.04, s, 2H, 4.32, t, 2H, 2.91-2.87, m, 2H, 2.75-2.73, m, 2H, 2.43-2.32, m, 5H, 2.04-1.95, m, 1H, 1.92-1.63, m, 8H, 1.49-1.26, m, 6H, 1.00, s, 3H, 0.95, t, 3H.

15-[3-(1-butyl-1H-1,2,3-triazol-4-yl)propyl]-3-hydroxyestra-1(10), 2,4-trien-17-one (300)

A mixture of (XXXIIIa) (0.65 mmol) and Pd/C (40 mg) in MeOH (6 mL) and EtOAc (3 mL) is charged with atmospheric $H_2$. The reaction is followed by TLC and after 1 d of low conversion extra catalyst is added. After completion of the reaction the catalyst is filtered off over Celite®, which is washed with MeOH. Evaporation of the solvent affords a grey syrup, which is purified by column chromatography (SiO2, heptane/EtOAc gradient 50%→70%). Evaporation of the solvent yield compound (300) (72%) as an off-white foam.

$^1$H-NMR ($CDCl_3$/δ/ppm): 7.27, s, 1H, 7.11, d, 1H, 6.63, dd, 1H, 6.61, d, J1H, 5.65, broad s, 1H, 4.33, t, 2H, 2.86-2.82, m, 2H, 2.76-2.74, m, 2H, 2.42-2.30, m, 5H, 1.90-1.61, m, 9H, 1.46-1.31, m, 6H, 0.98, s, 3H, 0.95, t, 3H Alternatively, if $R^2$ is e.g. 2,4-difluoro, certain compounds of formula (Iy) can be prepared from the alkine intermediates via the following route (scheme 8):

scheme 8: alternative preparation route of triazoles with $R^2$ = difluorophenyl

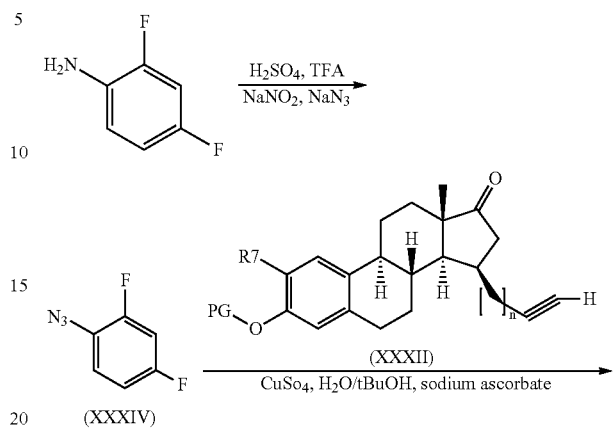

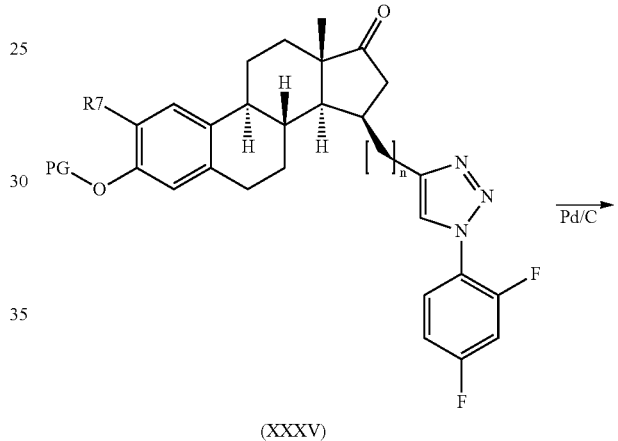

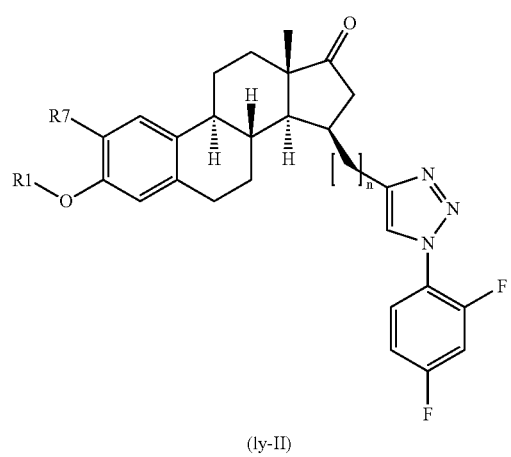

(Iy-II)

Diazotisation of 2,4-difluoroaniline and subsequent substitution with sodium azide lead to azide (XXXIV) (see Suginome et al. (1989), J. Org. Chem, 54(25) 5945). Coupling catalysed by Cu(I) with alkine compound (XXXII) results in protected triazole (XXXV). After deprotection, the corresponding triazole (Iy-II) is afforded.

Detailed Synthesis of a Selected Example of (Iy-II) with $R^1$, $R^7$=H and n=3 According to Scheme 8

2,4-Difluorophenyl azide (XXXIVa)

2,4-Difluoroaniline (99 mmol) is dissolved in a mixture of trifluoroacetic acid (86 mL) and sulfuric acid (17 mL). The mixture is cooled in an icebath and a solution of sodium nitrite (129 mmol) in water (86 mL) was added slowly, while maintaining T<10° C. The mixture is stirred for another 30 min at 0° C. before a solution of sodium azide (11.3 g, 174 mmol) in water (63 mL) is added dropwise [Caution: vigorous evasion of gas]. The temperature is kept below 12° C. during addition. The mixture is stirred at rt overnight and then extracted with MTBE (3×). The combined org. layers are washed with 2.5N aqueous NaOH solution until all traces of trifluoroacetic acid are removed. Washed with water and dried with $Na_2SO_4$. Evaporation of the solvent and purification over a short column ($SiO_2$, pentane) afford (XXXIV) (85%) as a yellow fluid.

$^1$H-NMR ($CDCl_3$/δ/ppm): 7.06-6.98, m, 1H, 6.91-6.83, m, 2H $^{19}$F-NMR ($CDCl_3$/δ/ppm): −114.3, m, 1F; −122.1, m, 1F 3-O-Benzyl-15-(3-(1-(2,4-difluorophenyl)-1H-1,2,3-triazol-4-yl)propyl)estrone (XXXVa)

To (XXXII) (5.0 mmol) and (XXXIV) (5.5 mmol) in tert-butanol (4×10 mL) a solution of sodium ascorbate (1.0 mmol) in water (4×0.5 mL) and a solution of copper(II)sulfate pentahydrate (1 mmol) in water (4×0.5 mL) is added. The batches are then heated in a microwave (Biotage, 30 min at 100° C.) and poured into water. The mixture as extracted with $CH_2Cl_2$ (3×) and washed with water (2×) and brine. Drying with $Na_2SO_4$ and evaporation of the solvent afford a yellow syrup. The purification by column chromatography ($SiO_2$, heptane/EtOAc gradient 20%→35%) yield compound (XXXVa) (82%) as an off-white solid.

$^1$H-NMR ($CDCl_3$/δ/ppm): 7.94-7.92, m, 1H, 7.77, d, 1H, 7.45-7.32, m, 5H, 7.19, d, 1H, 7.10-7.03, m, 2H, 6.79, dd, 1H, 6.73, d, 1H, 5.04, s, 2H, 2.89-2.83, m, 4H, 2.45-2.34, m, 5H, 2.04-1.96, m, 1H, 1.94-1.84, m, 2H, 1.75-1.71, m, 4H, 1.50-1.44, m, 4H, 1.02, s, 3H $^{19}$F-NMR ($CDCl_3$/δ/ppm): −108.3, m, 1F; −119.7, m, 1F 15β-{3-[1-(2,4-difluorophenyl)-1H-1,2,3-triazol-4-yl]propyl}-3-hydroxyestra-1(10), 2,4-trien-17-one (301)

To a mixture of (XXXVa) (0.70 mmol) in EtOH (15 mL) is added a slurry of 10% Pd/C (400 mg) in EtOH (10 mL). The mixture is charged with $H_2$-gas (1 atm) and stirred for 18 h at rt. After according to TLC analysis the reaction is finished and the mixture is filtered over a Celite® pad and washed with MeOH. Evaporation of the solvent and purification by column chromatography afford 301 (79%) as a white foam.

$^1$H-NMR ($CDCl_3$/δ/ppm): 7.97-7.89, m, 1H, 7.78, d, 1H, 7.14-7.02, m, 3H, 6.65, dd, 1H, 6.59, d, 1H, 5.19, s, 1H, 2.87-2.81, m, 4H, 2.45-2.27, m, 5H, 2.00-1.88, m, 3H, 1.77-1.69, m, 4H, 1.52-1.44, m, 4H, 1.01, s, 3H, $^{19}$F-NMR ($CDCl_3$/δ/ppm): −108.2, m, 1F; −119.7, m, 1F Alternatively, if X, Y=F, certain compounds of formula (Iy) can be prepared from the ketone triazoles (XXXIII) via the following route (scheme 9):

scheme 9: preparation route of certain di-fluoro-triazoles-(Iy-III)

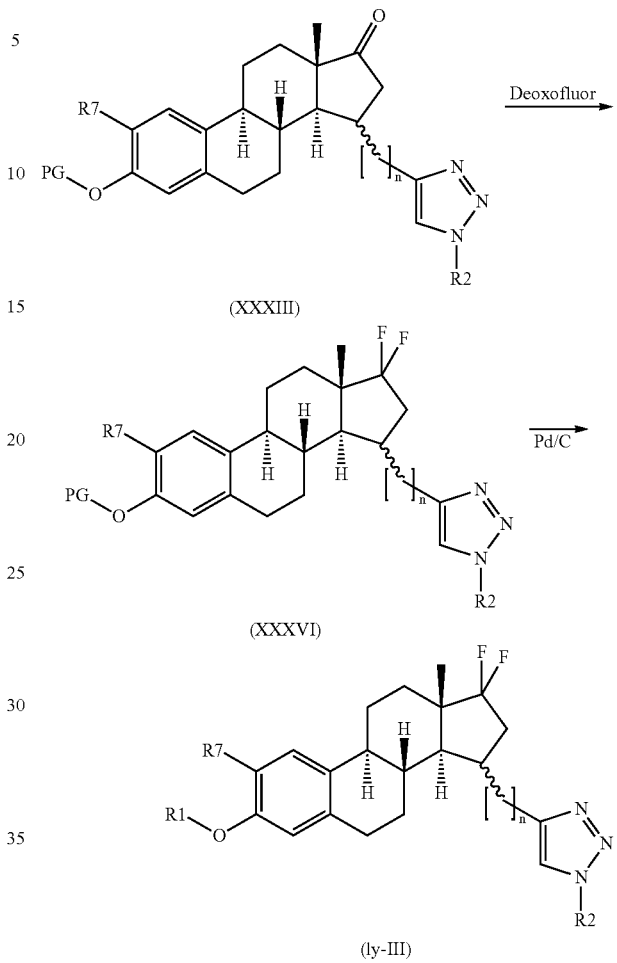

The ketone triazoles (XXXIII) are fluorinated with Deoxofluor. Deprotection of the oxygen by cleaving the protection group afford triazoles (Iy-III).

Detailed Synthesis of a Selected Example of (Iy-III) with $R^1$, $R^7$=H and n=3 According to Scheme 9

3-O-benzyl-15-(3-(1-(2,4-difluorophenyl)-1H-1,2,3-triazol-4-yl)propyl)-17,17-difluoroestrone (XXXVIa)

To a solution of (XXXIII) (12.4 mmol) in $CH_2Cl_2$ (25 mL) at 0° C. a solution of 50% Deoxofluor in toluene (113 mmol) is added. After addition of a few drops of EtOH, the mixture is warmed to rt and stirred for 18 h. Extra $CH_2Cl_2$ is added to maintain a clear solution and a few extra drops of EtOH. The mixture is heated to reflux temperature and stirred for 2.5 days. After TLC show a sufficient conversion, the reaction mixture is carefully poured into a cold saturated $NaHCO_3$ solution (400 mL). The mixture is extracted with $CH_2Cl_2$ (3×130 mL) and the combined organic layers are washed with water and brine. After drying with $Na_2SO_4$ and evaporation of the solvent, a brown solid was obtained (8.0 g), which was purified by column chromatography ($SiO_2$, heptane/$CH_2Cl_2$/EtOAc gradient 5:4:1→44:5:1). The resulting solid (5.6 g) is further purified by reversed phase column chromatography (RediSep column 120 g, H$_2$O/MeCN gradient 25%→100%, flow rate 55 ml/min), which yield (XXXVIa) (12%) as a white crystalline solid.

$^1$H-NMR (CDCl$_3$/δ/ppm): 7.97-7.89, m, 1H, 7.76, d, 1H, 7.45-7.32, m, 5H, 7.19, d, 1H, 7.09-7.02, m, 2H, 6.78, dd, 1H, 6.72, d, 1H, 5.04, s, 2H, 2.84-2.78, m, 4H, 2.44-2.19, m, 5H, 2.17-1.83, m, 2H, 1.79-1.58, m, 6H, 1.54-1.35, m, 3H, 1.02, s, 3H.

$^{19}$F-NMR (CDCl$_3$/δ/ppm): −105.2, m, 1F, −108.3, m, 1F, −116.2, m, 1F, −119.7, m, 1F 15-{3-[1-(2,4-difluorophenyl)-1H-1,2,3-triazol-4-yl]propyl}-17,17-difluoroestra-1(10), 2,4-trien-3-ol (302)

To a mixture of (XXXVIa) (1.44 mmol) in EtOH (10 mL) is added a slurry of 10% Pd/C (450 mg) in EtOH (20 mL). The flask is charged with H$_2$-gas (1 atm) and stirred 18 h at rt. After TLC analysis show a full conversion of starting material, the mixture is filtered over Celite®, which is then washed with MeOH. After evaporation of the solvent a colourless syrup (778 mg) is obtained. Purification by column chromatography (SiO$_2$, heptane/EtOAc gradient 20%→30%) yield (302) (87%) as a white foam.

$^1$H-NMR (CDCl$_3$/δ/ppm): 7.96-7.88, m, 1H, 7.78, d, 1H, 7.13-7.02, m, 3H, 6.65, dd, 1H, 6.59, d, 1H, 5.68, broad s, 1H, 2.84-2.75, m, 4H, 2.50-2.37, m, 1H, 2.34-2.16, m, 3H, 2.06-1.87, m, 2H, 1.84-1.49, m, 7H, 1.46-1.26, m, 3H, 0.99, s, 3H $^{19}$F-NMR (CDCl$_3$/δ/ppm): −105.2, m, 1F, −108.1, m, 1F, −116.2, m, 1F, −119.6, m, 1F Biological Testing Materials and Methods
Screening Strategy Screening is carried out in five major steps:
Recombinant HPLC assay 17βHSD1 and 17βHSD2
17βHSD1-MCF-7 cell assay
Estrogen receptor binding and functional assay
In vivo assays, e.g. UWT assay, tumor model, and
Disease-oriented models, thereby first focusing on the effect on enzymatic activity of recombinant human 17βHSD1 and on selectivity towards recombinant human 17β-hydroxysteroid dehydrogenase type 2 (17βHSD2), the enzyme catalysing the reverse reaction as 17βHSD1 by conversion of E2 to E1 (methods as described in WO2005032527). These protein-based tests are followed by the corresponding cell-based assays (WO2005032527). Another important factor is selectivity towards the estrogen receptor that is studied in a commercially available binding assay (PanVera LCC, Madison, Wis.) as well as in a functional ERE-LUC receptor gene assay as described by M. E. Burow, S. M. Boue, B. M. Collins-Burow, L. I. Melnik, B. N. Duong, C. H. Carter-Wientjes, S. Li, T. E. Wiese, T. E. Cleveland and J. A. McLachlan, Phytochemical glyceollins, isolated from soy, mediate antihormonal effects through estrogen receptor alpha and beta, *J. Clin. Endocrinol. Metab.* 86 (2001) (4), pp. 1750-1758. After determining metabolic and physicochemical stability of a compound the first set of in vivo experiments is started. Lack of estrogenic activity in vivo is proven using the classical uterine growth test in immature rats (H. D. Lauson, C. G. Heller, J. B. Golden and E. L. Severinghaus, The immature rat uterus in the assay of estrogenic substances, a comparison of estradiol, estrone and estriol, *Endocrinoloy* 24 (1939), pp. 35-44). Efficacy of 17βHSD1-inhibition is demonstrated by reduction of 17βHSD1-dependent growth of tumor xenografts in immunodeficient mice as described by Husen, B., Huhtinen, K., Poutanen, M., Kangas, L., Messinger, J., Thole, H. (2006) Evaluation of inhibitors for 17β-hydroxysteroid dehydrogenase type 1 in vivo in immunodeficient mice inoculated with MCF-7 cells stably expressing the recombinant human enzyme. Mol Cell Endocrinol. 2006 Mar. 27; 248(1-2):109-13. Epub 2006 Jan. 10. Finally disease-oriented models as disclosed by R. Grümmer, F. Schwarzer, K. Bainczyk, H. Hess-Stumpp, P. A. Regidor, A. E. Schindler and E. Winterhager, Peritoneal endometriosis: validation of an in vivo model, *Hum. Reprod.* 16 (2001) (8), pp. 1736-1743 and A. Einspanier, A. C. K Brüns, B. Husen and C. Simon, Induction of endometriosis in the marmoset monkey (*Callithrix jacchus*) Mol Hum Reprod. 2006 May; 12(5):291-9. Epub 2006 Apr. 11 determine the proof of concept of these compounds.

Some of the above-mentioned as well as alternative assays are described in more detail below:

Inhibition of the 17β-Hydroxysteroid Dehydrogenase Type 1 Enzyme

17β-HSD1 purification: Recombinant baculovirus was generated by the "Bac to Bac Expression System" (Invitrogen). Recombinant bacmid was transfected to Sf9 insect cells using "Cellfectin Reagent" (Invitrogen). 60 h later cells were harvested; the microsomal fraction was isolated as described by Puranen et al. (1994). Aliquots were stored frozen until determination of enzymatic activity.

Assay—Inhibition of recombinant human 17β-HSD1: Recombinant protein (0.1 μg/ml) was incubated in 20 mM KH$_2$PO$_4$ pH 7.4 with 30 nM 3H-estrone and 1 mM NADPH for 30 min at RT, in the presence of potential inhibitors at concentrations of 1 μM or 0.1 μM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min of acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(cpm \text{ estradiol in sample with inhibitor})/[(cpm \text{ estrone in sample with inhibitor}) + (cpm \text{ estradiol in sample with inhibitor})]\}}{\{(cpm \text{ estradiol in sample without inhibitor})/[(cpm \text{ estrone in sample without inhibitor}) + (cpm \text{ estradiol in sample without inhibitor})]\}}.$$

Percent inhibition was calculated as follows: % inhibition=100−% conversion

The values "% inhibition" were determined for exemplified compounds, and the results are summarized in table 4 (for 17β-HSD1).

TABLE 4

HSD 1 inhibition values in % of selected compounds of formula I

| compound | chemical structure | inhibition of rec. 17 β-HSD1 | |
|---|---|---|---|
| | | 100 nM | 1 μM |
| 1 | | 92 | 98 |
| 2 | | 88 | 97 |
| 3 | | 86 | 96 |
| 4 | | 92 | 96 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 5 | | 87 | 95 |
| 6 | | 92 | 94 |
| 7 | | 81 | 94 |
| 8 | | 81 | 93 |

TABLE 4-continued
HSD 1 inhibition values in % of selected compounds of formula I
| compound | chemical structure | inhibition of rec. 17 β-HSD1 | |
| --- | --- | --- | --- |
| | | 100 nM | 1 μM |
| 9 | 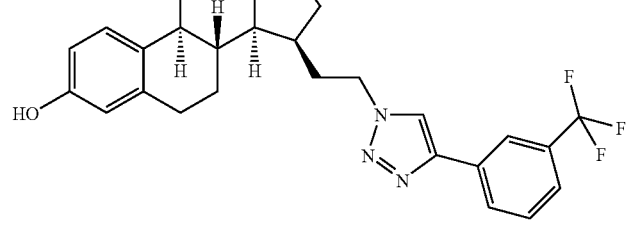 | 84 | 93 |
| 10 | 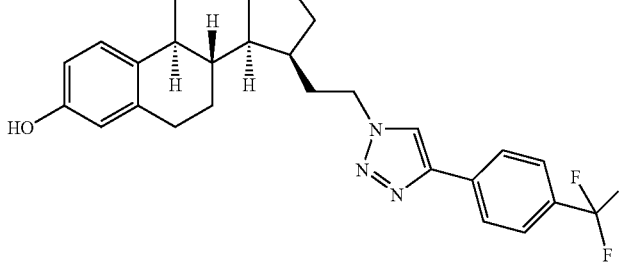 | 83 | 93 |
| 11 | 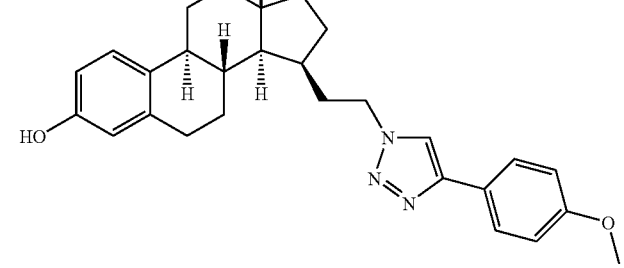 | 75 | 93 |
| 12 | 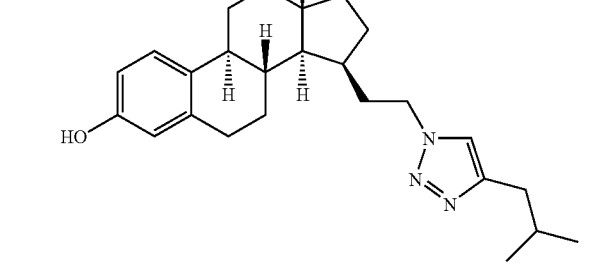 | 86 | 92 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 13 | 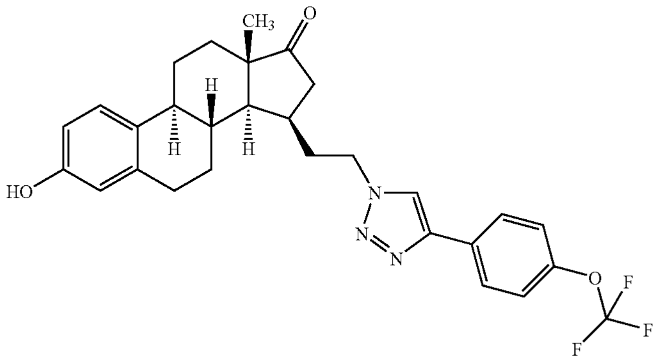 | 83 | 92 |
| 16 | 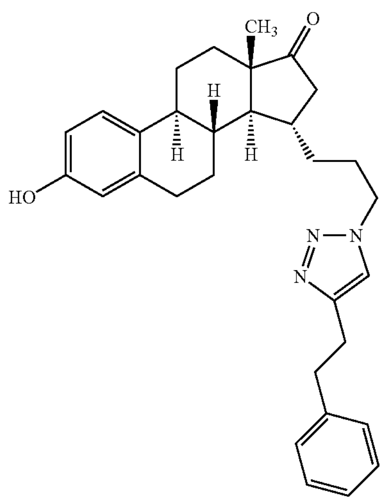 | 38 | 89 |
| 17 | 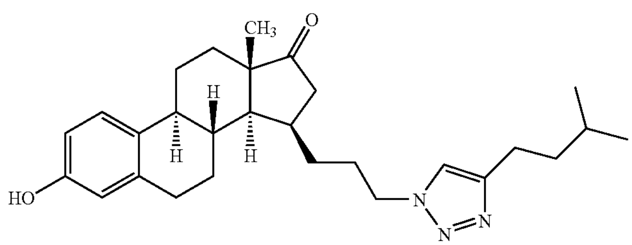 | 61 | 88 |
| 18 | 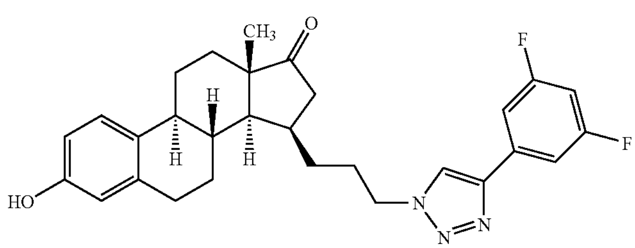 | 64 | 88 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 19 | | 71 | 87 |
| 20 | | 51 | 87 |
| 21 | | 50 | 86 |
| 22 | | 48 | 86 |

TABLE 4-continued

HSD 1 inhibition values in % of selected compounds of formula I

| compound | chemical structure | inhibition of rec. 17 β-HSD1 | |
| --- | --- | --- | --- |
| | | 100 nM | 1 μM |
| 24 | | 52 | 85 |
| 25 | | 49 | 85 |
| 28 | | 40 | 83 |
| 30 | | 25 | 82 |

TABLE 4-continued
HSD 1 inhibition values in % of selected compounds of formula I
| compound | chemical structure | inhibition of rec. 17 β-HSD1 | |
|---|---|---|---|
| | | 100 nM | 1 μM |
| 31 | 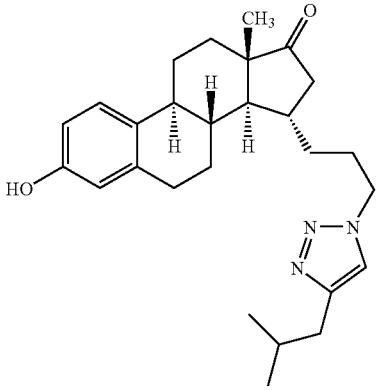 | 32 | 82 |
| 32 | 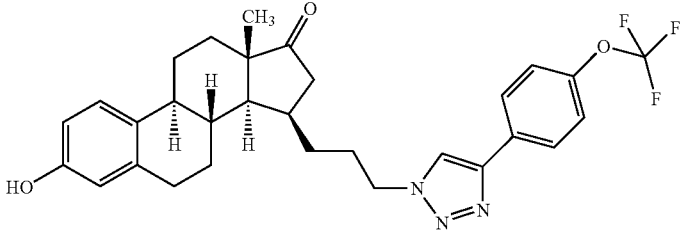 | 67 | 81 |
| 33 | 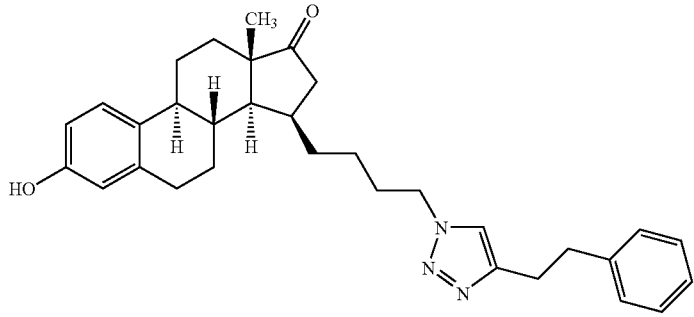 | 20 | 80 |
| 37 | 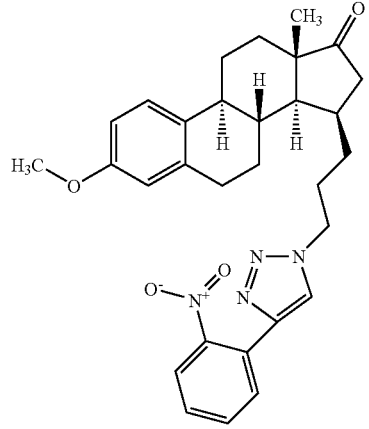 | 25 | 80 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 41 | | 23 | 77 |
| 48 | | 21 | 73 |
| 58 | | 20 | 70 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 59 | | 18 | 69 |
| 60 | | 19 | 69 |
| 69 | | 30 | 64 |

TABLE 4-continued

HSD 1 inhibition values in % of selected compounds of formula I

| compound | chemical structure | inhibition of rec. 17 β-HSD1 | |
| --- | --- | --- | --- |
| | | 100 nM | 1 μM |
| 89 | | 11 | 52 |
| 100 | | 7 | 48 |
| 111 | | 4 | 43 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 112 | 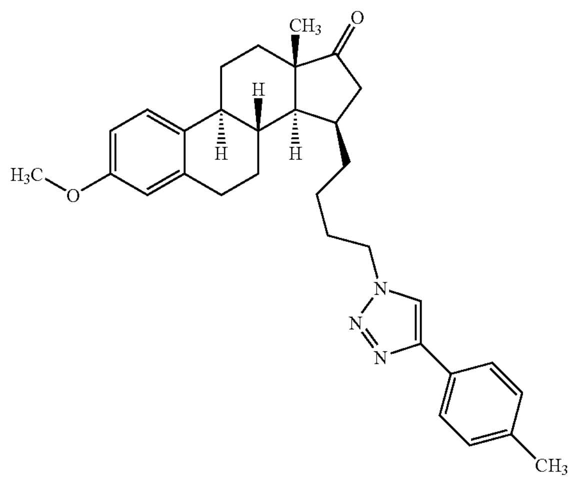 | 12 | 43 |
| 122 | 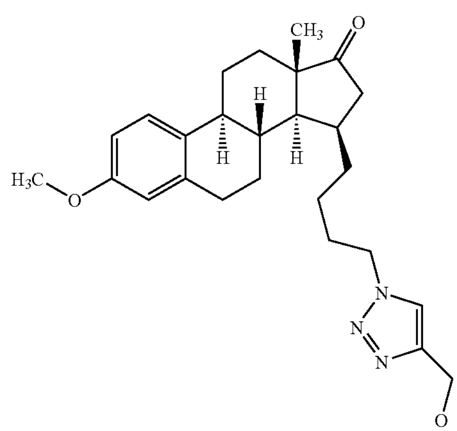 | 5 | 38 |
| 300 | 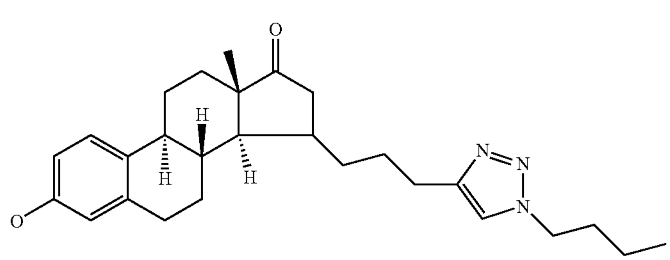 | 85 | 88 |

TABLE 4-continued

HSD 1 inhibition values in % of selected compounds of formula I

| compound | chemical structure | inhibition of rec. 17 β-HSD1 | |
|---|---|---|---|
| | | 100 nM | 1 μM |
| 301 | | 82 | 88 |
| 302 | | 88 | 96 |

Inhibition of the 17β-Hydroxysteroid Dehydrogenase Type 3 Enzyme

The compounds were screened in respect of 17β-HSD3 enzyme activity in vitro on established MCF-7 cell lines, each stably expressing the 17β-HSD3 enzyme. The interconversion of substrate by 17β-HSD3 and the 17β-HSD3 inhibiting activity of chemical compounds in these cell lines were detected by HPLC system. Varying amounts of the test compounds were incubated in the growth medium of the 17β-HSD3 expressing cells together tritium labeled androstenedione (2 nM). The medium samples were removed after exact incubation time and the reaction is stopped by trichloroacetic acid (TCA). The samples were analyzed by HPLC-coupled flow scintillation analysis.

Conversion: The 17β-HSD3 inhibiting activity of an individual test compound was calculated by comparing the conversion of a control sample without any test compound (referred to as "Negative Control") to the (reduced) conversion of the test sample containing the particular compound to be tested (referred to as "Test Sample").

$$\% \text{ inhibition} = 100 \times \frac{\text{Conversion in Negative Control} - \text{Conversion in Test Sample}}{\text{Conversion Negative Control}}$$

The obtained results are shown in Table 3 below. Two concentrations of each compound were used. The number of the compound refers to the numbers indicated in the Experimental Section.

The values "% inhibition" were determined for exemplified compounds, and the results are summarized in table 5 (HSD 3).

TABLE 5

17β-HSD3 inhibition values in % of selected compounds of formula I

| Compound No. | inhibition of 17β-HSD3 | |
|---|---|---|
| | 1 μM | 10 μM |
| 4 | 5 | 40 |
| 6 | 16 | 50 |
| 7 | 12 | 36 |
| 8 | 6 | 61 |
| 12 | — | 37 |
| 17 | 3 | 50 |
| 19 | 11 | 52 |
| 22 | 82 | — |
| 24 | 24 | 64 |
| 300 | 29 | 61 |
| 301 | 24 | 57 |
| 302 | 13 | 70 |

Estrogen Receptor Binding Assay

The binding affinity of the compounds of the invention to the estrogen receptor α and to the estrogen receptor β may be determined according to the in vitro ER binding assays described by Koffmann B et al. (1991) "Evidence for involvement of tyrosine in estradiol binding by rat uterus estrogen receptor." J. Steroid. Biochem. Mol. Biol. 38(2):135. Alternatively, an estrogen receptor binding assay may be performed according to international patent application PCT/US/17799 (published as WO 00/07996 (and related U.S. Pat. No. 6,291,505)).

Estrogen Receptor Transactivation Assays

Compounds of the invention showing binding affinity towards the estrogen receptor may be further tested with regard to their individual estrogenic or anti-estrogenic potential (agonistic binding or antagonistic binding to the ERα or ERβ). The determination of the estrogen receptor agonist activity may be performed according to an in vitro assay system using the MMTV-ERE-LUC reporter system which is for example described within U.S. patent application Ser. No. 10/289,079 (published as US 2003/0170292):

To assay estrogen receptor agonist activity, Hela cells are grown in 24-well microtiter plates and then transiently co-transfected with two plasmids using lipofectamine. The first plasmid comprises DNA encoding human estrogen receptor (either ER-alpha or ER-beta), and the second plasmid comprises an estrogen-driven reporter system comprising: a luciferase reporter gene (LUC) whose transcription is under the control of upstream regulatory elements comprising 4 copies of the vitellogenin estrogen response element (ERE) cloned into the mouse mammary tumor virus (MMTV) promoter (the full name for the reporter system being "MMTV-ERE-LUC"). Cells are exposed to the compounds of the invention in RPMI 1640 medium, supplemented with 10% charcoal-treated fetal calf serum, 2 mM L-glutamine, 0.1 mM non-essential amino acids and 1 mM so-diumpyruvate for 42-48 hours at 37° C. in a 5% carbon dioxide incubator. Concurrently, cells exposed to estradiol (1 nM) serve as positive controls. Replicate wells exposed to the solvent in which the compounds of the invention are dissolved (i.e. ethanol or methanol) are used as negative controls. After the 42-48 hr incubation period, cells are rinsed with phosphate buffered saline (PBS), lysis buffer (Promega Corp) is added, and cell lysates are collected for measurement of luciferase activity with a luminometer. Estrogenic activity of the compounds of the invention is ex-pressed as fold-increase in luciferase activity as compared to that observed in negative control cells.

Alternatively, the determination of the estrogen receptor transactivation activity (estrogenicity assay or agonist assay) and of the inhibitory potency of transactivation activity (anti-estrogenicity assay or antagonist assay) may be performed according to international patent application WO 00/07996 (and related U.S. Pat. No. 6,291,505).

Conclusion

The compounds of the invention show good inhibitory potential of the 17β-HSD1, 17β-HSD2 and/or of the 17β-HSD3 enzyme. As explained in more detail above, the compounds of the invention are therefore regarded as being suited for the treatment of several estrogen and androgen dependent diseases and disorders, respectively. In particular, since several malign and benign pathologies such as e.g. breast cancer, endometriosis and uterine leiomyomas are all 17β-estradiol dependent, a reduction of the endogenous 17β-estradiol concentration in the respective tissue will result in an impaired or reduced proliferation of the 17β-estradiol dependent cells in said tissues as can be demonstrated by the above described in vivo assays. Therefore, the selective inhibitors of the 17β-HSD1 enzyme as described herein are well suited to impair also endogenous productions of estrogens, in particular of 17β-estradiol, in myomas, endometriotic, adenomyotic and endometrial tissue. The application of a compound acting as selective inhibitor on the 17β-HSD1 enzyme, which preferentially catalyzes the reductive reaction, will result in a lowered intracellular estradiol-concentration, since the reductive conversion of the estrone into the active estradiol is reduced or suppressed, and will therefore impair or even reduce the proliferation of the 17β-estradiol dependent cells in the malignant or benign tissue.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A compound corresponding to formula (I)

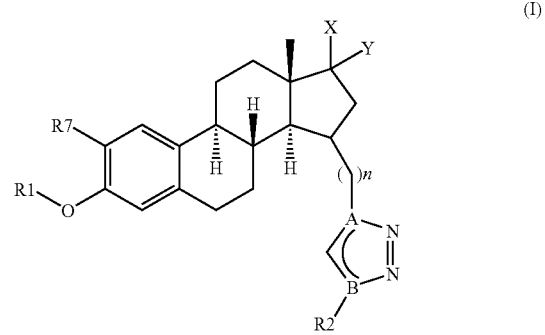

wherein
A represents N and B represents C, or A represents C and B represents N
n represents 1, 2, 3, 4, 5 or 6
X, Y individually represent F, or X and Y together represent =O
$R^1$ is selected from the group consisting of:
  (a) —H,
  (b) —$(C_1$-$C_6)$alkyl,
    which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$OR^3$, —$SR^3$ and —$COOR^3$ moieties,
    or which is optionally substituted by aryl, in which the aryl moiety is optionally substituted by 1 or 2 substituents independently selected from the group consisting of halogen, hydroxyl and —$(C_1$-$C_6)$ alkyl, and
  (c) -phenyl, which is optionally substituted by halogen, carbonitril, —$OR^3$, —$SR^3$, —$COOR^3$, or —$(C_1$-$C_6)$ alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —$(C_1$-$C_6)$alkyl moieties,
    wherein each $R^3$ is independently selected from the group consisting of —H, —$(C_1$-$C_6)$alkyl, optionally substituted by 1, 2 or 3 halogens and/or optionally substituted by 1, 2 or 3 hydroxyl moieties; and aryl, optionally substituted by 1, 2 or 3 halogens,
$R^2$ is selected from the group consisting of:
  (a) —$(C_1$-$C_8)$alkyl, which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
  (b) aryl or aryl-$(C_1$-$C_8)$alkyl, in which the aryl moiety is monocyclic or bicyclic; and which aryl moiety is optionally substituted by halogen, carbonitril, nitro, —OR⁴, —R⁶, —O—SO₂—R⁴, —NR⁴R⁵, —COOR⁴, or —COR⁴; the number of said substituents being 1, 2, 3 or 4 for halogen, and 1 or 2 for any combination of said halogen, carbonitril, nitro, —OR⁴, —R⁶, —O—SO₂—R⁴, —NR⁴R⁵, —COOR⁴ and —COR⁴ moieties; and in which the alkyl moiety is optionally substituted by 1, 2 or 3 halogens;

(c) heteroaryl or heteroaryl-($C_1$-$C_8$)alkyl, in which the heteroaryl moiety contains one, two or three heteroatoms independently selected from the group consisting of N, O or S, the number of N atoms being 0, 1, 2 or 3, and the number of O and S atoms each being 0, 1 or 2, and which heteroaryl moiety is optionally substituted by halogen, carbonitril, nitro, —OR⁴, —R⁶, —O—SO₂—R⁴, —NR⁴R⁵, —COOR⁴ or —COR⁴, the number of said substituents being 1, 2, 3 or 4 for halogen, and 1 or 2 for any combination of said halogen, carbonitril, nitro, —OR⁴, —R⁶, —O—SO₂—R⁴, —NR⁴R⁵, —COOR⁴ and —COR⁴ moieties, and in which the alkyl moiety is optionally substituted by 1, 2 or 3 halogens;

(d) ($C_3$-$C_8$)cycloalkyl or ($C_3$-$C_8$)cycloalkyl-($C_1$-$C_8$)alkyl, in which the cycloalkyl moiety is optionally substituted by halogen, carbonitril, —OR⁴, —R⁶, —O—SO₂—R⁴, —NR⁴R⁵, or —COR⁴; the number of said substituents being 1, 2 or 3 for halogen, and 1 or 2 for any combination of said halogen, carbonitril, —OR⁴, —R⁶, —O—SO₂—R⁴, —NR⁴R⁵ and —COR⁴ moieties, (e) cycloheteroalkyl or cycloheteroalkyl-($C_1$-$C_8$)alkyl, in which the cycloheteroalkyl moiety is optionally substituted by halogen, carbonitril, —OR⁴, —R⁶, —O—SO₂—R⁴, —NR⁴R⁵, or —COR⁴; the number of said substituents being 1, 2 or 3 for halogen, and 1 or 2 for any combination of said halogen, carbonitril, —OR⁴, —R⁶, —O—SO₂—R⁴, —NR⁴R⁵ and —COR⁴ moieties; and (f) —($C_1$-$C_8$)alkanoyl wherein each R⁴ and R⁵ is independently selected from the group consisting of H, —($C_1$-$C_6$)alkyl, optionally substituted by 1, 2 or 3 halogens and/or optionally substituted by 1, 2 or 3 hydroxyl moieties; and aryl and aryl-($C_1$-$C_6$)alkyl, optionally substituted in the aryl moiety by 1, 2 or 3 halogens, or R⁴ and R⁵ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and R⁶ represents —($C_1$-$C_6$)alkyl, which is optionally substituted by 1, 2 or 3 halogens and/or optionally substituted by 1, 2 or 3 hydroxyl moieties;

R⁷ is selected from the group consisting of
(a) H,
(b) ($C_1$-$C_4$)alkyl,
(c) ($C_1$-$C_4$)alkoxy, and
(d) ($C_1$-$C_4$)alkoxy-($C_1$-$C_4$)alkyl moiety, or a stereoisomer, physiologically compatible salt, or prodrug thereof.

2. A compound corresponding to formula (I) according to claim 1, wherein A represents N and B represents C and said compound corresponds to formula (Ix)

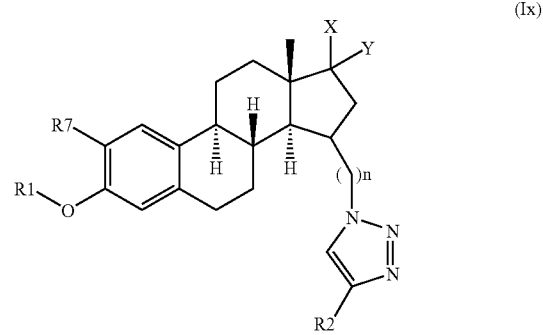

(Ix)

or a physiologically compatible salt or prodrug thereof.

3. A compound corresponding to formula (I) according to claim 1, wherein A represents C and B represents N and said compound corresponds to formula (Iy)

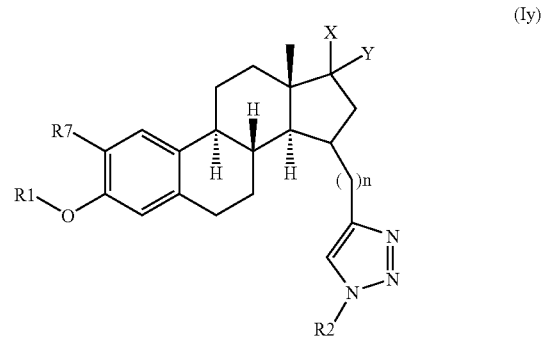

(Iy)

or a physiologically compatible salt or prodrug thereof.

4. A compound according to claim 1, wherein n represents 2, 3, 4, 5 or 6.

5. A compound according to claim 1, wherein X and Y individually represent F.

6. A compound according to claim 1, wherein X and Y together represent =O.

7. A compound according to claim 1, wherein R¹ is selected from the group consisting of —H, —($C_1$-$C_6$)alkyl, -phenyl or —($C_1$-$C_4$)alkyl-phenyl.

8. A compound according to claim 7, wherein R¹ is selected from the group consisting of —H, -methyl or -benzyl.

9. A compound according claim 1 wherein R⁷ is —H.

10. A compound corresponding to formula (I) according to claim 1, in the form of an optically pure enantiomer corresponding to formula (Ia)

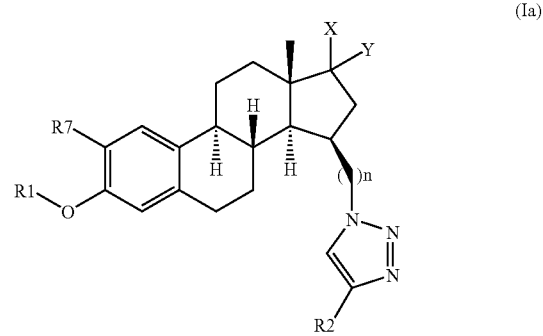

(Ia)

or a physiologically compatible salt or prodrug thereof.

11. A compound corresponding to formula (I) according to claim 1, in the form of an optically pure enantiomer corresponding to formula (Ib)

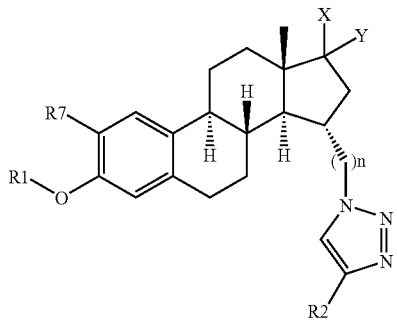

(Ib)

or a physiologically compatible salt or prodrug thereof.

12. A compound corresponding to formula (I) according to claim 1, in the form of an optically pure enantiomer corresponding to formula (Ic)

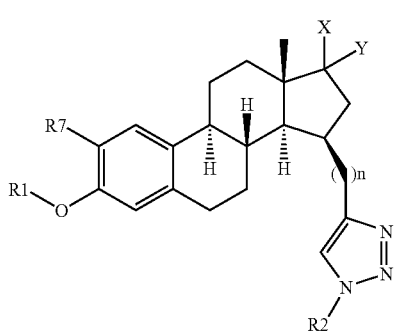

(Ic)

or a physiologically compatible salt or prodrug thereof.

13. A compound corresponding to formula (I) according to claim 1, in the form of an optically pure enantiomer corresponding to formula (Id)

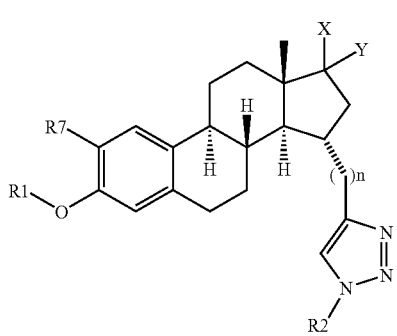

(Id)

or a physiologically compatible salt or prodrug thereof.

14. A compound according to claim 1, wherein $R^2$ is selected from the group consisting of:

(a) —$(C_1$-$C_7)$alkyl, which is optionally substituted by halogen, —$OR^4$, —O—$SO_2$—$R^4$, —$NR^4R^5$, or —$COR^4$; the number of said substituents being 1, 2 or 3 for halogen, and 1 or 2 for any combination of said halogen, —$OR^4$, —$NR^4R^5$, —O—$SO_2$—$R^4$ and —$COR^4$ moieties;

(b) aryl or aryl-$(C_1$-$C_4)$alkyl, in which the aryl moiety is monocyclic or bicyclic;
and which aryl moiety is optionally substituted by halogen, carbonitril, nitro, —$OR^4$, —$R^6$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —$NR^4R^5$, —$COOR^4$ and —$COR^4$ moieties; and in which the alkyl moiety is optionally substituted by 1, 2 or 3 halogens;

(c) heteroaryl or heteroaryl-$(C_1$-$C_4)$alkyl, in which the heteroaryl moiety contains one, two or three heteroatoms independently selected from the group consisting of N, O or S, the number of N atoms being 0, 1, 2 or 3, and the number of O and S atoms each being 0, 1 or 2, and which heteroaryl moiety is optionally substituted by halogen, nitro, —$OR^4$, —$R^6$, —$NR^4R^5$, —$COOR^4$ or —$COR^4$, the number of said substituents being 1, 2, 3 or 4 for halogen, and 1 or 2 for any combination of said halogen, nitro, —$OR^4$, —$R^6$, —$NR^4R^5$, —$COOR^4$ and —$COR^4$ moieties, and in which the alkyl moiety is optionally substituted by 1, 2 or 3 halogens;

(d) $(C_3$-$C_7)$cycloalkyl or $(C_3$-$C_7)$cycloalkyl-$(C_1$-$C_4)$alkyl, in which the cycloalkyl moiety is optionally substituted by halogen, —$OR^4$, —$R^6$, —$NR^4R^5$, or —$COR^4$; the number of said substituents being 1, 2 or 3 for halogen, and 1 or 2 for any combination of said halogen, —$OR^4$, —$R^6$, —$NR^4R^5$ and —$COR^4$ moieties, (e) cycloheteroalkyl or cycloheteroalkyl-$(C_1$-$C_4)$alkyl, in which the cycloheteroalkyl moiety is optionally substituted by halogen, —$OR^4$, or —$R^6$; the number of said substituents being 1, 2 or 3 for halogen, and 1 or 2 for any combination of said halogen, —$OR^4$ and —$R^6$ moieties; and (f) —$(C_1$-$C_4)$alkanoyl
wherein
each $R^4$ and $R^5$ is independently selected from the group consisting of —H, —$(C_1$-$C_4)$alkyl, optionally substituted by 1, 2 or 3 halogens and/or optionally substituted by 1, 2 or 3 hydroxyl moieties; and aryl and aryl-$(C_1$-$C_4)$alkyl, optionally substituted in the aryl moiety by 1, 2 or 3 halogens, or $R^4$ and $R^5$ form together with the nitrogen atom, to which they are attached, a cyclic 6-membered ring system, which is saturated or contains one or more double bonds between the ring atoms, and which ring optionally contains a sulfoxide moiety in addition to the nitrogen atom, and $R^6$ represents —$(C_1$-$C_4)$alkyl, which is optionally substituted by 1, 2 or 3 halogens, and/or optionally substituted by 1, 2 or 3 hydroxyl moieties.

15. A compound according to claim 14, wherein $R^2$ is selected from the group consisting of:

(a) —$(C_1$-$C_6)$alkyl, which is optionally substituted by —$OR^4$, —O—$SO_2$—$R^4$, —$NR^4R^5$; the number of said substituents being 1 or 2 for any combination of said —$OR^4$, —O—$SO_2$—$R^4$ and —$NR^4R^5$ moieties;

(b) aryl or aryl-$(C_1$-$C_2)$alkyl, in which the aryl moiety is phenyl, benzyl or naphthyl; and which aryl moiety is optionally substituted by halogen, carbonitril, nitro, —$OR^4$, —$R^6$, —$NR^4R^5$, or —$COOR^4$; the number of said substituents being 1, 2, 3 or 4 for halogen, and 1 or 2 for any combination of said halogen, carbonitril, nitro, —$OR^4$, —$R^6$, —$NR^4R^5$ and —$COR^4$ moieties;

(c) heteroaryl or heteroaryl-$(C_1$-$C_2)$alkyl, in which the heteroaryl moiety contains one, two or three heteroatoms independently selected from the group consisting of N, O or S, the number of N atoms being 0, 1 or 2, and the number of O and S atoms each being 0 or 1, and which is optionally substituted by —$R^6$ (d) $(C_3$-$C_6)$cycloalkyl or $(C_3$-$C_6)$cycloalkyl-$(C_1$-$C_2)$alkyl, in which the cycloalkyl moiety is optionally substituted by halogen, —$OR^4$ and —$R^6$; the number of said substituents being 1, 2 or 3 for halogen, and 1 or 2 for any combination of said halogen, —$OR^4$, or —$R^6$ moieties, (e) cycloheteroalkyl or cycloheteroalkyl-$(C_1$-$C_2)$alkyl, in which the cycloalkyl moiety is selected from the group consisting of piperidinyl, morpholinyl, thiomorpholinyl, piperazyl, pyryl, pyrrolidinyl, tetrahydrofuryl, azepanyl and tetrahydrothienyl, and which cycloheteroalkyl moiety is optionally substituted by —$OR^4$ or —$R^6$; and (f) —$(C_1$-$C_4)$alkanoyl wherein each $R^4$ and $R^5$ is independently selected from the group consisting of —H, —$(C_1$-$C_4)$alkyl, optionally substituted by 1, 2 or 3 halogens and/or optionally substituted by hydroxyl; and phenyl or phenyl-$(C_1$-$C_2)$ alkyl, or $R^4$ and $R^5$ form together with the nitrogen atom, to which they are attached, a cyclic 6-membered ring system, which is saturated or contains one or more double bonds between the ring atoms, and which ring optionally contains a sulfoxide moiety in addition to the nitrogen atom, and $R^6$ represents —$(C_1$-$C_4)$alkyl, which is optionally substituted by 1, 2 or 3 halogens and/or optionally substituted by hydroxyl.

16. A compound according to claim 14, wherein $R^2$ is selected from the group consisting of:

(a) —$(C_1$-$C_5)$alkyl, which is optionally substituted by benzenesulfonyloxy, benzyl-methyl-amino, cyclohexyl, dimethylamino, dioxothiomorpholin-4-yl, formyl, hydroxyl, methoxy, or phenyl, (b) phenyl or naphthyl, which are optionally substituted by carbonitril, dimethylamino, formyl, hydroxyl, hydroxymethyl, methoxy, methoxycarbonyl, methyl, nitro, trihalomethoxy, trihalomethyl, or 1 or 2 halogens, (c) pyridine-2-yl, pyridine-3-yl, pyridine-4-yl, fur-2-yl, fur-3-yl, thiophen-2-yl, thiophen-3-yl, or imidazol-4-yl, and which are optionally substituted by methyl, (d) cyclopropyl, cyclopentyl, or cyclohexyl, and which are optionally substituted by hydroxyl, and (e) acetyl;

wherein each halogen is independently selected from the group consisting of F, Cl or Br.

17. A compound according to claim 1, wherein said compound is selected from the group consisting of 3-Hydroxy-15β-[2-(4-phenethyl-[1,2,3]triazol-1-yl)-ethyl]-estra-1,3,5(10)-trien-17-one;

3-Hydroxy-15β-{2-[4-(3-hydroxy-phenyl)-[1,2,3]triazol-1-yl]-ethyl}-estra-1,3,5(10)-trien-17-one;

3-Hydroxy-15β-{2-[4-(2,4-difluoro-phenyl)-[1,2,3]triazol-1-yl]-ethyl}-estra-1,3,5(10)-trien-17-one;

3-Hydroxy-15β-{2-[4-(3-methyl-butyl)-[1,2,3]triazol-1-yl]-ethyl}-estra-1,3,5(10)-trien-17-one;

3-Hydroxy-15β-{2-[4-(3,5-difluoro-phenyl)-[1,2,3]triazol-1-yl]-ethyl}-estra-1,3,5(10)-trien-17-one;

3-Hydroxy-15β-[2-(4-cyclohexylmethyl-[1,2,3]triazol-1-yl)-ethyl]-estra-1,3,5(10)-trien-17-one;

3-Hydroxy-15β-{2-[4-(2-Fluoro-phenyl)-[1,2,3]triazol-1-yl]-ethyl}-estra-1,3,5(10)-trien-17-one;

3-Hydroxy-15β-[3-(4-phenethyl-[1,2,3]triazol-1-yl)-propyl]-estra-1,3,5(10)-trien-17-one;

3-Hydroxy-15β-{2-[4-(3-trifluoromethyl-phenyl)-[1,2,3]triazol-1-yl]-ethyl}-estra-1,3,5(10)-trien-17-one;

3-Hydroxy-15β-{2-[4-(4-trifluoromethyl-phenyl)-[1,2,3]triazol-1-yl]-ethyl}-estra-1,3,5(10)-trien-17-one;

3-Hydroxy-15β-{2-[4-(4-methoxy-phenyl)-[1,2,3]triazol-1-yl]-ethyl}-estra-1,3,5(10)-trien-17-one;

3-Hydroxy-15β-[2-(4-iso-butyl-[1,2,3]triazol-1-yl)-ethyl]-estra-1,3,5(10)-trien-17-one;

3-Hydroxy-15β-{2-[4-(4-trifluoromethoxy-phenyl)-[1,2,3]triazol-1-yl]-ethyl}-estra-1,3,5(10)-trien-17-one;

3-Hydroxy-15α-[3-(4-phenethyl-[1,2,3]triazol-1-yl)-propyl]-estra-1,3,5(10)-trien-17-one;

3-Hydroxy-15β-{3-[4-(3-methyl-butyl)-[1,2,3]triazol-1-yl]-propyl}-estra-1,3,5(10)-trien-17-one;

3-Hydroxy-15β-{3-[4-(3,5-difluoro-phenyl)-[1,2,3]triazol-1-yl]-propyl}-estra-1,3,5(10)-trien-17-one;

3-Hydroxy-15β-{2-[4-(2-trifluoromethyl-phenyl)-[1,2,3]triazol-1-yl]-ethyl}-estra-1,3,5(10)-trien-17-one;

3-Hydroxy-15α-{3-[4-(4-methoxy-phenyl)-[1,2,3]triazol-1-yl]-propyl}-estra-1,3,5(10)-trien-17-one;

3-Hydroxy-15β-[3-(4-cyclohexylmethyl-[1,2,3]triazol-1-yl)-propyl]-estra-1,3,5(10)-trien-17-one;

3-Hydroxy-15α-{3-[4-(3-hydroxy-phenyl)-[1,2,3]triazol-1-yl]-propyl}-estra-1,3,5(10)-trien-17-one;

3-Hydroxy-15β-[3-(4-iso-butyl-[1,2,3]triazol-1-yl)-propyl]-estra-1,3,5(10)-trien-17-one;

3-Hydroxy-15α-[3-(4-p-tolyl-[1,2,3]triazol-1-yl)-propyl]-estra-1,3,5(10)-trien-17-one;

3-Hydroxy-15β-{3-[4-(2,4-difluoro-phenyl)-[1,2,3]triazol-1-yl]-propyl}-estra-1,3,5(10)-trien-17-one;

3-Hydroxy-15α-{3-[4-(3-methyl-butyl)-[1,2,3]triazol-1-yl]-propyl}-estra-1,3,5(10)-trien-17-one;

3-Hydroxy-15α-[3-(4-iso-butyl-[1,2,3]triazol-1-yl)-propyl]-estra-1,3,5(10)-trien-17-one;

3-Hydroxy-15β-{3-[4-(4-trifluoromethoxy-phenyl)-[1,2,3]triazol-1-yl]-propyl}-estra-1,3,5(10)-trien-17-one;

4-{1-[3-(3-Methoxy-15β-17-oxo-estra-1,3,5(10)-trien-15-yl)-propyl]-1H-[1,2,3]triazol-4-yl}-benzoic acid methyl ester;

15β-{3-[1-(2,4-difluorophenyl)-1H-1,2,3-triazol-4-yl]propyl}-3-hydroxyestra-1(10),2,4-trien-17-one;

15β-[3-(1-butyl-1H-1,2,3-triazol-4-yl)propyl]-3-hydroxyestra-1(10),2,4-trien-17-one; and 15β-{3-[1-(2,4-difluorophenyl)-1H-1,2,3-triazol-4-yl]propyl}-17,17-difluoroestra-1(10),2,4-trien-3-ol or a physiologically compatible salt or prodrug thereof.

18. A pharmaceutical composition comprising a pharmacologically effective amount of a compound corresponding to formula (I) according to claim 1 and at least one auxiliary or carrier substance.

19. A method for treating a steroid hormone dependent disease or disorder in a human or mammal, said method comprising administering to a subject in need thereof a pharmaceutically effective amount of a compound of formula (I) according to claim 1, wherein the steroid hormone dependent disease or disorder is an estradiol dependent disease or disorder and wherein the estradiol dependent disease or disorder is malign and is selected from the group consisting of breast cancer, ovarian cancer, uterine cancer, endometrial cancer, and endometrial hyperplasia or the estradiol dependent disease or disorder is benign and is selected from the group consisting of endometriosis, uterine fibroids, uterine leiomyoma, adenomyosis, dysmenorrhea, menorrhagia, metrorrhagia, and urinary dysfunction;

the steroid hormone dependent disease or disorder is an androgen-dependent disease or disorder selected from the group consisting of prostate cancer, prostadynia, benign prostatic hyperplasia, urinary dysfunction, lower urinary tract syndrome, prostatitis, acne, seborrhea, androgenetic alopecia, hirsutism, precocious puberty, adrenal hyperplasia, and polycystic ovarian syndrome; or the steroid hormone dependent disease or disorder is selected from the group consisting of squamous cell carcinoma, colon cancer, osteoporosis, rheumatoid arthritis, multiple sclerosis, cognitive dysfunctions, senile dementia, Alzheimer's disease, thyroiditis, vasculitis, ulcerative colitis, Crohn's disease, type I and II diabetes, psoriasis, contact dermatitis, skin wrinkles, tissue wounds, systemic lupus erythematosus, graft versus host disease, organ rejection following transplantation, cataracts and asthma.

20. A process for preparing a compound corresponding to formula (Ix)

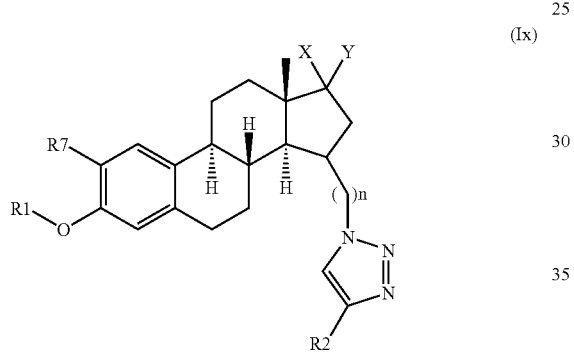

wherein
n represents 1, 2, 3, 4, 5 or 6
X, Y individually represent F, or X and Y together represent =O
$R^1$ is selected from the group consisting of:
(a) —H,
(b) —($C_1$-$C_6$)alkyl, which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$OR^3$, —$SR^3$ or —$COOR^3$ moieties, or which is optionally substituted by aryl, in which the aryl moiety is optionally substituted by 1 or 2 substituents selected from the group consisting of halogen, hydroxyl or —($C_1$-$C_6$)alkyl, and
(c) -phenyl, which is optionally substituted by halogen, carbonitril, —$OR^3$, —$SR^3$, —$COOR^3$, or —($C_1$-$C_6$)alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —($C_1$-$C_6$)alkyl moieties,
wherein each $R^3$ is independently selected from the group consisting of H, —($C_1$-$C_6$)alkyl, optionally substituted by 1, 2 or 3 halogens and/or optionally substituted by 1, 2 or 3 hydroxyl moieties; and aryl, optionally substituted by 1, 2 or 3 halogens, $R^2$ is selected from the group consisting of:
(a) —($C_1$-$C_8$)alkyl,
which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
(b) aryl or aryl-($C_1$-$C_8$)alkyl,
in which the aryl moiety is monocyclic or bicyclic;
and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties;
and in which the alkyl moiety is optionally substituted by 1, 2 or 3 halogens;
(c) heteroaryl or heteroaryl-($C_1$-$C_8$)alkyl,
in which the heteroaryl moiety contains one, two or three heteroatoms independently selected from the group consisting of N, O or S, the number of N atoms being 0, 1, 2 or 3, and the number of O and S atoms each being 0, 1 or 2,
and which heteroaryl moiety is optionally substituted by halogen, carbonitril, nitro, —$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties,
and in which the alkyl moiety is optionally substituted by 1, 2 or 3 halogens;
(d) ($C_3$-$C_8$)cycloalkyl or ($C_3$-$C_8$)cycloalkyl-($C_1$-$C_8$)alkyl,
in which the cycloalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$R^6$, —O—$SO_2$—$R^4$, —$NR^4R^5$ and —$COR^4$ moieties;
(e) cycloheteroalkyl or cycloheteroalkyl-($C_1$-$C_8$)alkyl,
in which the cycloheteroalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$ and —$COR^4$ moieties; and
(f) —($C_1$-$C_8$)alkanoyl
wherein
each $R^4$ and $R^5$ is independently selected from the group consisting of H, —($C_1$-$C_6$)alkyl, optionally substituted by 1, 2 or 3 halogens and/or optionally substituted by 1, 2 or 3 hydroxyl moieties; and aryl and aryl-($C_1$-$C_6$)alkyl, optionally substituted in the aryl moiety by 1, 2 or 3 halogens, or
$R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and $R^6$ represents —$(C_1$-$C_6)$alkyl, which is optionally substituted by 1, 2 or 3 halogens and/or optionally substituted by 1, 2 or 3 hydroxyl moieties;

$R^7$ is selected from the group consisting of
(a) H,
(b) $(C_1$-$C_4)$alkyl,
(c) $(C_1$-$C_4)$alkoxy, and
(d) $(C_1$-$C_4)$alkoxy-$(C_1$-$C_4)$alkyl moiety, or a stereoisomer, physiologically compatible salt, or prodrug thereof, comprising the steps of:

reacting a compound corresponding to formula (XII)

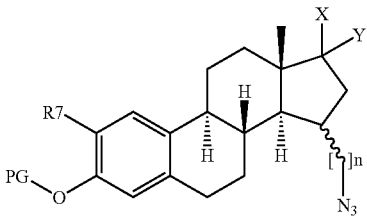

(XII)

wherein X, Y, $R^7$ and n have the meanings as defined above and PG is a protecting group, by a copper catalyzed coupling with a terminal alkine of formula A,

(A)

wherein $R^2$ has the meanings as defined above, wherein different copper sources are used, selected from the group consisting of copper sources wherein copper has the oxidation states 0, I or II, and wherein the protecting group is replaced after the coupling reaction by $R^1$, which has the meaning as defined above.

21. A process for preparing a compound corresponding to formula (Ic)

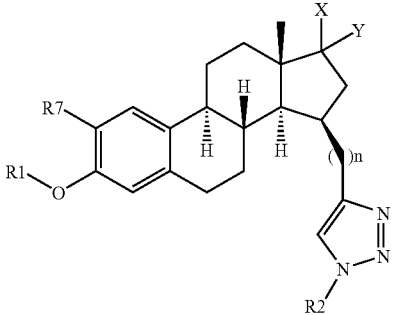

(Ic)

wherein
n represents 1, 2, 3, 4, 5 or 6
X, Y individually represent F, or X and Y together represent =O
$R^1$ is selected from the group consisting of:
(d) —H,
(e) —$(C_1$-$C_6)$alkyl, which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$OR^3$, —$SR^3$ or —$COOR^3$ moieties,
or which is optionally substituted by aryl, in which the aryl moiety is optionally substituted by 1 or 2 substituents selected from the group consisting of halogen, hydroxyl or —$(C_1$-$C_6)$alkyl, and
(f) -phenyl, which is optionally substituted by halogen, carbonitril, —$OR^3$, —$SR^3$, —$COOR^3$, or —$(C_1$-$C_6)$ alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —$(C_1$-$C_6)$alkyl moieties,
wherein each $R^3$ is independently selected from the group consisting of H, —$(C_1$-$C_6)$alkyl, optionally substituted by 1, 2 or 3 halogens and/or optionally substituted by 1, 2 or 3 hydroxyl moieties; and aryl, optionally substituted by 1, 2 or 3 halogens, $R^2$ is selected from the group consisting of:
(g) —$(C_1$-$C_8)$alkyl,
which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
(h) aryl or aryl-$(C_1$-$C_8)$alkyl,
in which the aryl moiety is monocyclic or bicyclic;
and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties;
and in which the alkyl moiety is optionally substituted by 1, 2 or 3 halogens;
(i) heteroaryl or heteroaryl-$(C_1$-$C_8)$alkyl,
in which the heteroaryl moiety contains one, two or three heteroatoms independently selected from the group consisting of N, O or S, the number of N atoms being 0, 1, 2 or 3, and the number of O and S atoms each being 0, 1 or 2,
and which heteroaryl moiety is optionally substituted by halogen, carbonitril, nitro, —$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties,
and in which the alkyl moiety is optionally substituted by 1, 2 or 3 halogens;
(j) $(C_3$-$C_8)$cycloalkyl or $(C_3$-$C_8)$cycloalkyl-$(C_1$-$C_8)$ alkyl,
in which the cycloalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^6$ and —$COR^4$ moieties, (k) cycloheteroalkyl or cycloheteroalkyl-$(C_1-C_8)$alkyl,
in which the cycloheteroalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$ and —$COR^4$ moieties; and (l) —$(C_1-C_8)$alkanoyl
wherein
each $R^4$ and $R^5$ is independently selected from the group consisting of H, —$(C_1-C_6)$alkyl, optionally substituted by 1, 2 or 3 halogens and/or optionally substituted by 1, 2 or 3 hydroxyl moieties; and aryl and aryl-$(C_1-C_6)$alkyl, optionally substituted in the aryl moiety by 1, 2 or 3 halogens, or
$R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and
$R^6$ represents —$(C_1-C_6)$alkyl, which is optionally substituted by 1, 2 or 3 halogens and/or optionally substituted by 1, 2 or 3 hydroxyl moieties;
$R^7$ is selected from the group consisting of
(e) H,
(f) $(C_1-C_4)$alkyl,
(g) $(C_1-C_4)$alkoxy, and
(h) $(C_1-C_4)$alkoxy-$(C_1-C_4)$alkyl moiety,
or a stereoisomer, physiologically compatible salt, or prodrug thereof, comprising the steps of:
reacting a compound corresponding to formula (XXXII-Ia)

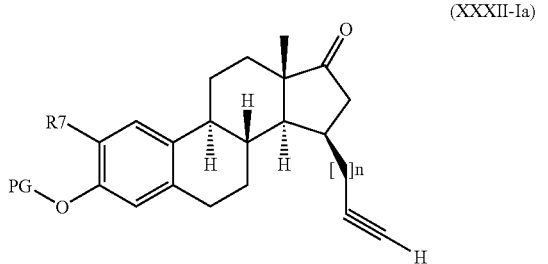

(XXXII-Ia)

wherein $R^7$ and n have the meanings as defined above and PG is a protecting group,
by a Cu (I)-catalyzed coupling with a halide of formula B,

(B)

wherein $R^2$ has the meanings as defined above,
wherein an optional modification of the $C_{17}$ keto group yields compounds of formula (Ic) with X, Y=F, and
wherein the protecting group is replaced after the coupling reaction by $R^1$, which has the meaning as defined above.

22. A process for preparing a compound corresponding to formula (Id)

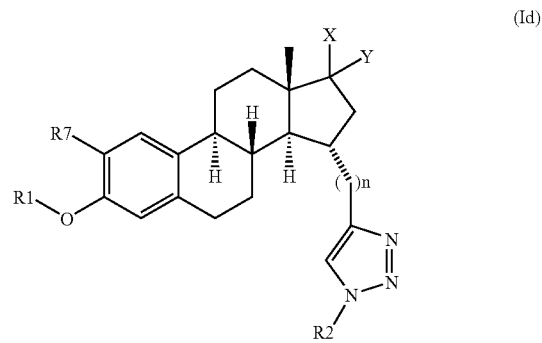

(Id)

wherein
n represents 3 or 4
X, Y individually represent F, or X and Y together represent =O
$R^1$ is selected from the group consisting of:
(g) —H,
(h) —$(C_1-C_6)$alkyl, which is optionally substituted by halogen, carbonitril, —$OR^3$, —$SR^3$ or —$COOR^3$; the number of said substituents being 1, 2 or 3 for halogen, and 1 or 2 for any combination of said halogen, carbonitril, —$SR^3$ or —$COOR^3$ moieties,
or which is optionally substituted by aryl, in which the aryl moiety is optionally substituted by 1 or 2 substituents selected from the group consisting of halogen, hydroxyl or —$(C_1-C_6)$alkyl, and
(i) -phenyl, which is optionally substituted by halogen, carbonitril, —$OR^3$, —$SR^3$, —$COOR^3$, or —$(C_1-C_6)$alkyl, optionally substituted by 1, 2 or 3 halogens, and/or optionally substituted by 1, 2 or 3 hydroxyl moieties; the number of said substituents on the phenyl moiety being 1, 2, 3 or 4 for halogen, and 1 or 2 for any combination of said halogen, carbonitril, —$OR^3$, —$SR^3$, —$COOR^3$ and —$(C_1-C_6)$alkyl moieties,
wherein each $R^3$ is independently selected from the group consisting of H, —$(C_1-C_6)$alkyl, optionally substituted by 1, 2 or 3 halogens and/or optionally substituted by 1, 2 or 3 hydroxyl moieties; and aryl, optionally substituted by 1, 2 or 3 halogens,
$R^2$ is selected from the group consisting of:
(m) —$(C_1-C_8)$alkyl,
which is optionally substituted by halogen, carbonitril, —$OR^4$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —O—$SO_2$—$R^4$, —$NR^4R^5$ and —$COR^4$ moieties;
(n) aryl or aryl-$(C_1-C_8)$alkyl,
in which the aryl moiety is monocyclic or bicyclic;
and which aryl moiety is optionally substituted by halogen, carbonitril, nitro, —$OR^4$, —$R^6$, —O—$SO_2$—$R^4$, —$NR^4R^5$, —$COOR^4$, or —$COR^4$; the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties;
and in which the alkyl moiety is optionally substituted by 1, 2 or 3 halogens;

(o) heteroaryl or heteroaryl-$(C_1$-$C_8)$alkyl,
in which the heteroaryl moiety contains one, two or three heteroatoms independently selected from the group consisting of N, O or S, the number of N atoms being 0, 1, 2 or 3, and the number of O and S atoms each being 0, 1 or 2,
and which heteroaryl moiety is optionally substituted by halogen, carbonitril, nitro, —$OR^4$, —$R^6$, —O—$SO_2$—$R^4$, —$NR^4R^5$, —$COOR^4$ or —$COR^4$, the number of said substituents being 1, 2, 3 or 4 for halogen, and 1 or 2 for any combination of said halogen, carbonitril, nitro, —$OR^4$, —$R^6$, —O—$SO_2$—$R^4$, —$NR^4R^5$, —$COOR^4$ and —$COR^4$ moieties,
and in which the alkyl moiety is optionally substituted by 1, 2 or 3 halogens;
(p) $(C_3$-$C_8)$cycloalkyl or $(C_3$-$C_8)$cycloalkyl-$(C_1$-$C_8)$alkyl,
in which the cycloalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$ and —$COR^4$ moieties,
(q) cycloheteroalkyl or cycloheteroalkyl-$(C_1$-$C_8)$alkyl,
in which the cycloheteroalkyl moiety is optionally substituted by halogen, carbonitril, —$OR^4$, —$R^6$, —O—$SO_2$—$R^4$, —$NR^4R^5$, or —$COR^4$; the number of said substituents being 1, 2 or 3 for halogen, and 1 or 2 for any combination of said halogen, carbonitril, —$OR^4$, —$R^6$, —O—$SO_2$—$R^4$, —$NR^4R^5$ and —$COR^4$ moieties; and
(r) —$(C_1$-$C_8)$alkanoyl
wherein
each $R^4$ and $R^5$ is independently selected from the group consisting of H, —$(C_1$-$C_6)$alkyl, optionally substituted by 1, 2 or 3 halogens and/or optionally substituted by 1, 2 or 3 hydroxyl moieties; and aryl and aryl-$(C_1$-$C_6)$alkyl, optionally substituted in the aryl moiety by 1, 2 or 3 halogens, or
$R^4$ and $R^5$ form together with the nitrogen atom, to which they are attached, a cyclic 5-, 6-, 7- or 8-membered ring system, which is saturated or contains one or more double bonds between the ring atoms, and which ring optionally contains 1 or 2 heteroatoms in addition to the nitrogen atom, wherein the heteroatoms are independently selected from the group consisting of N, O or S, the number of additional N atoms being 0, 1 or 2 and the number of O and S atoms each being 0, 1 or 2, or which ring optionally contains a sulfoxide moiety in addition to the nitrogen atom, and
$R^6$ represents —$(C_1$-$C_6)$alkyl, which is optionally substituted by 1, 2 or 3 halogens and/or optionally substituted by 1, 2 or 3 hydroxyl moieties;
$R^7$ is selected from the group consisting of
(i) H,
(j) $(C_1$-$C_4)$alkyl,
(k) $(C_1$-$C_4)$alkoxy, and
(l) $(C_1$-$C_4)$alkoxy-$(C_1$-$C_4)$alkyl moiety,
or a stereoisomer, physiologically compatible salt, or prodrug thereof, comprising the steps of:
reacting a compound of corresponding to formula (XXXII-Ib)

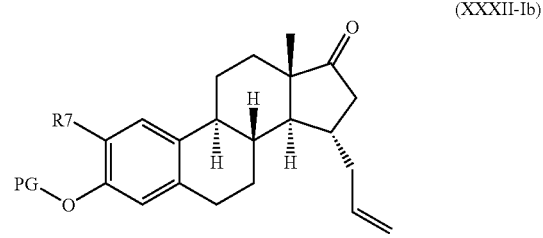

(XXXII-Ib)

wherein $R^7$ has the meanings as defined above and PG is a protecting group,
with a triazole allyl compound of formula C,

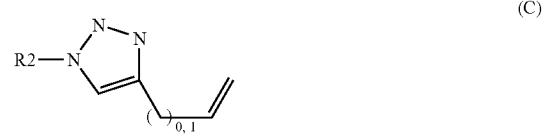

(C)

wherein $R^2$ has the meanings as defined above,
wherein an optional modification of the $C_{17}$ keto group affords compounds of formula (Id) with X, Y=F, and
wherein the protecting group is replaced after the coupling reaction by $R^1$, which has the meaning as defined above.

* * * * *